(12) United States Patent
Morrow et al.

(10) Patent No.: US 10,857,167 B2
(45) Date of Patent: Dec. 8, 2020

(54) USE OF OLIGOSACCHARIDE COMPOSITIONS TO ENHANCE WEIGHT GAIN

(71) Applicant: Children's Hospital Medical Center, Cincinnati, OH (US)

(72) Inventors: Ardythe L. Morrow, Cincinnati, OH (US); Michael A. Helmrath, Cincinnati, OH (US); Ethan Mezoff, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 15/569,993

(22) PCT Filed: Apr. 28, 2016

(86) PCT No.: PCT/US2016/029842
§ 371 (c)(1),
(2) Date: Oct. 27, 2017

(87) PCT Pub. No.: WO2016/176484
PCT Pub. Date: Nov. 3, 2016

(65) Prior Publication Data
US 2018/0153915 A1    Jun. 7, 2018

Related U.S. Application Data

(60) Provisional application No. 62/153,961, filed on Apr. 28, 2015.

(51) Int. Cl.
| | |
|---|---|
| *A61K 31/702* | (2006.01) |
| *A23L 29/30* | (2016.01) |
| *A61P 1/00* | (2006.01) |
| *A23L 33/00* | (2016.01) |
| *A23C 9/20* | (2006.01) |

(52) U.S. Cl.
CPC .............. *A61K 31/702* (2013.01); *A23C 9/20* (2013.01); *A23L 29/30* (2016.08); *A23L 33/30* (2016.08); *A23L 33/40* (2016.08); *A61P 1/00* (2018.01); *A23V 2002/00* (2013.01); *A23V 2250/284* (2013.01)

(58) Field of Classification Search
CPC ......... A61P 1/00; A61K 31/702; A23L 33/30; A23L 33/40
See application file for complete search history.

(56) References Cited

U.S. PATENT DOCUMENTS

| | | |
|---|---|---|
| 3,681,373 A | 8/1972 | Adams et al. |
| 5,470,843 A | 11/1995 | Stahl et al. |
| 5,474,986 A | 12/1995 | Magnusson et al. |
| 5,484,773 A | 1/1996 | Heerze et al. |
| 5,576,300 A | 11/1996 | Mukerji et al. |
| 5,635,606 A | 6/1997 | Heerze et al. |
| 5,700,671 A | 12/1997 | Prieto et al. |
| 5,892,070 A | 4/1999 | Prieto et al. |
| 5,919,913 A | 7/1999 | Nuyens et al. |
| 6,045,854 A | 4/2000 | Prieto et al. |
| 6,126,961 A | 10/2000 | Kross |
| 6,132,710 A | 10/2000 | Panigrahi et al. |
| 6,146,670 A | 11/2000 | Prieto et al. |
| 6,204,431 B1 | 3/2001 | Prieto et al. |
| 6,291,435 B1 | 9/2001 | Yanmaele et al. |
| 6,540,999 B1 | 4/2003 | Harn et al. |
| 7,871,785 B2 | 1/2011 | Morrow et al. |
| 7,893,041 B2 | 2/2011 | Morrow et al. |
| 8,314,061 B2 | 11/2012 | Morrow et al. |
| 8,574,850 B2 | 11/2013 | Morrow et al. |
| 9,034,847 B2 | 5/2015 | Morrow et al. |
| 9,132,142 B2 | 9/2015 | Morrow et al. |
| 9,132,143 B2 | 9/2015 | Morrow et al. |
| 10,098,903 B2 | 10/2018 | Morrow et al. |
| 2002/0019991 A1 | 2/2002 | Prieto et al. |
| 2002/0058313 A1 | 5/2002 | Renkonen et al. |
| 2002/0115839 A1 | 8/2002 | Meyers et al. |
| 2003/0036070 A1 | 2/2003 | Chakravarti |
| 2004/0131659 A1 | 7/2004 | Gibson |
| 2006/0040893 A1 | 2/2006 | Harn et al. |
| 2007/0020660 A1 | 1/2007 | Burczynski et al. |
| 2007/0134251 A1 | 6/2007 | Ashkenazi et al. |
| 2007/0275881 A1 | 11/2007 | Morrow et al. |
| 2009/0098240 A1 | 4/2009 | Mills |

(Continued)

FOREIGN PATENT DOCUMENTS

| | | |
|---|---|---|
| EP | 0 451 462 A1 | 10/1991 |
| EP | 0 870 841 A1 | 10/1998 |

(Continued)

OTHER PUBLICATIONS

Kelly, D. et al "Short bowel syndrome: highlights of patient management . . . " J. Parenter. Enteral Nutr., vol. 38, No. 4, pp. 427-437. (Year: 2014).*
Srinivasjois, R. et al "Prebiotic supplementation in preterm neonates . . . " Clin. Nutr., vo 28, pp. 237-242 (Year: 2009).*
Goulet, O. et al "Intestinal microbiota in short bowel syndrome" Gastroenter. Clin. Biol., vol. 34, Suppl. 1, pp. S37-S43. (Year: 2010).*
Sigalet, D. et al "Nutritional support of infants with intestinal failure . . . " Pediatr. Surg. Int., vol. 29, pp. 975-981. (Year: 2013).*
PCT/US2016/029842, dated Nov. 9, 2017, International Preliminary Report on Patentability.
PCT/US2016/029842, dated Jul. 27, 2016, International Search Report and Written Opinion.

(Continued)

*Primary Examiner* — Leigh C Maier
(74) *Attorney, Agent, or Firm* — McDermott Will & Emery LLP

(57) ABSTRACT

Provided herein are compositions and methods related to use of oligosaccharides, such as 2'-fucosyllactose, for increasing weight gain in a subject. In some aspects the compositions and methods are for use in infants, such as premature infants or infants having intestinal failure.

18 Claims, 40 Drawing Sheets

(56) References Cited

U.S. PATENT DOCUMENTS

| | | |
|---|---|---|
| 2009/0169535 A1 | 7/2009 | Marth |
| 2011/0177035 A1 | 7/2011 | Morrow et al. |
| 2011/0207659 A1 | 8/2011 | Morrow et al. |
| 2012/0202753 A1 | 8/2012 | Morrow et al. |
| 2012/0294840 A1* | 11/2012 | Newburg ............ C07H 3/06 424/93.44 |
| 2014/0140970 A1 | 5/2014 | Morrow et al. |
| 2014/0271562 A1 | 9/2014 | Garcia-Rodenas et al. |
| 2015/0079055 A1 | 3/2015 | Morrow et al. |
| 2015/0265661 A1 | 9/2015 | Newburg et al. |
| 2015/0306120 A1 | 10/2015 | Morrow et al. |
| 2015/0376696 A1 | 12/2015 | Morrow et al. |
| 2016/0143928 A1 | 5/2016 | German et al. |

FOREIGN PATENT DOCUMENTS

| | | | |
|---|---|---|---|
| EP | 1 199 364 A2 | 4/2002 | |
| EP | 2 631 650 A1 | 8/2013 | |
| EP | 2768311 A1 | 8/2014 | |
| EP | 2768313 A1 | 8/2014 | |
| JP | 2002-218996 A | 8/2002 | |
| JP | 2004-528529 A | 9/2004 | |
| JP | 2006-506329 A | 2/2006 | |
| JP | 2009-532372 A | 9/2009 | |
| WO | WO 92/18610 A2 | 10/1992 | |
| WO | WO 94/18986 A1 | 9/1994 | |
| WO | WO 95/24495 A1 | 9/1995 | |
| WO | WO 99/31224 A2 | 6/1999 | |
| WO | WO 99/056754 | 11/1999 | |
| WO | WO 2002/043578 A2 | 6/2002 | |
| WO | WO 2004/041291 A1 | 5/2004 | |
| WO | WO 2005/039319 A2 | 5/2005 | |
| WO | WO 2005/055944 A2 | 6/2005 | |
| WO | WO 2005/110121 A1 | 11/2005 | |
| WO | WO 2006/017859 A2 | 2/2006 | |
| WO | WO 2006/091103 A2 | 8/2006 | |
| WO | WO 2006/133533 A1 | 12/2006 | |
| WO | WO 2007/087468 A2 | 8/2007 | |
| WO | WO 2007/090894 A1 | 8/2007 | |
| WO | WO 2009/033011 A1 | 3/2009 | |
| WO | WO 2009/077352 A1 | 6/2009 | |
| WO | WO 2010/065652 A1 | 6/2010 | |
| WO | WO 2011/005681 A1 | 1/2011 | |
| WO | WO 2013/025104 A1 | 2/2013 | |
| WO | WO 2013/057072 A1 | 4/2013 | |
| WO | WO-2013057062 A1 * | 4/2013 | ......... A61K 31/7016 |
| WO | WO 2017/046711 A1 | 3/2017 | |

OTHER PUBLICATIONS

[No Author Listed], definition for term "entero-"; The Free Dictionary. http://www.thefreedictionary.com/entero-. Retrieved Jan. 13, 2016. 1 page.

[No Author Listed], definition for term "-itis"; The Free Dictionary. http://www.thefreedictionary.com/-itis. Retrieved Jan. 13, 2016. 1 page.

[No Author Listed], Dorland's Illustrated Medical Dictionary, 27th Edition, 1988, p. 228.

[No Author Listed], Quantikine Total Adiponectin ELISA Kit. Retrieved from http://www.funakoshi.co.jp/contents/6797. Last accessed Dec. 18, 2014.

Albermann et al., Synthesis of the milk oligosaccharide 2'-fucosyllactose using recombinant bacterial enzymes. Carbohydr Res. Aug. 23, 2001;334(2):97-103.

Anderson et al., Improved method for the isolation of 2' fucosyllactose from human milk. J Chromatogr. Jun. 26, 1981;211(1):170-4.

Barclay et al., Systematic review: the role of breastfeeding in the development of pediatric inflammatory bowel disease. J Pediatr. Sep. 2009;155(3):421-6. doi:10.1016/j.jpeds.2009.03.017. Epub May 22, 2009.

Beck et al., Exploring the interplay of barrier function and leukocyte recruitment in intestinal inflammation by targeting fucosyltransferase VII and trefoil factor 3. Am J Physiol Gastrointest Liver Physiol. Jul. 2010;299(1):G43-53. doi: 10.1152/ajpgi.00228.2009. Epub Mar. 18, 2010.

Bin-Nun et al., Oral probiotics prevent necrotizing enterocolitis in very low birth weight neonates. J Pediatr. Aug. 2005;147(2):192-6.

Blackwell, The role of ABO blood groups and secretor status in host defences. FEMS Microbiol Immunol. Jun. 1989;1(6-7):341-9.

Bode et al., Human milk oligosaccharides reduce platelet-neutrophil complex formation leading to a decrease in neutrophil beta 2 integrin expression. J Leukoc Biol. Oct. 2004;76(4):820-6. Epub Jul. 7, 2004.

Bode et al., Inhibition of monocyte, lymphocyte, and neutrophil adhesion to endothelial cells by human milk oligosaccharides. Thromb Haemost. Dec. 2004;92(6):1402-10.

Bode, Recent advances on structure, metabolism, and function of human milk oligosaccharides. J Nutr. Aug. 2006;136(8):2127-30. Review.

Boehm et al., Oligosaccharides from milk J Nutr. Mar. 2007;137(3 Suppl 2):847S-9S.

Boehm et al., Supplementation of a bovine milk formula with an oligosaccharide mixture increases counts of faecal bifidobacteria in preterm infants. Arch Dis Child Fetal Neonatal Ed. May 2002;86(3):F178-81.

Brazil et al., α3/4 Fucosyltransferase 3—Dependent Synthesis of Sialyl Lewis A on CD44 Variant Containing Exon 6 Mediates Polymorphonuclear Leukocyte Detachment from Intestinal Epithelium during Transepitheial Migration, J Immunol. Nov. 1, 2013;191(9):4804-17. doi: 10.4049/jimmunol.1301307. Epub Sep. 25, 2013.

Brown et al., Altered immune system glycosylation causes colitis in alpha1,2-fucosyltransferase transgenic mice. Inflamm Bowel Dis. Sep. 2004;10(5):546-56.

Buescher. Anti-inflammatory characteristics of human milk: how, where, why. Adv Exp Med Biol. 2001;501:207-22.

Caplan et al., Bifidobacterial supplementation reduces the incidence of necrotizing enterocolitis in a neonatal rat model. Gastroenterology. Sep. 1999;117(3):577-83.

Catala et al., Oligofructose contributes to the protective role of bifidobacteria in experimental necrotising enterocolitis in quails. J Med Microbiol. Jan. 1999;48(1):89-94.

Chaturvedi et al., Fucosylated human milk oligosaccharides vary between individuals and over the course of lactation. Glycobiology. May 2001;11(5):365-72.

Chaturvedi et al., Milk oligosaccharide profiles by reversed-phase HPLC of their perbenzoylated derivatives. Anal Biochem. Aug. 15, 1997;251(1):89-97.

Chen et al., Probiotics and prebiotics: role in clinical disease states. Adv Pediatr. 2005;52:77-113.

Cheromcha et al., Neonatal necrotizing enterocolitis. Inflammatory bowel disease of the newborn. Dig Dis Sci. Mar. 1988;33(3 Suppl):78S-84S. Abstract.

Chirico et al., Antiinfective properties of human milk. J Nutr. Sep. 2008;138(9):1801S-1806S.

Claud, Neonatal Necrotizing Enterocolitis—Inflammation and Intestinal Immaturity. Antiinflamm Antiallergy Agents Med Chem. Sep. 2009;8(3):248-259. Abstract.

Collins et al., Probiotics, prebiotics, and synbiotics: approaches for modulating the microbial ecology of the gut. Am J Clin Nutr. May 1999;69(5):1052S-1057S. Review.

Conway et al., p40phox expression regulates neutrophil recruitment and function during the resolution phase of intestinal inflammation. J. Immunol. Oct. 1, 2012;189(7):3631-40. Epub Aug. 22, 2012.

Cooper et al., Immunohistologic study of ulcerative colitis with monoclonal antibodies against tumor-associated and/or differentiation antigens. Gastroenterology. Sep. 1988;95(3):686-93.

Coppa et al., Human milk oligosccharides inhibit the adhesion . . . Ped. Res. 2006 v59(3), pp. 377-382.

Cordon-Cardo et al., Immunohistologic expression of blood-group antigens in normal human gastrointesttinal tract and colonic carcinoma. Int J Cancer. May 15, 1986;37(5):667-76.

Cregg et al., Recombinant protein expression in Pichia pastoris. Mol Biotechnol. Sep. 2000;16(1):23-52.

(56) References Cited

OTHER PUBLICATIONS

D'Adamo et al., Metabolic and immunologic consequences of ABH secretor and Lewis subtype status. Altern Med Rev. Aug. 2001;6(4):390-405.
Daddaoua et al., Goat milk oligosaccharides are anti-inflammatory in rats with hapten-induced colitis. J Nutr. Mar. 2006;136(3):672-6.
Dai et al., Role of oligosaccharides and glycoconjugates in intestinal host defense. J Pediatr Gastroenterol Nutr. 2000;30 Suppl 2:S23-33.
Dean et al., The VRG4 gene is required for GDP-mannose transport into the lumen of the Golgi in the yeast, *Saccharomyces cerevisiae*. J Biol Chem. Dec. 12, 1997;272(50):31908-14.
Dooley et al., Regulation of gene expression in inflammatory bowel disease and correlation with IBD drugs: screening by DNA microarrays. Inflamm Bowel Dis. Jan. 2004;10(1):1-14.
Eiwegger et al., Human milk-derived oligosaccharides and plant-derived oligosaccharides stimulate cystokine production of cord blood T-cells in vitro. Pediatr Res. Oct. 2004;56(4):536-40. Epub Aug. 4, 2004.
Ewaschuk et al., Probiotics and prebiotics in chronic inflammatory bowel diseases. World J Gastroenterol. Oct. 7, 2006;12(37):5941-50. Review.
Frost et al., The importance of pro-inflammatory signaling in neonatal necrotizing enterocolitis. Semin Perinatol. Apr. 2008;32(2):100-6. doi: 10.1053/j.semperi.2008.01.001.
Gao et al., Identification of a conserved motif in the yeast golgi GDP-mannose transporter required for binding to nucleotide sugar. J Biol Chem. Feb. 9, 2001;276(6):4424-32. Epub Nov. 6, 2000.
Gokmen-Polar et al., Elevated protein kinase C betaII is an early promotive event in colon carcinogenesis. Cancer Res. Feb. 15, 2001;61(4):1375-81.
Grazioso et al., Anti-inflammatory effects of human milk on chemically induced colitis in rats. Pediatr Res. Nov. 1997;42(5):639-43.
Hallstrom et al., Effects of mode of delivery and necrotising enterocolitis on the intestinal microflora in preterm infants. Eur J Clin Microbiol Infect Dis. Jun. 2004;23(6):463-70. Epub May 27, 2004.
Hanisch et al., Structures of acidic O-linked polylactosaminoglycans on human skim milk mucins. Glycoconj J. 1990;7(6):525-43.
Hanisch et al., Structures of neutral O-linked polylactosaminoglycans on human skim milk mucins. A novel type of linearly extended poly-N-acetyllactosamine backbones with Gal beta(1-4)GlcNAc beta(1-6) repeating units. J Biol Chem. Jan. 15, 1989;264(2):872-83.
Haynes et al., Proteome analysis: biological assay or data archive? Electrophoresis. Aug. 1998;19(11):1862-71.
Heneghan et al., Effect of host Lewis and ABO blood group antigen expression on Helicobacter pylori colonisation density and the consequent inflammatory response. FEMS Immunol Med Microbiol. Apr. 1998;20(4):257-66.
Henry, Molecular diversity in the biosynthesis of GI tract glycoconjugates. A blood-group-related chart of microorganism receptors. Transfus Clin Biol. Jun. 2001;8(3):226-30. Review.
Huang et al., Noroviruses bind to human ABO, Lewis, and secretor histo-blood group antigens: identification of 4 distinct strain-specific patterns. J Infect Dis. Jul. 1, 2003;188(1):19-31. Epub Jun. 12, 2003.
Hurd et al., Increased susceptibility of secretor factor gene Fut2-null mice to experimental vaginal candidiasis. Infect Immun. Jul. 2004;72(7):4279-81.
Ikehara et al., Polymorphisms of two fucosyltransferase genes (Lewis and Secretor genes) involving type I Lewis antigens are associated with the presence of anti-Helicobacter pylori IgG antibody. Cancer Epidemiol Biomarkers Prev. Sep. 2001;10(9):971-7.
Imaoka et al., Anti-inflammatory activity of probiotic Bifidobacterium: enhancement of IL-10 production in peripheral blood mononuclear cells from ulcerative colitis patients and inhibition of IL-8 secretion in HT-29 cells. World J Gastroenterol. Apr. 28, 2008;14(16):2511-6.
Jiang et al., Prevalence of enteric pathogens among international travelers with diarrhea acquired in Kenya (Mombasa), India (Goa), or Jamaica (Montego Bay). J Infect Dis. Feb. 15, 2002;185(4):497-502. Epub Jan. 22, 2002.
Jones et al., Induction of proinflammatory responses in the human monocytic cell line THP-1 by Campylobacter jejuni. Infect Immun May 2003;71(5):2626-33.
Kafetzis et al., Neonatal necrotizing enterocolitis: an overview. Curr Opin Infect Dis. Aug. 2003;16(4):349-55.
Kim et al., Expression of LeY and extended LeY blood group-related antigens in human malignant, premalignant, and nonmalignant colonic tissues. Cancer Res. Nov. 1986;46(11):5985-92.
Klement et al., Breastfeeding and risk of inflammatory bowel disease: a systematic review with meta-analysis. Am J Clin Nutr. Nov. 2004;80(5):1342-52.
Kobayashi et al., Lewis blood group-related antigen expression in normal gastric epithelium, intestinal metaplasia, gastric adenoma, and gastric carcinoma. Am J Gastroenterol. Jun. 1993;88(6):919-24.
Konopka et al., Variable expression of the translocated c-abl oncogene in Philadelphia chromosome-positive B-lymphoid cell lines from chronic myelogenous leukemia patients. Proc Natl Acad Sci U S A. Jun. 1986;83(11):4049-52.
Kunz et al., Oligosaccharides in human milk: structural, functional, and metabolic aspects. Annu Rev Nutr. 2000;20:699-722.
Kunz et al., Potential Anti-Inflammatory and Anti-Infectious Effects of Human Milk Oligosaccharides, Bioactive Components of Milk (Book Series: Advances in Experimental Medicine and Biology, Springer Science & Business Media, New York, NY, US, XP009136897, ISBN: 978-0-387-74086-7: 455-465. 2008.
Lara-Villoslada et al., Oligosaccharides isolated from goat milk reduce intestinal inflammation in a rat model of dextran sodium sulfate-induced colitis. Clin Nutr. Jun. 2006;25(3):477-88. Epub Jan. 10, 2006.
Le Pendu, Histo-blood group antigen and human milk oligosaccharides: genetic polymorphism and risk of infectious diseases. Adv Exp Med Biol. 2004;554:135-43.
Leiper et al., Altered Expression of Fucosyl-Transferases in Inflammatory Bowel Disease. Gastroenterology. 2001;120:A-525, Abstract #2671.
Lewin. Genes VI. Chapter 29—Regulation of transcription. Oxford University Press. 1997: 847-48.
Lin et al., Oral probiotics reduce the incidence and severity of necrotizing enterocolitis in very low birth weight infants. Pediatrics. Jan. 2005;115(1):1-4.
Loftus., Clinical epidemiology of inflammatory bowel disease: Incidence, prevalence, and environmental influences. Gastroenterology. May 2004;126(6):1504-17.
Lucas et al., Breast milk and neonatal necrotising enterocolitis. Lancet. Dec. 22-29, 1990;336(8730):1519-23.
Madjd et al., High expression of Lewis y/b antigens is associated with decreased survival in lymph node negative breast carcinomas. Breast Cancer Res. 2005;7(5):R780-7. Epub Jul. 28, 2005.
Maki, Conversion of GDP-Mannose into Various GDP-Deoxyhexoses in Gram-Negative Bacteria. Academic Dissertation. University of Helsinki, Jun. 16, 2003: 1-63.
Mattila et al., Functional expression of *Escherichia coli* enzymes synthesizing GDP-L-fucose from inherent GDP-D-mannose in *Saccharomyces cerevisiae*. Glycobiology. Oct. 2000;10(10):1041-7.
McGovern et al., Fucosyltransferase 2 (FUT2) non-secretor status is associated with Crohn's disease. Hum Mol Genet. Sep. 1, 2010;19(17):3468-76. doi: 10.1093/hmg/ddq248. Epub Jun. 22, 2010.
Meyrand et al., Comparison of milk oligosaccharides between goats with and without the genetic ability to synthesize α(s1)-casein. Small Rumin Res. Jul. 1, 2013;113(2-3):411-420.
Mikhailov et al., Breastfeeding and genetic factors in the etiology of inflammatory bowel disease in children. World J Gastroenterol. Jan. 21, 2009;15(3):270-9.
Morland et al., Promotion of leukocyte transendothelial cell migration by chemokines derived from human biliary epithelial cells in vitro. Proc Assoc Am Physicians. Jul. 1997;109(4):372-82.

(56) References Cited

OTHER PUBLICATIONS

Morrow et al., Fucosyltransferase 2 non-secretor and low secretor status predicts severe outcomes in premature infants. J Pediatr. May 2011;158(5):745-51. doi: 10.1016/j.jpeds.2010.10.043. Epub Jan. 22, 2011.

Morrow et al., Human milk oligosaccharide blood group epitopes and innate immune protection against campylobacter and calicivirus diarrhea in breastfed infants. Adv Exp Med Biol. 2004;554:443-6.

Morrow et al., Human milk oligosaccharides are associated with protection against diarrhea in breast-fed infants. J Pediatr. Sep. 2004;145(3):297-303.

Morrow et al., Human-milk glycans that inhibit pathogen binding protect breast-feeding infants against infectious diarrhea. J Nutr. May 2005;135(5):1304-7.

Moss et al., Th1/Th2 cells in inflammatory disease states: therapeutic implications. Expert Opin Biol Ther. Dec. 2004;4(12):1887-96.

Nakamura et al., The milk oligosaccharides of domestic farm animals. Trends in glycolscience glycotechnol. Mar. 2004;16(88):135-142.

Nakayama et al., CD15 Expression in Mature Granulocytes is Determined by α1,3-Fucosyltransferase IX, but in Promyelocytes and Monocytes by α1,3-Fucosyltransferase IV. J Biol Chem. May 11, 2001;276(19):16100-6. doi: 10.1074/jbc.M007272200. Epub Feb. 23, 2001.

Nanthakumar et al., Inflammation in the developing human intestine: A possible pathophysiologic contribution to necrotizing enterocolitis. Proc Natl Acad Sci U S A. May 23, 2000;97(11):6043-8.

Newburg et al., Human milk alphal,2-linked fucosylated oligosaccharides decrease risk of diarrhea due to stable toxin of *E. coli* in breastfed infants. Adv Exp Med Biol. 2004;554:457-61.

Newburg et al., Human milk glycans protect infants against enteric pathogens. Annu Rev Nutr. 2005;25:37-58.

Newburg et al., Innate protection conferred by fucosylated oligosaccharides of human milk against diarrhea in breastfed infants. Glycobiology. Mar. 2004;14(3):253-63. Epub Nov. 24, 2013. Erratum in: Glycobiology. May 2004;14(5):13G.

Newburg et al., Protection of the neonate by the innate immune system of developing gut and of human milk. Pediatr Res. Jan. 2007;61(1):2-8. Review.

Newburg et al., α1,2-linked fucosyloligosaccharides comprise a major component of the innate immune system of human milk. Glycobiology 2003, #233; 13(11):885.

Newburg, Human Milk Glycoconjugates that Inhibit Pathogens. Current Medicinal Chemistry, Bentham Science Publishers BV, BE, vol. 6, No. 2, Jan. 1, 1999: 117-127.

Newburg, Human milk oligosaccharides and glycoconjugates protect the newborn against infection. Pediatric Research. 1999; 45:742. Abstract. doi:10.1203/00006450-199905010-00027.

Newburg, Neonatal protection by an innate immune system of human milk consisting of oligosaccharides and glycans. J Anim Sci. Apr. 2009;87(13 Suppl):26-34. doi: 10.2527/jas.2008-1347. Epub Nov. 21, 2008.

Notice of Opposition to a European patent 2451462. N.V. Nutricia. Jun. 5, 2018. Brief.

Notice of Opposition to EP 2451462 dated Jun. 5, 2018. N.V. Nutricia.

Notice of Opposition to EP 2451462 dated Jun. 6, 2018. Grunecker.

Notice of Opposition to EP 2451462 dated Jun. 6, 2018. Grunecker. Brief.

Orlando, The immunologic significance of breast milk. J Obstet Gynecol Neonatal Nurs. Sep. 1995;24(7):678-83.

Parashar et al., Diarrheal mortality in US infants. Influence of birth weight on risk factors for death. Arch Pediatr Adolesc Med. Jan. 1998;152(1):47-51.

Park et al., Inflammatory bowel disease-attributable costs and cost-effective strategies in the United States: a review. Inflamm Bowel Dis. Jul. 2011;17(7):1603-9. doi: 10.1002/ibd.21488. Epub Nov. 4, 2010. Review.

Pennica et al., WISP genes are members of the connective tissue growth factor family that are up-regulated in wnt-1-transformed cells and aberrantly expressed in human colon tumors. Proc Natl Acad Sci U S A. Dec. 8, 1998;95(25):14717-22.

Podolsky et al., Development of anti-human colonic mucin monoclonal antibodies. Characterization of multiple colonic mucin species. J Clin Invest. Apr. 1986;77(4):1251-62.

Pradel et al., Prevalence and characterization of Shiga toxin-producing *Escherichia coli* isolated from cattle, food, and children during a one-year prospective study in France. J Clin Microbiol. Mar. 2000;38(3):1023-31.

Prestwich et al., Controlled chemical modification of hyaluronic acid: synthesis, applications, and biodegradation of hydrazide derivatives. J Control Release. Apr. 30, 1998;53(1-3):93-103.

Prieto, In vitro and clinical experiences with a human milk oligosaccharide, FFI Journal 2005 v210(11), pp. 1018-1029.

Rausch et al., Colonic mucosa-associated microbiota is influenced by an interaction of Crohn disease and FUT2 (Secretor) genotype. Proc Natl Acad Sci U S A. Nov. 22, 2011;108(47):19030-5. doi: 10.1073/pnas.1106408108. Epub Nov. 8, 2011.

Reinhard et al., Image analysis method to assess adhesion of Helicobacter pylori to gastric epithelium using confocal laser scanning microscopy. J Microbiol Methods. Feb. 2000;39(3):179-87.

Rivero et al., Effect of a new infant formula enriched with prebiotics, probiotics, nucleotides and LC-PUFA on recovery after infection. Advances in Experimental Medicine and Biology. 2005;569:186-7.

Rubaltelli et al., Feeding and Neonatal Necrotizing Enterocolitis. In: Nutrition of the Very Low Birthweight Infant. Eds: Ziegler et al. 1999. 199-210.

Rudloff et al., Detection of ligands for selectins in the oligosaccharide fraction of human milk. Eur J Nutr. Apr. 2002;41(2):85-92.

Ruiz-Palacios et al., Campylobacter jejuni binds intestinal H(O) antigen (Fuc alpha 1, 2Gal beta 1, 4GlcNAc), and fucosyloligosaccharides of human milk inhibit its binding and infection. J Biol Chem. Apr. 18, 2003;278(16):14112-20. Epub Jan. 31, 2003.

Saiman et al., Risk factors for candidemia in Neonatal Intensive Care Unit patients. The National Epidemiology of Mycosis Survey study group. Pediatr Infect Dis J. Apr. 2000;19(4):319-24.

Sharon et al., Safe as mother's milk: carbohydrates as future anti-adhesion drugs for bacterial diseases. Glycoconj J. Jul.-Sep. 2000;17(7-9):659-64.

Sisk et al., Early human milk feeding is associated with a lower risk of necrotizing enterocolitis in very low birth weight infants. J Perinatol. Jul. 2007;27(7):428-33. Epub Apr. 19, 2007. Erratum in: J Perinatol. Dec. 2007;27(12):808.

Snelling, Effects of probiotics on the gastrointestinal tract. Curr Opin Infect Dis. Oct. 2005;18(5):420-6.

Spik et al., Primary and three-dimensional structure of lactotransferrin (lactoferrin) glycans. pp. 21-32 from Lactoferrin: Structure and Function, T.W. Hutchens, ed. Plenum Press, New York, 1994.

Spik et al., Primary structure of the glycans from human lactotransferrin. Eur J Biochem. Jan. 1982;121(2):413-9.

Stromqvist et al., Human milk kappa-casein and inhibition of Helicobacter pylori adhesion to human gastric mucosa. J Pediatr Gastroenterol Nutr. Oct. 1995;21(3):288-96.

Thomsson et al., MUC5B glycosylation in human saliva reflects blood group and secretor status. Glycobiology. Aug. 2005;15(8):791-804. Epub Apr. 6, 2005.

Thurl et al., Detection of four human milk groups with respect to Lewis blood group dependent oligosaccharides. Glycoconj J. Nov. 1997;14(7):795-9.

Thurl et al., Quantification of individual oligosaccharide compounds from human milk using high-pH anion-exchange chromatography. Anal Biochem. Mar. 15, 1996;235(2):202-6.

Treszl et al., Genetic basis for necrotizing enterocolitis—risk factors and their relations to genetic polymorphisms. Front Biosci. Jan. 1, 2006;11:570-80.

Tsuboi et al., Alphal,2fucosylation is a superior predictor of postoperative prognosis for colorectal cancer compared with blood group A, B, or sialyl Lewis X antigen generated within colorectal tumor tissues. Ann Surg Oncol. Jun. 2007;14(6):1880-9. Epub Mar. 21, 2007.

(56) References Cited

OTHER PUBLICATIONS

Updegrove, Necrotizing enterocolitis: the evidence for use of human milk in prevention and treatment. J Hum Lact. Aug. 2004;20(3):335-9.

Urashima et al., Oligosaccharides of milk and colostrum in non-human mammals. Glycoconj J. May 2001;18(5):357-71.

Urashima et al., Recent advances in studies on milk oligosaccharides of cows and other domestic farm animals. Biosci Biotechnol Biochem. 2013;77(3):455-66. Epub Mar. 7, 2013.

Urashima et al., Studies of the neutral trisaccharides of goat (*Capra hircus*) colostrum and of the one- and two-dimensional 1H and 13C NMR spectra of 6'-N-acetylglucosaminyllactose. Carbohydr Res. Sep. 15, 1994;262(2):173-84.

Velupillai et al., Oligosaccharide-specific induction of interleukin 10 production by B220+ cells from schistosome-infected mice: a mechanism for regulation of CD4+ T-cell subsets. Proc Natl Acad Sci U S A. Jan. 4, 1994;91(1):18-22.

Viverge et al., Discriminant carbohydrate components of human milk according to donor secretor types. J Pediatr Gastroenterol Nutr. Oct. 1990;11(3):365-70.

Wakabayashi et al., Lactoferrin research, technology and applications. Int. Dairy J. 2006; 16:1241-51.

Ward, Isolation of Milk Oligosaccharides using solid-phase extraction. Open Glycoscience. 2009;2:9-15.

Wilson et al., Glycoproteomics of milk: differences in sugar epitopes on human and bovine milk fat globule membranes. J Proteome Res. Sep. 2008;7(9):3687-96. doi:10.1021/pr700793k. Epub Jul. 15, 2008.

Wu et al., Identification and characterization of GDP-d-mannose 4,6-dehydratase and GDP-l-fucose snthetase in a GDP-l-fucose biosynthetic gene cluster from Helicobacter pylori. Biochem Biophys Res Commun. Jul. 13, 2001;285(2):364-71.

Yolken et al., Human milk mucin inhibits rotavirus replication and prevents experimental gastroenteritis. J Clin Invest. Nov. 1992;90(5):1984-91.

Ziemer et al., An Overview of Probiotics, Prebiotics and Synbiotics in the Functional Food Concept: Perspectives and Future Strategies International Dairy Journal. 1998; 8:473-79.

U.S. Appl. No. 15/998,799, filed Aug. 16, 2018, Morrow et al.

EP 16787174.8, Sep. 6, 2018, Extended European Search Report.

Akiho et al., Low-grade inflammation plays a pivotal role in gastrointestinal dysfunction in irritable bowel syndrome. World J Gastrointest Pathophysiol. Aug. 15, 2010;1(3):97-105. doi: 10.4291/wjgp.v1.i3.97.

Kim et al., Investigating intestinal inflammation in DSS-induced model of IBD. J Vis Exp. Feb. 1, 2012;(60). pii: 3678. doi:10.3791/3678.

Kim et al., Oligonol prevented the relapse of Dextran Sulfate Sodium-Ulcerative Colitis through enhancing NRF2-mediated antioxidative defense mechanism. Journal of Physiology and Pharmacology. 2018; 69(3):1-13.

Liebregts et al., Immune activation in patients with Irritable Bowel Syndrome. Gastroenterology. 2007; 132: 913-920.

Papadakis et al., Role of Cytokines in the Pathogenesis of Inflammatory Bowel Disease. Ann. Rev. Med. 2000; 51:289-298.

Qin et al., Systematic review of animal models of post-infectious/post-inflammatory irritable bowel syndrome. J Gastroenterol. 2011; 46: 164-174.

Redmond et al., The use of solid-phase extraction with graphitised carbon for the fractionation and purification of sugars. Carbohydrate Research. 1999;319:74-79.

\* cited by examiner relative to β-Actin gene expression. Significant differences in expression of Reg3β, Reg3γ, and α-Defensin 5 found by Mann-Whitney U test between standard diet and 2'FL supplemented groups (for each, p<0.024).

| 46 preterm infants, RNA-Seq data, week 2 of life ||
|---|---|
| *FUT-* | *FUT2+* |
| -Thiamin metabolism | -Citrate cycle |
| -Streptomycin biosynth. | -Plant pathogen interaction |
| -Xenobiotics degradation | -Methane metabolism |
| -Phenylalanine metabolism | |
| -Biosynthesis of sat. FA | |
| -Genetic information processing | |

FIG. 38

USE OF OLIGOSACCHARIDE COMPOSITIONS TO ENHANCE WEIGHT GAIN

CROSS-REFERENCE TO RELATED APPLICATIONS

This application is a National Stage Application under 35 U.S.C. § 371 of PCT International Application No. PCT/US2016/029842, filed Apr. 28, 2016, which claims the benefit under 35 U.S.C. § 119(e) of U.S. provisional application No. 62/153,961 filed Apr. 28, 2015, the contents of each of which are incorporated by reference herein in their entirety.

GOVERNMENT SUPPORT

This invention was made with government support under HD013021 awarded by the National Institutes of Health. The government has certain rights in the invention.

BACKGROUND

Preterm infants tend to demonstrate poor weight gain during hospitalization (as measured by Z-score, which indicates their expected weight for age and gender). Similarly, after intestinal surgery, human patients such as infants tend to lose weight as well as have poor weight gain post-operatively. An important nutritional goal is to achieve catchup growth, for example, to approximate their starting weight-for-age Z-score in infant patients.

Accordingly, there is a need for developing new compositions and methods for increasing weight gain in subjects who tend to lose weight for various reasons, e.g., preterm infants.

SUMMARY

The present disclosure is, at least in part, based on unexpected discoveries that fucosylated oligosaccharides (e.g., 2'-fucosyllactose (2'-FL)) successfully enhanced weight gain in preterm infants, particularly those who are non-FUT2 secretors, and in patients who have undergone intestinal surgery as observed in a mouse model of adaptation following extensive ileocecal resection (ICR).

Accordingly, aspects of the disclosure relate to use of oligosaccharides, such as fucosylated oligosaccharides (e.g., α1,2 fucosylated oligosaccharide such as 2'-fucosyllactose (2'FL)) and/or glycoconjugates containing the fucosylated oligosaccharides, in compositions and methods for increasing weight gain in a subject in need thereof.

In one aspect, the disclosure provides a method of increasing weight gain in a subject by administering an effective amount of a synthetic composition comprising a fucosylated oligosaccharide and/or a glycoconjugate containing the fucosylated oligosaccharide to a subject in need thereof (e.g., a subject who fails to gain weight normally or loses weight abnormally).

In any aspects described herein, the fucosylated oligosaccharide can be an α1,2 fucosylated oligosaccharide. In some examples, the synthetic composition comprises an α1,2 fucosylated oligosaccharide and/or a glycoconjugate containing the α1,2 fucosylated oligosaccharide as its sole source of fucosylated oligosaccharides. An exemplary α1,2 fucosylated oligosaccharide can be selected from the group consisting of: (a) 2'-fucosyllactose (2'FL); (b) lacto-N-fucopentaose I (LNF-I); (c) lacto-N-difucohexaose I (LDFH-I); (d) lactodifuctetraose (LDFT); and (e) a variant of (a)-(d), which is identical to (a)-(d) except that the reducing end is N-acetylglucosamine instead of glucose. Other exemplary fucosylated oligosaccharides are provided herein and are contemplated for use in any one of the methods or compositions described herein.

In any of the methods described herein, the subject can be a premature human infant. The premature human infant can have a gestational age (GA) of less than 37 weeks, less than 34 weeks, or less than 29 weeks. Additionally or alternatively, premature human infant can be characterized by a weight-for-age Z-score of less than -2.0.

In some examples, the subject can be a human patient who has undergone a surgery, for example, an intestinal surgery or a bone marrow transplantation, prior to administration of the composition. The human patient who has undergone an intestinal surgery can have short bowel syndrome. The human patient can be an adult or an infant.

Other subjects who are amenable to any of the methods described herein also include human subjects (e.g., adults or infants) who are suffering from undernutrition.

In some embodiments, the human subject who is administered with any of the compositions described herein can be FUT2 negative.

In any of the methods described herein, the composition can be administered to the subject for a period of time, e.g., at least one month or longer. In some embodiments, the composition can be administered to the subject until an increase in weight gain is observed.

In some embodiments of the method, in the glycoconjugate, the oligosaccharide is conjugated with a carbohydrate, a lipid, a nucleic acid, a protein or a peptide.

In some embodiments, the oligosaccharide is synthesized chemically, purified from milk, or produced in a microorganism.

In some embodiments, the composition further comprises a pharmaceutically acceptable carrier. In some embodiments, the composition is an infant formula.

Also within the scope of the present disclosure are (i) a pharmaceutical composition for use in increasing weight gain in a subject who is in need thereof, the composition comprising any fucosylated oligosaccharide described herein (e.g., 2'-FL) and/or a glycoconjugate containing the fucosylated oligosaccharide, and a pharmaceutically acceptable carrier; and (ii) use of a fucosylated oligosaccharide (e.g., 2'-FL) and/or a glycoconjugate containing the fucosylated oligosaccharide in manufacturing a medicament for use in increasing weight gain in a subject who is in need thereof. The subject can be a subject who fails to gain weight normally or loses weight abnormally. Such a subject may be a premature human infant, a human patient who has undergone a surgery (e.g., an intestinal surgery and/or a bone marrow transplantation), or a human subject who is suffering from undernutrition.

An infant formula comprising any fucosylated oligosaccharide described herein (e.g., 2'-FL) for use in increasing weight gain in an infant who is in need thereof (e.g., a premature human infant, or a human infant who has undergone a surgery (e.g., an intestinal surgery and/or a bone marrow transplantation), or a human infant who is suffering from undernutrition) is also within the scope of the present disclosure.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 38 is a table showing expression of bacterial gene pathways (based on RNA-sequencing data): FUT2 oligosaccharide (of mother and infant) associated with greater energy production in infant.

DETAILED DESCRIPTION OF THE INVENTION

Figure 1:
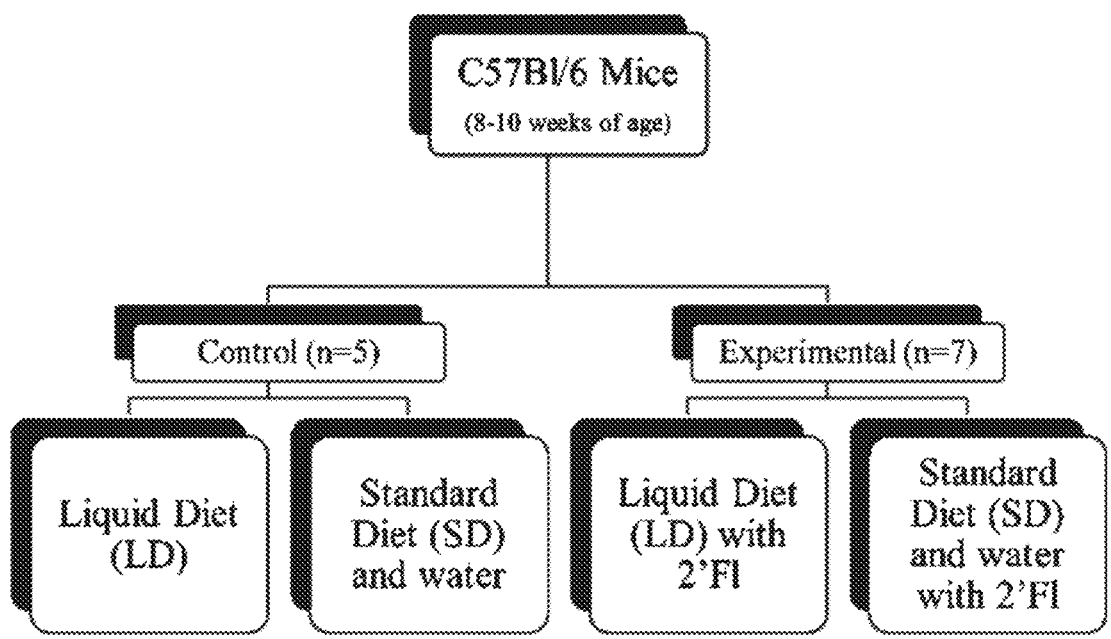
FIG. 1 is a diagram of an exemplary study design as used in Example 1.

There is a need to develop novel methods and compositions for increasing weight gain in subjects who fails to gain weight normally or who loses weight abnormally (e.g., preterm infants, subjects who have undergone a surgery such as an intestinal surgery, or subjects who are suffering from undernutrition). As described herein, among other things, it was shown in a mouse model of adaptation following intestinal resection that treatment with 2'FL as an exemplary α1,2-fucosylated oligosaccharide improved the sustained adaptive response to intestinal resection, as evidenced by an increase in weight gain over time compared to controls. It was also shown that preterm infants (e.g., less than 29 weeks gestational age) who were fed a milk formula comprising 2' FL as an exemplary α1,2-fucosylated oligosaccharide had greater catch-up growth than those who were not. In particular, for preterm infants who are non-secretor or low H phenotype (e.g., FUT2-negative preterm infants), there was greater catch-up growth in those who received milk comprising 2'-FL than in those who did not.

Accordingly, aspects of the disclosure relate to compositions and methods for increasing weight gain in a subject in need thereof utilizing a fucosylated oligosaccharide (e.g., α1,2 fucosylated oligosaccharide, including any of those described herein such as 2'-FL) or a variant or glycoconjugate thereof. Such a subject can be an adult or an infant who have stunted growth or who have lost weight abnormally and thus are in need of increasing the weight gain.

In some aspects, the disclosure relates to methods of increasing weight gain in a subject in need thereof using a fucosylated oligosaccharide, which can increase the weight gain more (e.g., by at least 10% or more) than subjects who are not administered with a fucosylated oligosaccharide.

I. Fucosylated Oligosaccharides and Glycoconjugate Thereof

Fucosylated oligosaccharides for use in the compositions and methods described herein include a minimal disaccharide moiety, in which a fucose residue is covalently linked to another monosaccharide in an α1,2 linkage, an α1,3 linkage, or an α1,4 linkage. In some embodiments, the fucosylated oligosaccharide comprises a core sequence which can be either the lacto type I structure, galactose (β1-3) N-acetylglucosamine-R, abbreviated as {Gal (β1-3) GlcNAc}-R, or the lacto type II structure galactose (β1-4) N-acetylglucosamine-R, abbreviated as {Gal(β1-4)GlcNAc-R}, wherein R is an H, a small radical, or another monosaccharide, disaccharide or polysaccharide or a glycoprotein or glycolipid. These oligosaccharides can be free oligosaccharides or conjugated and expressed as glycoproteins, glycolipids, or other structures. In some embodiments, the fucosylated oligosaccharide can include 2-10 sugar (e.g., 23, 4, 5, 6, 7, 8, 9, 10), containing one or more fucose residues (e.g., 1 or 2) in in an α1,2 linkage, an α1,3 linkage, and/or an α1,4 linkage. Exemplary fucosylated oligosaccharides for use in the compositions and methods described herein are provided in Table 1 below.

In some examples, fucosylated oligosaccharides for use in the compositions and methods described herein can be α1,2 fucosylated oligosaccharides. Examples of α1,2 fucosylated oligosaccharides include, without limitation, 2'-fucosyllactose (2'-FL); lacto-N-fucopentaose-I (LNF-I); lacto-N-difucohexaose I (LDFH I); and lactodifucotetraose (LDFT).

TABLE 1

| | Fucosyl oligosaccharides | |
|---|---|---|
| 2'FL | 2-Fucosyllactose | Fucα1,2Galβ1,4Glc |
| LNF-I | Lacto-N-fucopentaose I | Fucα1,2Galβ1,3GlcNAcβ1,3Galβ1,4Glc |
| LNF-II | Lacto-N-fucopentaose II | Galβ1,3→GlcNAcβ1,3Galβ1,4Glc; Fucα1,4↗ |
| 3'FL | 3-Fucosyllactose | Galβ1,4→Glc; Fucα1,3↗ |
| LNF-III | Lacto-N-fucopentaose III | Galβ1,4→GlcNAcβ1,3Galβ1,4Glc; Fucα1,3↗ |
| LDFH-I | Lacto-N-difucohexaose I | Fucα1,2Galβ1,3→GlcNAcβ1,3Galβ1,4Glc; Fucα1,4↗ |
| LDFT | Lactodifucotetraose | Fucα1,2Galβ1,4→Glc; Fucα1,3↗ |

Alternatively or in addition, fucosylated oligosaccharides for use in the compositions and methods described herein may be sialyl fucosyl oligosaccharides. Such oligosaccharides comprise at least one sialic acid residue, which can be in α-2,3 or α-2,6 linkage, and at least one fucose residue, which can be in α1,2, α1,3, or α1,4-linkage. Examples of sialyl fucosyl oligosaccharides are provided in Table 2 below.

TABLE 2

| | Sialyl fucosyl oligosaccharides | |
|---|---|---|
| 3'-S-3FL | 3'-Sialyl-3-fucosylactose | NANAα2,3Galβ1,4↘<br>Glc<br>Fucα1,3↗ |
| DSFLNH | Disialomonofucosyllacto-N-neohexaose | NANAα2,6Galβ1,4GlcNAcβ1,6↘<br>Fucα1,3↘ Galβ1,4Glc<br>GlcNAcβ1,3↗<br>NANAα2,3Galβ1,4↗ |
| MFMSLNO | Monofucosylmonosialyllacto-N-octaose (sialyl Le$^a$) | Galβ1,4GlcNAcβ1,3Galβ1,4GlcNAcβ1,6↘<br>Galβ1,4Glc<br>NANAα2,3Galβ1,3GlcNAcβ1,3↗<br>Fucα,14↗ |
| SLNFH-II | Sialyllacto-N-fucohexaose II | NANAα2,3Galβ1,3GlcNAcβ1,3Galβ1,4Glc<br>Fucα1,4↑   Fucα1,3↗ |
| DSLNFP-II | Disialyllacto-N-fucopentaose II | NANAα2,6↘<br>NANAα2,3Galβ1,3GlcNAcβ1,3Galβ1,4Glc<br>Fucα1,4↗ |
| MFDLNT | Monofucosyldisialyllacto-N-tetraose | NANAα2,6↘<br>NANAα2,3Galβ1,3GlcNAcβ1,3Galβ1,4Glc<br>Fucα1,4↗ |

The fucosylated oligosaccharides described herein can be prepared by conventional methods, e.g., synthesized chemically, purified from milk, or produced in a microorganism. See WO2005/055944.

For example, fucosylated oligosaccharides described herein can be purified from natural sources, e.g., milk, milk products or plant products, using method known to those in the art. Below is an example of isolating oligosaccharides from milk. Milk is first defatted by centrifugation to produce skimmed milk. The skimmed milk is then mixed with an organic solvent, such as acetone (e.g., 50% aqueous acetone) and ethanol (e.g., 67% aqueous ethanol), to precipitate milk proteins. Upon centrifugation, the supernatant is collected and subjected to chromatography. Fucosylated oligosaccharide-containing fractions are collected and pooled. If necessary, the oligosaccharides thus prepared can be concentrated by conventional methods, e.g., dialysis or freeze-drying.

Fucosylated oligosaccharides can also be isolated from skimmed milk by passing the skimmed milk through a 30,000 MWCO ultrafiltration membrane, collecting the diffusate, passing the diffusate through a 500 MWCO ultrafilter, and collecting the retentate, which contains milk oligosaccharides. The retentate can be subjected to chromatograph, in which fucosylated oligosaccharide-containing fractions are collected and pooled.

Alternatively or in addition, fucosylated oligosaccharides described herein can be synthesized chemically either from naturally occurring precursors or synthetic templates according to methods known in the art. In addition, fucosylated oligosaccharides can be synthesized enzymatically, or biologically, either in vitro, or in vivo, e.g., using genetically engineered microorganisms such as bacteria or yeasts, that express enzymes involved in biosynthesis of a fucosylated oligosaccharide of interest, which are well known in the art. See, e.g., WO2005/055944.

In some embodiments, the fucosylated oligosaccharides are contained within a glycoconjugate. The glycoconjugates, containing one or more fucosylated oligosaccharides described herein, can be chemically synthesized by conjugating the oligosaccharide(s) to a backbone molecule (e.g., a carbohydrate, a lipid, a nucleic acid, or a peptide) directly or via a linker. As used herein, "glycoconjugate" refers to a complex containing a sugar moiety associated with a backbone moiety. The sugar and the backbone moieties can be associated via a covalent or noncovalent bond, or via other forms of association, such as entrapment (e.g., of one moiety on or within the other, or of either or both entities on or within a third moiety). The glycoconjugate described herein can contain one type of fucosylated oligosaccharide (i.e., one or more copies of a fucosylated oligosaccharide attached to one backbone molecule). Alternatively, the glycoconjugate contains multiple types of fucosylated oligosaccharides, wherein each fucose can be covalently linked to a minimal disaccharide precursor, or core sequence in the same or a different configuration (e.g., in an α1,2 configuration, an α1,3 configuration, or an α1,4 configuration). In one example, a fucosylated oligosaccharide (e.g., α1,2 fucosylated oligosaccharides such as 2'-fucosyllactose, lacto-N-difucohexaose I, lactodifucotetraose, lacto-N-fucopentaose I, or an acetylated variant thereof) is covalently linked via its reducing end sugar unit to a lipid, a protein, a nucleic acid, or a polysaccharide. Preferably, the reducing end sugar unit is N-acetylglucosamine.

Peptide backbones suitable for making the glycoconjugate described above include those having multiple glycosylation sites (e.g., asparagine, lysine, serine, or threonine residue) and low allergenic potential. Examples include, but are not limited to, amylase, bile salt-stimulated lipase, casein, folate-binding protein, globulin, gluten, haptocorrin, lactalbumin, lactoferrin, lactoperoxidase, lipoprotein lipase, lysozyme, mucin, ovalbumin, and serum albumin.

In some embodiments, a fucosylated oligosaccharide can be covalently attached to a serine or threonine residue via an O-linkage or attached to an asparagine residue via an N-linkage. To form these linkages, the sugar unit at the reducing end of the oligosaccharide is preferably an acetylated sugar unit, e.g., N-acetylgalactosamine, N-acetylglucosamine, and N-acetylmannosamine. An oligosaccharide can be attached to a peptide (e.g., a protein) using standard methods. See, e.g., McBroom et al., *Complex Carbohydrates, Part B*, 28:212-219, 1972; Yariv et al., *Biochem J.*, 85:383-388, 1962; Rosenfeld et al., *Carbohydr. Res.*, 46:155-158, 1976; and Pazur, *Adv. Carbohydr. Chem, Biochem.*, 39:405-447, 1981.

In one example, a fucosylated oligosaccharide is linked to a backbone molecule via a linker. Exemplary linkers are described in WO2005/055944. The oligosaccharide can be bonded to a linker by an enzymatic reaction, e.g., a glycosyltransferase reaction. A number of glycosyltransferases, including fucosyltransferases, galactosyltransferases, glucosyltransferases, mannosyltransferases, galactosaminyltransferases, sialyltransferases and N-acetylglucosaminyltransferases, can be used to make the glycoconjugate described herein. More details about these glycosyltransferases can be found in U.S. Pat. Nos. 6,291,219; 6,270,987; 6,238,894; 6,204,431; 6,143,868; 6,087,143; 6,054,309; 6,027,928; 6,025,174; 6,025,173; 5,955,282; 5,945,322; 5,922,540; 5,892,070; 5,876,714; 5,874,261; 5,871,983; 5,861,293; 5,859,334; 5,858,752; 5,856,159; and 5,545,553.

Alternatively, the glycoconjugates described herein can be purified from milk by conventional methods e.g., by passing through ultrafiltration membranes, by precipitation in non-polar solvents, or through partition between immiscible solvents.

II. Synthetic Compositions Comprising Fucosylated Oligosaccharides

One or more of the fucosylated oligosaccharides described herein, either in free form or as a moiety of a glycoconjugate as described herein, can be formulated, optionally with one or more additional components (e.g., those described herein), as a synthetic composition. A synthetic composition refers to a composition, as a whole, that is not found in nature. In some instances, the synthetic composition may contain naturally-occurring components; however, the combination of such naturally-occurring components does not exist in nature. For example, the synthetic composition may contain at least one component that does not exist in milk, such as human milk or cow milk. In other instances, at least one component in the synthetic composition is not found in nature.

In some embodiments, the synthetic compositions described herein comprises one or more of the fucosylated oligosaccharides, e.g., those described herein, and one or more carriers, e.g., a pharmaceutically acceptable carrier and/or an edible carrier. Such carriers, either naturally occurring or non-naturally occurring (synthetic), may confer various benefits to the fucosylated oligosaccharide(s) in the composition, for example, improving in vitro and/or in vivo stability of the oligosaccharides, enhancing bioavailability of the oligosaccharides, increasing bioactivity of the oligosaccharides, and/or reducing side effects. Suitable carriers include, but are not limited to, diluents, fillers, salts, buffers, stabilizers, solubilizers, buffering agents, preservatives, or a combination thereof. Lactose and corn starch are commonly used as diluents for capsules and as carriers for tablets. Lubricating agents, such as magnesium stearate, are typically added to form tablets.

In some embodiments, the one or more fucosylated oligosaccharides (which can be a combination of α1,2-fucosylated oligosaccharides, α1,3-fucosylated oligosaccharides, and/or α1,4-fucosylated oligosaccharides) constitute at least 30% by weight (e.g., 40%, 50%, 60%, 70%, 80%, or 90%) of the total sugar content of the synthetic composition. In other embodiments, the concentration (by weight) of the one or more fucosylated oligosaccharides in the synthetic composition is at least 5% (e.g., 10%, 15%, 20%, 25%, or higher).

In some instances, the one or more fucosylated oligosaccharides are the sole source of oligosaccharides (e.g., having less than 15 monosaccharide units) in the synthetic composition. In other words, the synthetic composition is substantially free of other oligosaccharides. As used herein, "substantially free" means that the amount of any other oligosaccharides is substantially low, if any, such that presence of the other oligosaccharides, if any, would be insignificant to affect the intended therapeutic effects attributable to the fucosylated oligosaccharide(s). In one example, the synthetic composition is free of non-fucosylated oligosaccharides.

In some embodiments, the synthetic composition described herein is enriched with α1,2-fucosylated oligosaccharides (e.g., 2'-FL, LNF-III, LDFH-I, and/or LDFT). In some examples, the a 1,2-fucosylated oligosaccharide(s) constitutes at least 30% by weight (e.g., 40%, 50%, 60%, 70%, 80%, or 90%) of the total sugar content of the synthetic composition. In other embodiments, the concentration (by weight) of α1,2-fucosylated oligosaccharides in the synthetic composition is at least 5% (e.g., 10%, 15%, 20%, 25%, or higher). In some instances, the α1,2-fucosylated oligosaccharide(s) is the sole source of oligosaccharides (e.g., having less than 15 monosaccharide units) in the synthetic composition, which means that the synthetic composition is substantially free of other oligosaccharides. In one example, the synthetic composition is free of non-α1, 2-fucosylated oligosaccharides.

One or more of the above-described fucosylated oligosaccharides or glycoconjugates can be mixed with a pharmaceutically acceptable carrier to form a pharmaceutical composition. Such carriers can include, without limitation, sterile aqueous or non-aqueous solutions, suspensions, and emulsions. The carrier in the pharmaceutical composition is "acceptable" in the sense of being compatible with the active ingredient of the formulation (and in some embodiments, capable of stabilizing it) and not deleterious to the subject to be treated. For example, solubilizing agents such as cyclodextrins, which form more soluble complexes with the oligosaccharides/glycoconjugates, or more solubilizing agents, can be utilized as pharmaceutical carriers for delivery of the oligosaccharides/glycoconjugates. Examples of other carriers include colloidal silicon dioxide, magnesium stearate, sodium lauryl sulfate, and D&C Yellow #10. Examples of non-aqueous solvents include mineral oil, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants (e.g., propyl gallate), chelating agents, inert gases, and the like may also be present.

In some embodiments, the oligosaccharides/glycoconjugates can also be formulated as food products or food supplements following methods well known in the food industry. In one example, the oligosaccharides/glycoconjugates are provided as part of an infant formula. In another example, the oligosaccharides/glycoconjugates are provided as parenteral nutrition formulation, or total parenteral nutrition formulation. Exemplary components for inclusion in an infant formula, parenteral nutrition formulation, or total parenteral nutrition formulation with oligosaccharides/glycoconjugates provided herein include any one or more of protein, fat, linoleic acid, vitamins (e.g., A, C, D, E, K, thiamin (B1), riboflavin (B2), B6, and/or B12), niacin, folic acid, pantothenic acid, calcium, minerals (e.g., magnesium, iron, zinc, manganese, and/or copper), phosphorus, iodine, sodium chloride, potassium chloride, carbohydrates, and nucleotides. Other exemplary components for inclusion in an infant formula, parenteral nutrition formulation, or total parenteral formulation include emulsifiers (e.g., monoglycerides, diglycerides, or gums), stabilizers, and diluents (e.g., skim milk or water).

In some embodiments, any of the synthetic compositions described herein can further comprise a probiotic organism microorganism that, when ingested by the host, can modify intestinal microbial populations in a way that benefits the host. Pro biotic organisms may provide an increased barrier to translocation of bacteria and bacterial products across mucosa, competitively exclude potential pathogens, modify of host response to microbial products, and enhance enteral nutrition in ways that inhibits the growth of pathogens such as *Klebsiella pneumoniae*, *Escherichia coli*, and *Candida albicans*.

Probiotic organisms generally include bacteria and yeast. The species of probiotic organism can vary, but suitable species for infants include *Lactobacilli*, e.g., *Lactobacillus rhamnosus* GG, *L. acidophilus, L. casei, L. plantarum, L. reuteri*; and *Bifidobacteria*, e.g., *Bifidobacterium infantis, B. bifidum, B. breve, B. animalis* subsp. *lactis, B. longum*, as well as *Streptococcus thermophilus*. Useful yeast species include *Saccharomyces boulardii* and *Kluyveromyces lactis*. Pro biotic organisms may be either naturally occurring or they may be engineered, i.e., organisms may be provided with genes that enable them to acquire desirable properties such as, but not limited to, the ability to express secretor antigens. Pro biotic organisms may be administered separately or in combination. Commercially available probiotic formulations include, for example, Infloran® (Istituto Sieroterapico Berna, Como, Italy) which contains *Lactobacillus acidophilus/Bifidobacterium infantis*; ABC Dophilus (Solgar, Israel) which contains *Bifidobacterium infantis, B. bifidum* and *Streptococcus thermophilus*; and Dicoflor (Vitis Pharma, Warsaw, Poland) which contains *L. rhamnosus* GG.

In some embodiments, any of the synthetic compositions described herein can further comprise a prebiotic, i.e., a non-digestible food ingredient that beneficially affects the host by selectively stimulating the growth and/or the activity of one or a limited number of bacteria in the colon. In contrast to a pro biotic, which introduces exogenous bacteria into the colonic micro biota, a prebiotic stimulates the growth of one or a limited number of the potentially health-promoting indigenous microorganisms e.g., *Bifidobacteria* or *Lactobacteria*. Examples of prebiotics include fructo-oligosaccharides, e.g., inulin, xylooligosaccharides and galactooligosaccharides. Prebiotics can be isolated from natural sources e.g., chicory roots, soybeans, Jerusalem artichokes, beans, onions, garlic, oats, wheat and barley.

The synthetic compositions described herein can be in any suitable form, such as powder, paste, jelly, capsule, or tablet, which can be prepared by conventional methods known in the pharmaceutical and/or food industry.

Exemplary Applications

Any of the fucosylated oligosaccharides, e.g., those described herein such as $\alpha 1,2$ fucosylated oligosaccharides (e.g., 2'FL, LNF-III, LDFH-I, and/or LDFT), $\alpha 1,3$ fucosylated oligosaccharides (e.g., 3'-FL), $\alpha 1,4$-fucosylated oligosaccharides, or a glycoconjugate containing the fucosylated oligosaccharides, as well as the synthetic compositions comprising such as described herein, can be administered to a subject in need thereof in an amount effective for increasing weight gain in the subject.

In some embodiments, increasing weight gain in a subject means increasing the amount of weight gain or the rate of the weight gain, e.g., by at least 10% (including at least 20%, at least 30%, at least 40%, at least 50%, at least 60%, at least 70%, at least 80%, at least 90%, or higher) compared to that of a control subject who has not received a fucosylated oligosaccharide. In some embodiments, increasing weight gain in a subject means increasing the amount of weight gain or the rate of the weight gain, e.g., by at least 1.1-fold (including at least 1.5-fold, at least 2-fold, at least 3-fold, at least 4-fold, at least 5-fold, at least 6-fold, at least 7-fold, at least 8-fold, at least 9-fold, at least 10-fold, or higher) compared to that of a control subject who has not received a fucosylated oligosaccharide. The control subject should have a similar need of increasing weight gain as the subject being administered a composition comprising a fucosylated oligosaccharide or glycoconjugate thereof. For example, if the subject being administered a composition comprising a fucosylated oligosaccharide or glycoconjugate thereof is a pre-term infant, the control subject should be a pre-term infant as well.

In some embodiments, increasing weight gain in a subject means increasing weight gain such that the weight of the subject becomes comparable (e.g., within 10%) to the average weight of a normal healthy population over a desirable period of time (e.g., a shorter period of time as compared to a subject who has not received a composition described herein). The term "normal healthy subject" generally refers to a subject who has no symptoms of any diseases or disorders, or who is not identified with any diseases or disorders, or who is not on any medication treatment, or a subject who is identified as healthy by a physician based on medical examinations.

In the context of applying the methods and compositions described herein to infants, increasing weight gain can mean increasing the Z-score (e.g., the weight-for-age Z-score) of the subject to above −2.0 (e.g., to above −1.0, to above −0.5, to about 0, or to above 0, etc.).

The subject to be amenable to the methods and compositions described herein can be a human (i.e., a male or a female of any age group, for example, a pediatric subject (e.g., an infant, child, or an adolescent) or an adult subject (e.g., a young adult, a middle-aged adult, or a senior adult)) who fails to gain weight normally or who loses weight abnormally. For example, a subject is considered as failing to gain weight normally when the amount or rate of weight gain of the subject (e.g., a pre-term infant) is lower, e.g., by at least 10% (including at least 20%, at least 30%, at least 40%, at least 50%, or higher) as compared to that of normal healthy subject(s) (e.g., a full-term infant(s)). In some embodiments, a subject who fails to gain weight normally can be an underweight subject, e.g., a subject with a weight of at least 15% or more below that normal for their age and height group. A subject is considered as losing weight abnormally when the weight of the subject is at least 50%, at least 60%, at least 70%, at least 80% or lower than that of normal healthy subject(s). In some instance, a subject can lose weight abnormally, e.g., after a surgery or caused by undernutrition. A "patient" refers to a human subject in need of treatment of a disorder or condition.

The subject may also include any non-human animals including, but not limited to a non-human mammal such as cynomolgus monkey or a rhesus monkey. In certain embodiments, the non-human animal is a mammal, a primate, a rodent, an avian, an equine, an ovine, a bovine, a caprine, a feline, or a canine. The non-human animal may be a male or a female at any stage of development. The non-human animal may be a transgenic animal or a genetically engineered animal.

In some embodiments, the subject is an infant, e.g., a human infant. In some embodiments, the infant is a premature infant (e.g., a premature human infant). In some embodiments, the premature infant (e.g., premature human infant) has a gestational age of less than 37, 36, 35, 34, 33, 32, 31, 30, 29, 28, or 27 weeks.

In some embodiments, the subject is an infant with a weight-for-age Z-score of less than −1.0, less than −2.0, less than −2.5, or lower. The weight-for-age Z-score can be calculated using the following formula: (measured value−average value of a reference population)/standard deviation value of reference population. In some embodiments, the reference population is a population of normally nourished subjects at the indicated age. In some embodiments, the reference population is the population determine by the World Health Organization (WHO) (see, e.g., WHO Multicentre Growth Reference Study Group. WHO Child Growth Standards: Length/height-for-age, weight-for-age, weight-for-length, weight-for-height and body mass index-for-age: Methods and development. Geneva: World Health Organization, 2006). Data for weight-for-age Z-score and corresponding weight for children at different ages (e.g., from birth to 5 years) are also provided by World Health Organization.

In some embodiments, the subject can be an extremely low birthweight infant. Extremely low birth weight (ELBW) is generally defined as a birth weight less than 2500 g or less than 1000 g. In some embodiments, ELBW infants can be also premature newborns.

In some embodiments, the subject (e.g., an infant or an adult) can be a subject who has undergone a surgery, e.g., a surgery that is likely to cause a loss or an abnormal loss in weight (e.g., at least 10 lbs, at least 20 lbs, at least 30 lbs, or more) post-operatively. In some embodiments, the subject (e.g., an infant or an adult) can be a subject who has lost weight after a surgery and has poor weight gain post-operatively. As used herein, the term "surgery" refers to the art, practice, or work of treating diseases, disorders, injuries, or deformities by manual or operative procedures. Examples of a surgery, e.g., a surgery that is likely to cause an abnormal loss in weight post-operatively, include, but is not limited to, an intestinal surgery, a bone marrow transplantation, or a combination thereof. In some embodiments, the subject has undergone intestinal surgery or a bone marrow transplantation before administration of a composition as described herein (e.g., a composition comprising an oligosaccharide, such as 2′FL, or a glycoconjugate of the oligosaccharide).

In some embodiments, the subject can be an infant who has, is suspected of having, or is at risk for gastroschisis, which is congenital defect characterized by a defect in the anterior abdominal wall through which the abdominal contents freely protrude.

In some embodiments, the subject (e.g., an infant or an adult) can have an intestinal failure. In some embodiments, intestinal failure includes a non-functioning or poorly functioning small intestine (e.g., unable to or inefficiently capable of absorbing nutrients and water). Intestinal failure can be caused by injury, disease, or removal of part of the small intestine (e.g., by surgery). The most common cause of intestinal failure is short bowel syndrome (SBS). Short bowel syndrome is a condition that generally occurs following extensive intestinal resection or loss. Diagnostic tests for identifying SBS include blood chemistry tests (e.g., albumin levels or vitamin levels), complete blood counts, fecal fat tests, or small intestine X-ray. Other causes of intestinal failure include pseudo-obstruction and congenital enteropathy. Symptoms of intestinal failure include diarrhea, bloating, vomiting, weakness, weight loss, dehydration and fatigue.

In some embodiments, the subject can be suffering from undernutrition, which can lead to underweight.

In some embodiments, any of the subjects described herein is FUT2 positive (secretory phenotype). Such a subject has a functional or partially functional fucosyltransferase 2 enzyme. In some embodiments, any of the subjects described herein can be also FUT2 negative (non-secretor phenotype). In some embodiments, a subject is FUT2 negative if they have a non-functional or absent fucosyltransferase 2 enzyme, e.g., due to a nonsense mutation in the FUT2 gene (e.g., 428G>A or 385A>T) or deletion of the FUT2 gene. FUT2 genotyping can be performed by any standard method known in the art, for example SNP analysis or RT-PCR techniques. The methods and/or compositions described herein applied to FUT2 negative subjects can increase a greater weight gain, e.g., by at least about 10% or more, including at least about 20%, at least about 30%, at least about 40%, at least about 50%, at least about 60%, at least about 70%, at least about 80%, at least about 90%, or more, as compared to weight gain as observed in a FUT2 positive subject.

Other aspects of the disclosure relate to a method of decreasing time to full enteral feeding in a subject (e.g., a pre-term infant, or a subject who has undergone an intestinal surgery), the method comprising administering to a subject in need thereof an effective amount of a composition comprising a fucosylated oligosaccharide or a glycoconjugate containing the a fucosylated oligosaccharide. In some embodiments, the oligosaccharide is a α1,2 fucosylated oligosaccharide. In some embodiments, the oligosaccharide is selected from the group consisting of (a) 2′-fucosyllactose (2′FL) and (b) a variant of 2′FL, which is identical to 2′FL except that the reducing end is N-acetylglucosamine instead of glucose. In some embodiments, decreasing time to full enteral feeding means decreasing the time to less than 20, 19, 18, 17, 16, 15, 14, 13, 12, 11, or 10 days. In some embodiments, decreasing time to full enteral feeding means decreasing the time to full enteral feeding compared to a subject that has not received the composition.

To perform the methods described herein, an effective amount of a fucosylated oligosaccharide (e.g., those described herein) can be administered to a subject in need thereof (e.g., subjects described herein) via a suitable route.

An "effective amount," or "amount effective to/for", as used herein, refers to an amount of a fucosylated oligosaccharide as described herein that is effective in producing the desired therapeutic, ameliorative, inhibitory or preventative effect, and/or results in a desired clinical effect, such as increased amount or rate of weight gain, or increased weight-for-age Z-score to closer to zero or above zero. Effective amounts vary, as recognized by those skilled in the art, depending on route of administration, excipient usage, and co-usage with other active agents.

In the case of increasing weight gain in a subject who has undergone a surgery, the desired response can also include adaptive response to the surgery. For example, as shown in Example 3, a mouse model of adaptation following extensive ileocecal resection (ICR) showed sustained increases in villus height, crypt depth, and mucosal surface area (due to bowel dilation and lengthening) in mices supplemented with a fucosylated oligosaccharide (e.g., 2'-FL) after ICR. As a result of the adaptive process, the intestinal function of the mices improved, resulting in an increased weight gain in the mices supplemented with a fucosylated oligosaccharide (e.g., 2'-FL) as compared to ones without the supplementation.

Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

For example, an effective amount of a fucosylated oligosaccharide described herein when administered to a subject results in, e.g., increased weight gain in the subject by at least about 10% or more, including, e.g., at least about 20%, at least about 30%, at least about 40%, at least about 50%, at least about 60%, at least about 70%, at least about 80%, at least about 90% or more, as compared to increased weight gain without administration of any fucosylated oligosaccharide described herein. In some embodiments, an effective amount of a fucosylated oligosaccharide described herein when administered to a subject results in, e.g., increased weight gain in the subject by at least about 1.1-fold or more, including, e.g., at least about 2-fold at least about 3-fold, at least about 4-fold, at least about 5-fold, at least about 6-fold, at least about 7-fold, at least about 8-fold, at least about 9-fold, at least about 10-fold or more, as compared to increased weight gain observed without administration of any fucosylated oligosaccharide described herein.

An effective dose of a fucosylated oligosaccharide for the methods described herein can be comparable (e.g., within 10%) to the level present in human milk. In some instances, an effective dose of a fucosylated oligosaccharide for the methods described herein can be higher, e.g., at least 10% higher (including at least 20%, at least 30%, at least 40%, at least 50%, at least 60%, at least 70%, at least 80%, at least 90%, or higher), than the level present in human milk. In some instances, an effective dose of a fucosylated oligosaccharide for the methods described herein can be higher, e.g., at least 1.1-fold higher (including at least 1.5-fold, at least 2-fold, at least 3-fold, at least 4-fold, at least 5-fold, or higher), than the level present in human milk. A physician in any event may determine the actual dosage which will be most suitable for any subject, which will vary with the age, weight and the particular disease or disorder to be treated or prevented. For example, an effective dose of a fucosylated oligosaccharide can be administered to any of the subjects described herein daily, every 2 days, every 3 days, or longer over a period of time, e.g., at least 1 week, at least two weeks, at least three weeks, at least four weeks, at least 2 months, at least 3 months, or longer, or until a desirable weight gain is attained in the subject.

In some embodiments, an effective amount of the above-described synthetic composition (e.g., pharmaceutical or food composition) is be administered to a subject (e.g., a human infant) orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions, liquids, and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an aqueous phase and combined with emulsifying or suspending agents. If desired, certain sweetening, flavoring, or coloring agents can be added. A nasal aerosol or inhalation composition can be prepared according to techniques well known in the art of pharmaceutical formulation.

III. Kits for Use in Increasing Weight Gain

The present disclosure also provides kits for use in increasing weight gain in a subject who fails to gain weight normally or who loses weight abnormally. Such a subject includes, but is not limited to, a premature infant, a subject who has undergone a surgery (e.g., an intestinal surgery or a bone marrow transplantation), or a subject who is suffering from undernutrition. Such kits can include one or more containers comprising one or more fucosylated oligosaccharides (e.g., those described herein) and/or glycoconjugates thereof, or one or more synthetic compositions comprising one or more fucosylated oligosaccharides (e.g., those described herein) and/or glycoconjugates thereof. In some embodiments, the kit can further include one or more containers comprising one or more active agents (e.g., therapeutic agents), nutrients, vitamins, minerals, etc. In some embodiments, the kit can further include a carrier solution (e.g., water, or a buffered solution) for reconstituting, dissolving, or resuspending solid, gel, or powder fucosylated oligosaccharides therein, prior to administration to a subject in need thereof. In some embodiments, the kit can further include components of an FUT2 assay to determine if a subject is FUT2 positive or FUT2 negative.

In some embodiments, the kit can comprise instructions for use in accordance with any of the methods described herein. The included instructions can comprise a description of administration of the compositions described herein for increasing weight gain in a subject in need thereof. The kit may further comprise a description of selecting an individual suitable for the methods described herein based on identifying whether that individual is, e.g., a premature infant, a subject who has undergone a surgery (e.g., an intestinal surgery or a bone marrow transplantation), or a subject who is suffering from undernutrition.

The instructions relating to the use of the compositions described herein generally include information as to dosage, dosing schedule, and route of administration for the intended use. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for increasing weight gain. The label or package insert can also identify a target population, e.g., premature infants, subjects who have undergone a surgery (e.g., an intestinal surgery or a bone marrow transplantation), or subjects who are suffering from undernutrition. Instructions may be provided for practicing any of the methods described herein.

The kits described herein are in suitable packaging. Suitable packaging includes, but is not limited to, vials, bottles, jars, flexible packaging (e.g., sealed Mylar or plastic bags), and the like. Also contemplated are packages for use in combination with a specific device, such as an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Use of 2'-fucosyllactose (2'-FL) to Improve Catch-Up Growth in Infants and Young Children after Growth Faltering Background:

Preterm infants tend to demonstrate poor weight gain during hospitalization (as measured by Z-score, which indicates their expected weight for age and gender). Similarly, after intestinal surgery, infants tend to lose weight as well as have poor weight gain post-operatively. An important nutritional goal is to achieve catchup growth to approximate their starting weight for age Z-score. The study herein reports the novel findings that the human milk oligosaccharide 2'-FL, a trisaccharide found in the milk of FUT2 positive ("secretor") mothers provides a growth recovery (catch up growth) benefit in a mouse model and in preterm infants <29 weeks gestational age.

Study 1: Intestinal Resection Mouse Model

Figure 2:
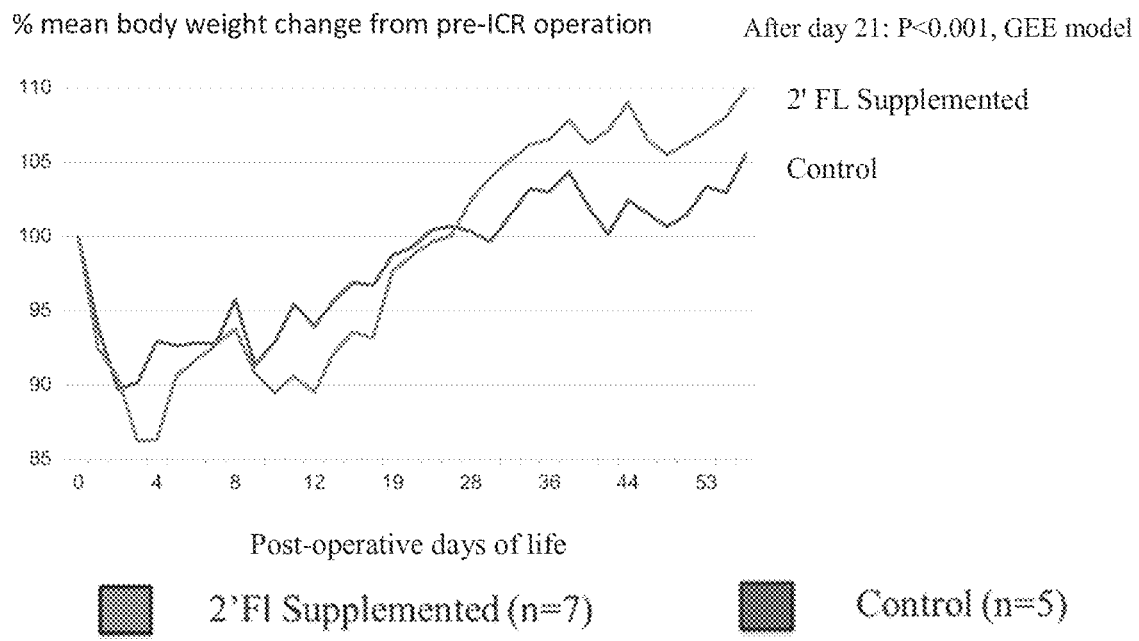
FIG. 2 is a graph showing growth in post-operative control and 2'FL-fed mice.

Study design: In a study illustrated in FIG. 1, an experiment of intestinal resection in a mouse model found that administration of 2.5 g/day of 2'-FL improved growth (FIG. 2).

Study 2: Growth in Preterm Infants <29 Weeks Gestational Age

Figure 3:
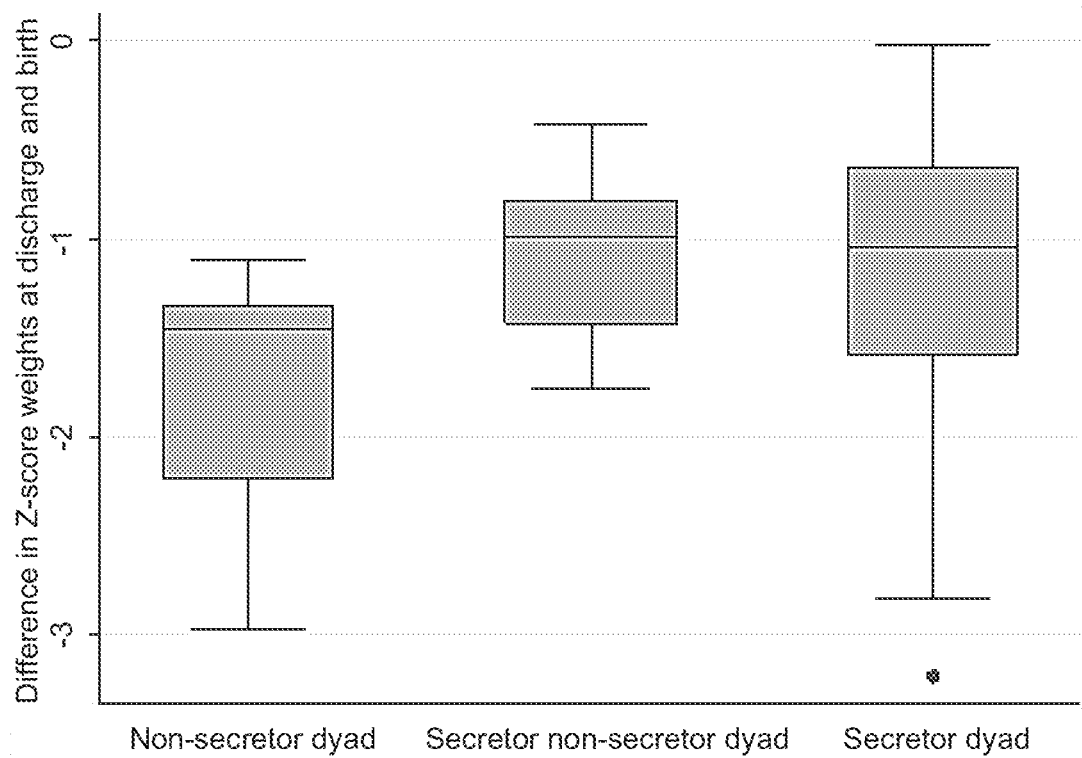
FIG. 3 is a graph showing difference in Z-score weights at discharge and birth in non-secretor dyad, secretor-non-secretor dyad and secretor dyad.

Human evidence of infant growth with 2'FL was found from clinical observation of preterm neonates. In 68 infants who were less than 29 weeks GA and 75% breastfeeding for the first 4 weeks of postnatal life, and mother-infant pairs were both non-secretors, infants had significantly less catch-up growth than infants of mother-infant preterm pairs in whom one or both were secretors. Non-secretor breastfeeding dyads had a greater Z-score loss from birth to hospital discharge (of −0.59, SE=0.24, p=0.016) compared to the secretor dyads, accounting for antibiotic use and gestational age at delivery (excluding necrotizing enterocolitis, death or sepsis) (FIG. 3 and Table 3).

TABLE 3

| independent variables | Discharge weight Z-score, Beta coefficient (SE) | p-value |
| --- | --- | --- |
| Non-secretor dyad | −0.59 (.24) | 0.015 |
| BW Z-score | −0.66 (.14) | <0.001 |
| Less than 26 weeks GA | 0.71 (.06) | <0.001 |

Figure 4:
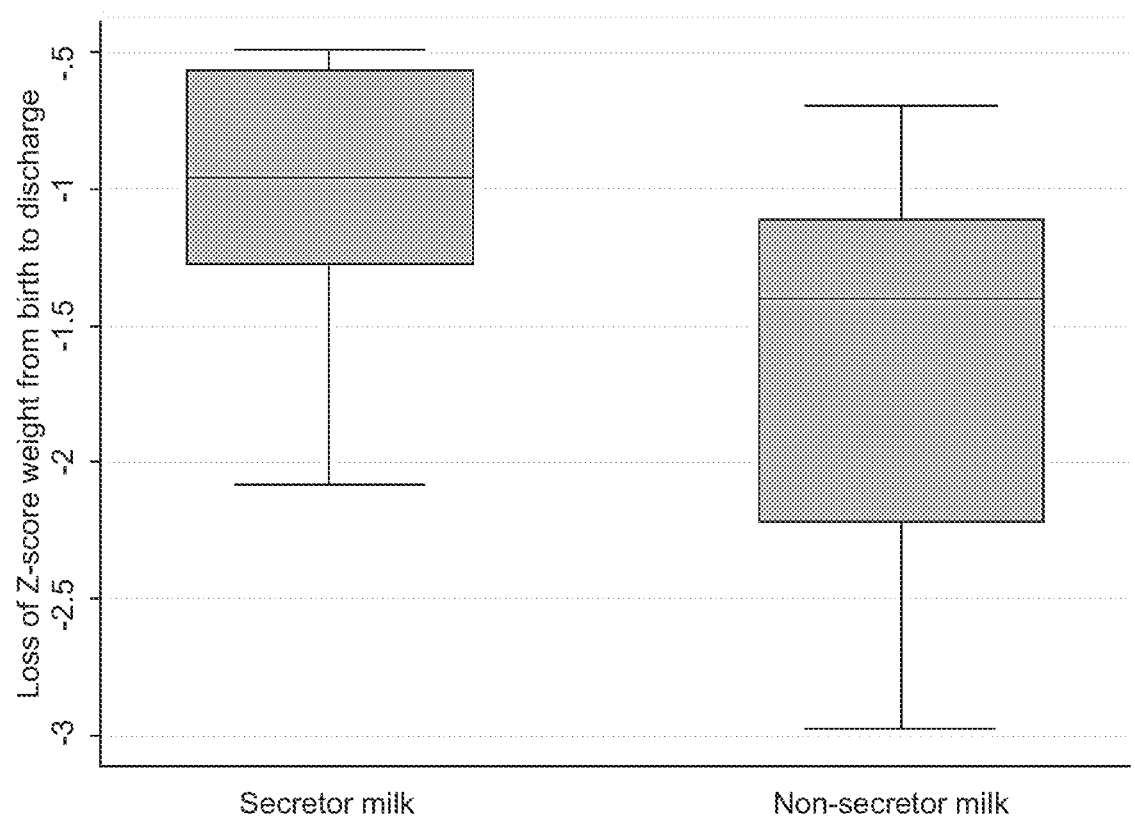
FIG. 4 is a graph showing the loss of Z-score weight from birth to discharge in preterm infants who received secretor milk versus those who received non-secretor milk.

When only preterm infants who are non-secretor or low H phenotype were examined, and therefore lack endogenous H antigen in their intestinal tract, there was greater catch-up growth in those who received "secretor" milk, which contains 2'-FL, than in those who received "non-secretor milk," which does not include 2'-FL (p=0.15). As shown in FIG. 4, in the 12 infants who were FUT2—(low and non-secretor and therefore lacked endogenous H antigen), it was shown that mother's milk containing 2'-FL ("Secretor milk", left box in FIG. 4) was associated with greater catch up growth or lesser Z-score weight loss during hospitalization. Secretor milk refers to milk obtained or derived from secretor mothers, e.g., mothers with a functional FUT2 gene, or mothers who are able to produce a fucosylated oligosaccharide (e.g., 2'-FL) in secretions including breast milk. Non-secretor milk refers to milk obtained or derived from non-secretor mothers, e.g., mothers who are negative for FUT2 gene, or mothers whose FUT2 gene is mutated and becomes dysfunctional, or mothers who are not able to produce a fucosylated oligosaccharide (e.g., 2'-FL) in secretions including breast milk.

Figure 5:
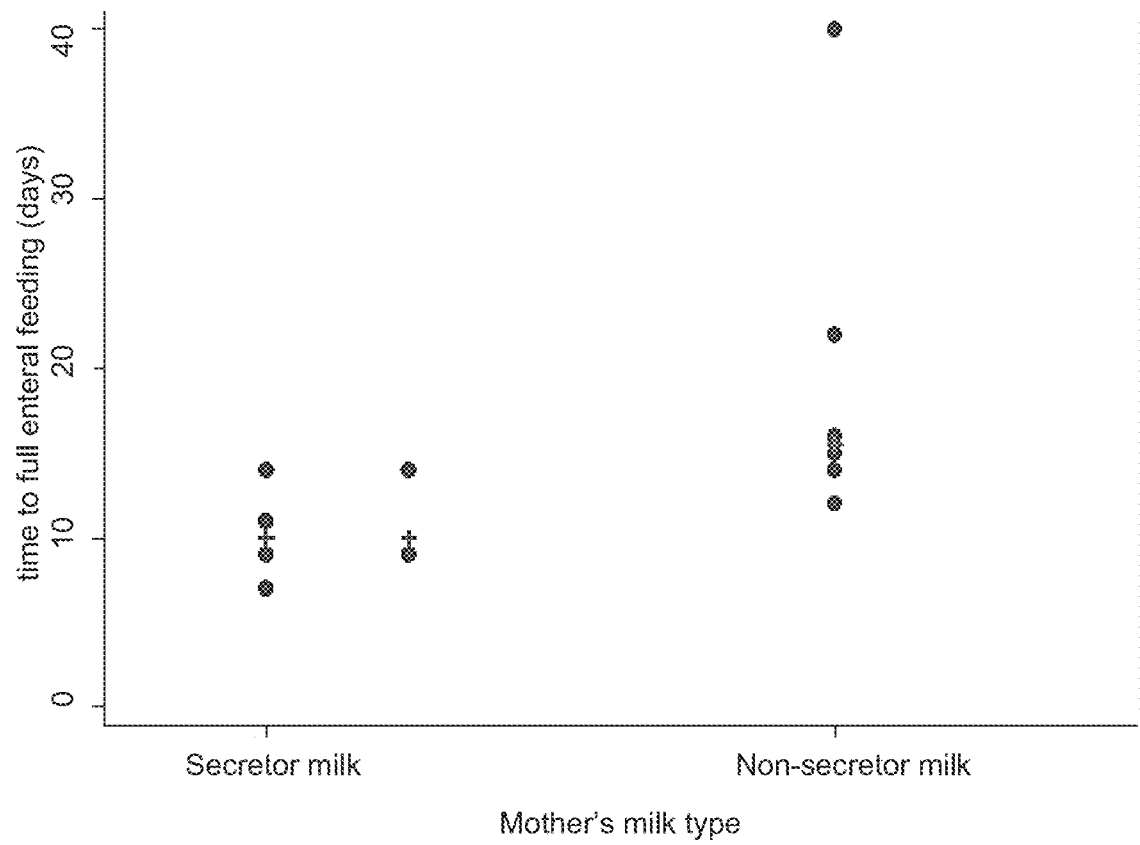
FIG. 5 is a graph showing the time to full enteral feeding in infants who received secretor milk versus those who received non-secretor milk.

In additional to infant growth measures, "secretor milk" may have another related advantage to gut health and development—fewer days to full enteral feeding. As shown in FIG. 4, in 12 low and non-secretor infants who were 75% breastfed (free of NEC, sepsis and death, P=0.015, KW test), the time to full enteral feeding was significantly better if the mother's milk was "secretor", therefore containing 2'-FL (FIG. 5).

Example 2. 2'-FL Improves Weight Gain

This example provides experimental data obtained from further studies showing the effectiveness of 2'FL in improving weight gain, e.g., improvement of long-term weight profile following intestinal resection and improvement of sustained adaptive responses to intestinal resection.

Adaptive Responses to Intestinal Resection

Figure 6:
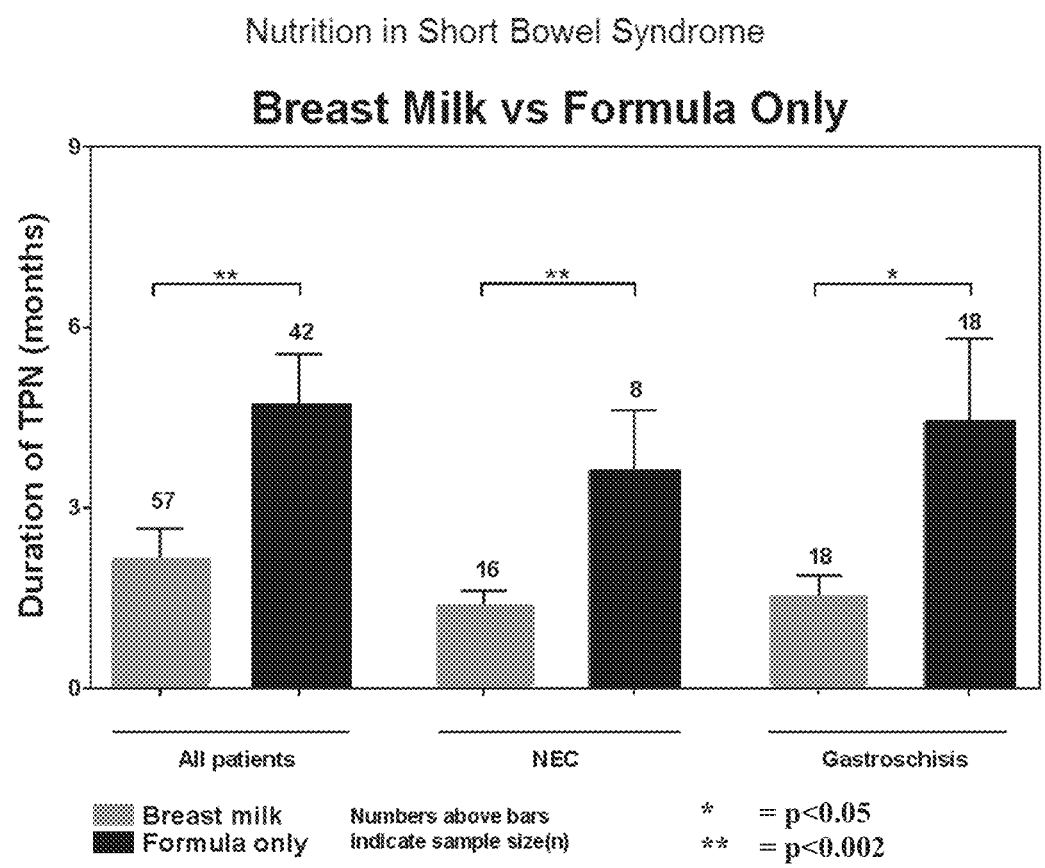
FIG. 6 is a graph showing duration of total parenteral nutrition (TPN) for patients (e.g., infants) fed with breast milk vs. milk formula without 2' FL.

Polymeric or monomeric milk formula can be used for infants with short bowel syndrome. However, a clear benefit from human milk comprising 2' FL has been observed (FIG. 6). Specifically, infants fed human milk achieved enteral autonomy sooner with less morbidity than those fed formula. In fact, among 99 infants requiring parenteral nutrition for longer than 1 week, those fed human milk required parenteral nutrition for significantly less time than those fed formula.

Figure 7:
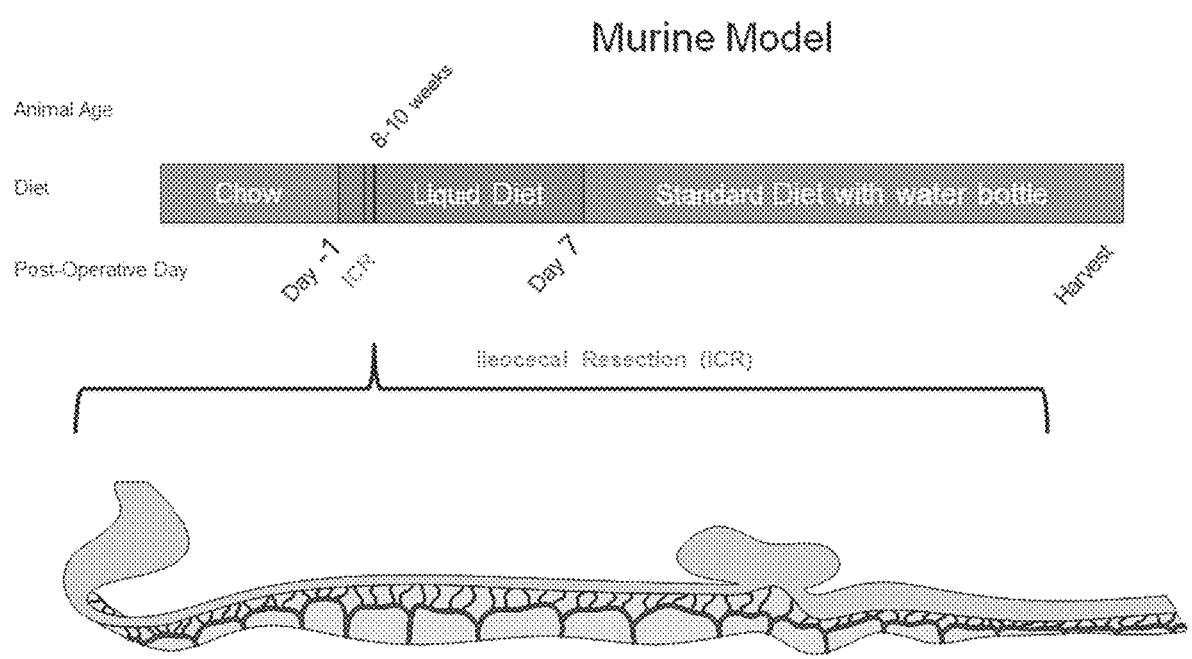
FIG. 7 is a diagram showing a study design of adaptation following intestinal resection in a murine model.
Figure 8:
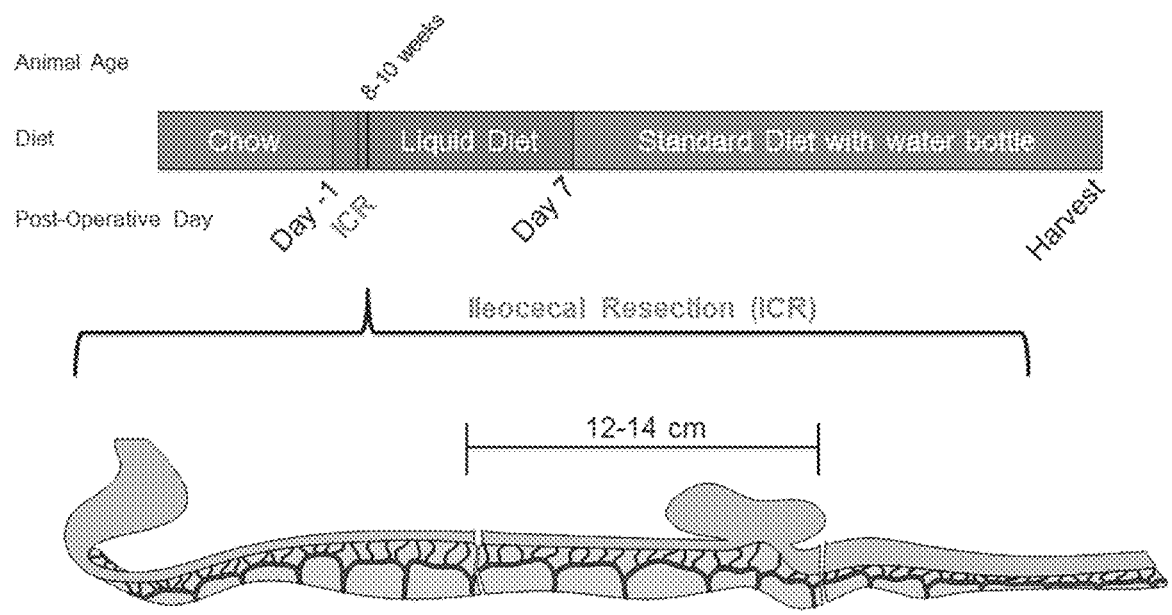
FIG. 8 is a diagram showing identification of the ileocecal junction for ileocecal resection. Approximately 12-14 cm of the intestine is resected in a murine model.
Figure 9:
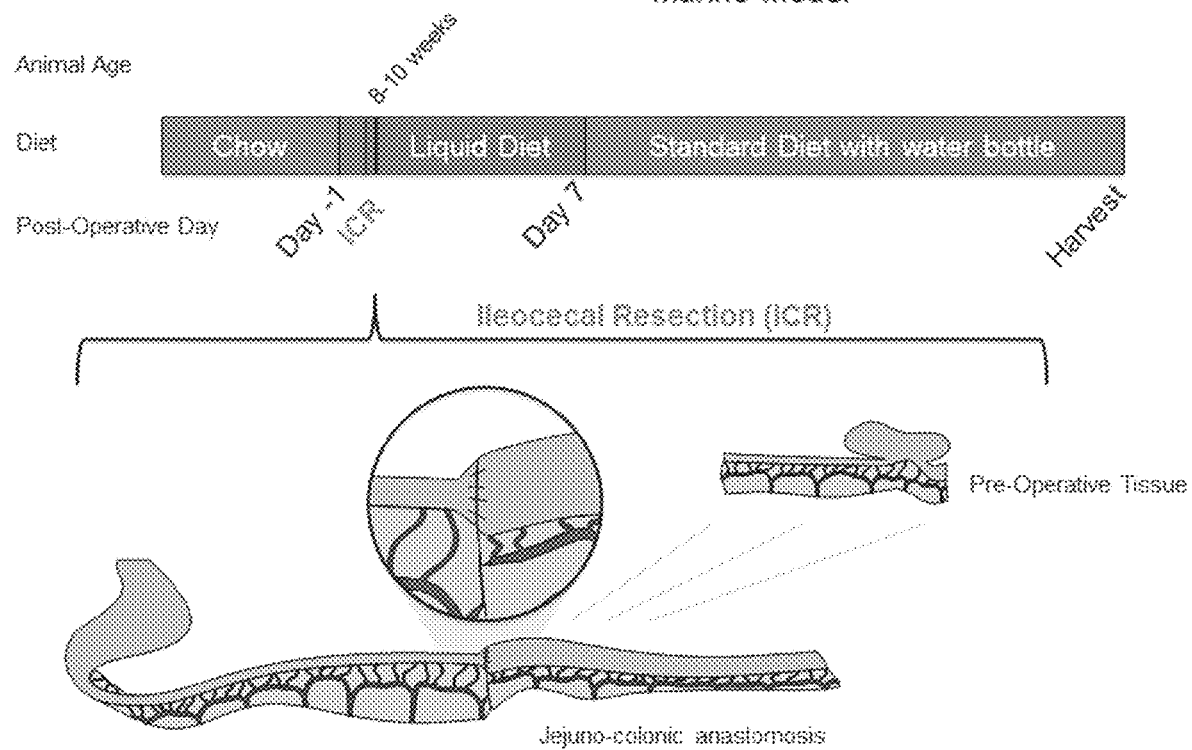
FIG. 9 is a diagram showing that intestinal continuity is restored by end-to-end anastomosis in a murine model. The mice receive one dose of intraperitoneal broad-spectrum antibiotics.

A mouse model of adaptation following intestinal resection was previously reported. Under the aid of an operating microscope and utilizing sedation with 2% isoflurane, a midline incision was made in the bowel and the bowel was eviscerated (FIG. 7). FIG. 8 shows the identification of the ileocecal junction and approximately 12 cm of ileum and cecum were resected. Intestinal continuity was restored by end-to-end anastomosis and the abdomen of mice was closed (FIG. 9). The mice received one dose of intraperitoneal broad-spectrum antibiotics.

Figure 10:
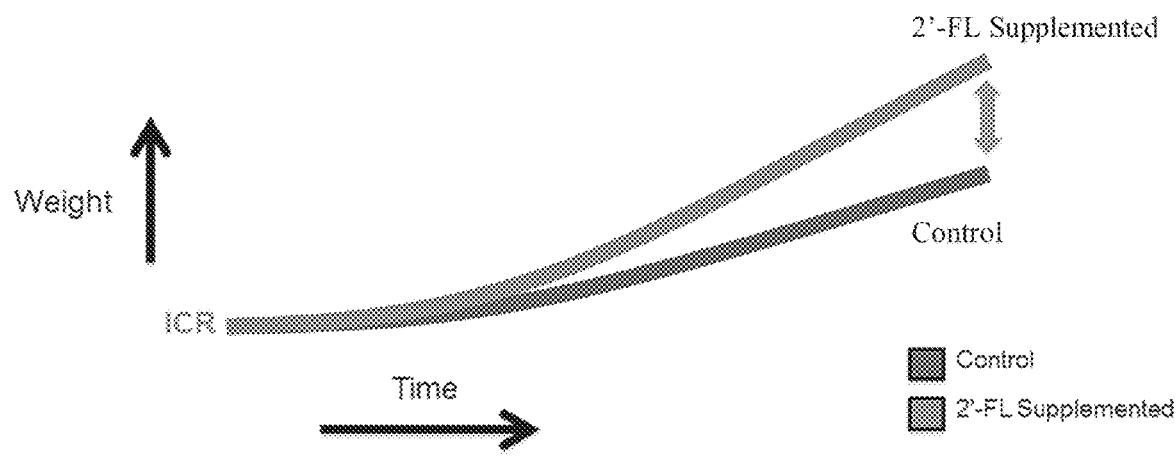
FIG. 10 is a schematic diagram showing that 2'FL supplementation can result in improved long-term weight profile following intestinal resection.

To determine whether 2'Fl would improve the adaptive response (FIG. 10), an improved long-term weight change profile with 2'Fl supplementation was demonstrated. Though histologic findings presumed to stimulate the gross adaptive response are most robust during the acute phase, the histologic difference between control and experimental groups in the late phase was characterized. Changes in the microbial communities with 2'-Fl supplementation were also characterized.

Figure 11:
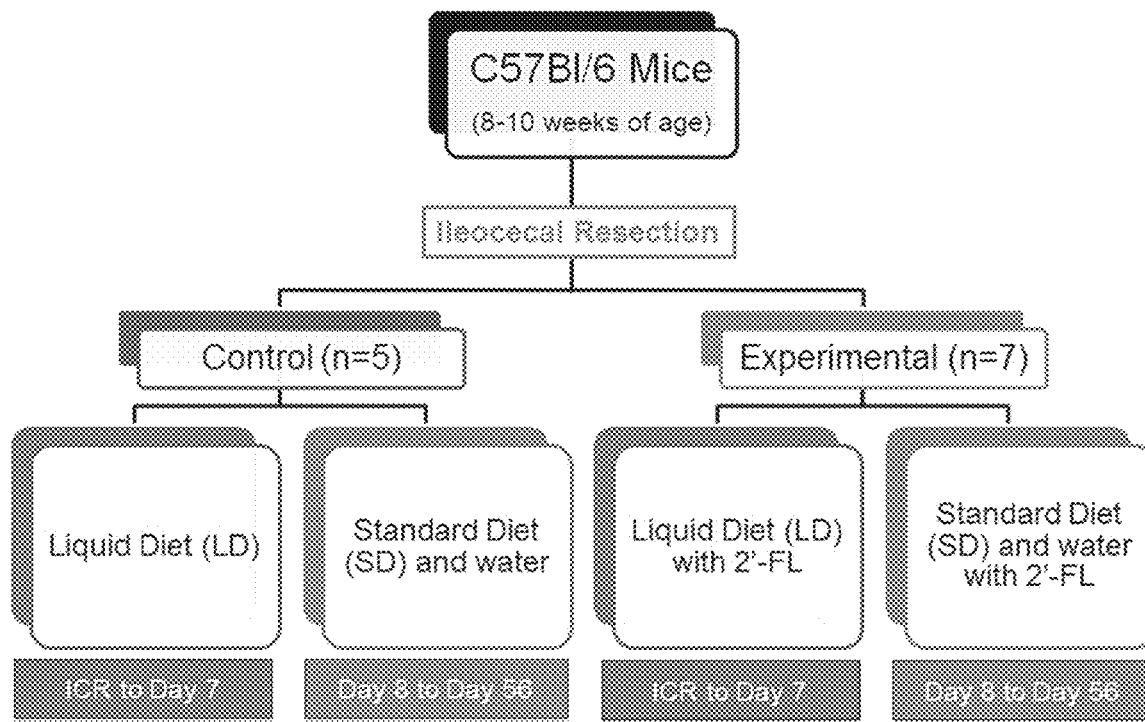
FIG. 11 is a diagram of a study design used in Example 2. 2'FL was added to both liquid diet (LD) and standard diet (SD) with water to achieve a final concentration of 2½ grams per liter.

In particular, C57 Black 6 mice of 8 to 10 weeks in age were subjected to ileocecal resection (FIG. 11). 5 animals were carried to post-operative day 56 in the usual fashion. Seven animals were carried to the same time point but supplemented with 2'Fucosyllactose. 2'FL was added to both liquid diet (LD) and standard diet (SD) with water to achieve a final concentration of 2½ grams per liter. All animals were weighed once daily during the first week then once every other day thereafter.

Figure 13:
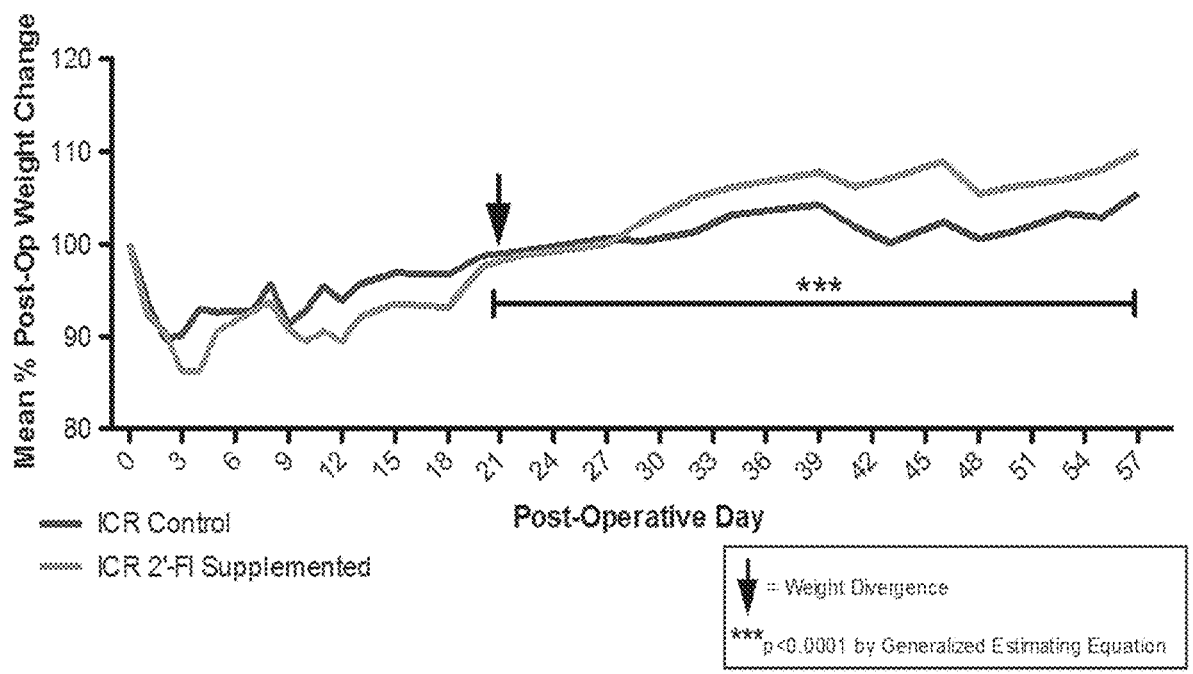
FIG. 13 is a graph showing the difference in weight change after ICR in control subjects vs. subjects supplemented with 2' FL. Ploted lines represent mean weight per group. A significant difference was observed on and beyond postoperative day 21.

It was found that 2'FL supplementation led to an improved late-term weight-gain profile following resection (FIG. 13). Using a generalized estimating equation, differences in weight change between 2' FL supplemented and control groups were found to reach significance on and beyond post-operative day 21 (FIG. 13). Both groups displayed a similar weight change profile acutely after resection. The improved weight change profile is one of the important outcome measures when evaluating the adaptive response in this model.

Figure 14:
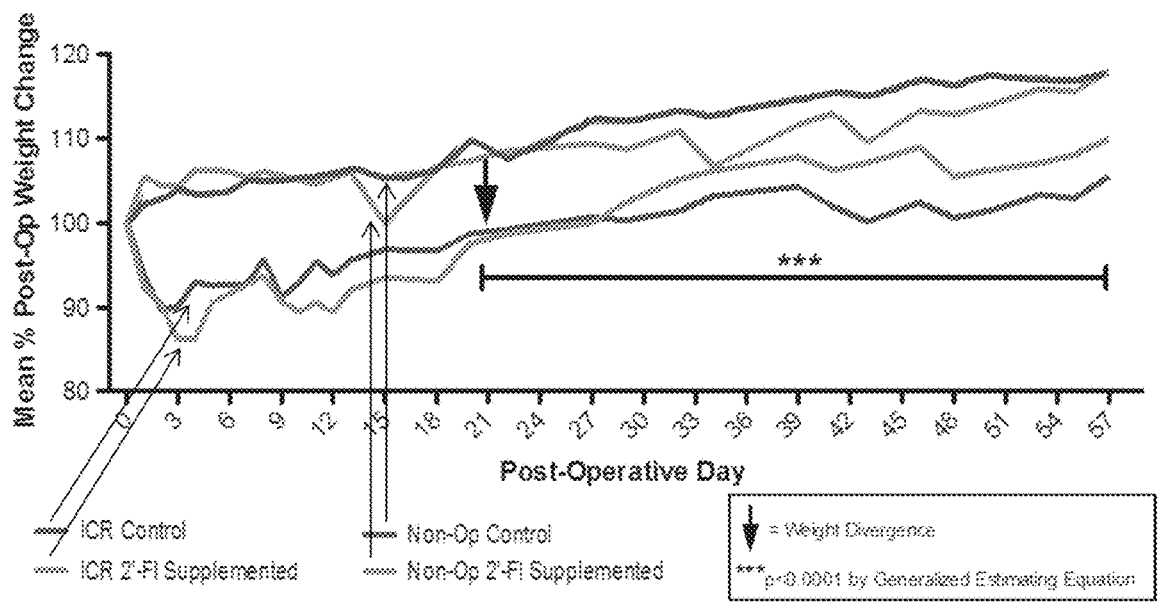
FIG. 14 is a graph showing the mean percent weight changes in non-operative subjects and post-operative subjects (after ICR) when they were supplemented with or without 2' FL. No significant difference was shown in subjects without the insult of intestinal resection.

An experiment adding non-operative groups to investigate the impact of 2'-Fl on weight without the insult of intestinal resection was also performed. The role of late 2'-FL-supplementation in this model was investigated, providing the oligosaccharide beginning at 14 days after resection to better simulate real-world conditions. Furthermore, when plotted against non-operative experiment data, no significant difference in the weight change between control and 2' FL supplemented groups without the insult of intestinal resection (FIG. 14).

Figure 12:
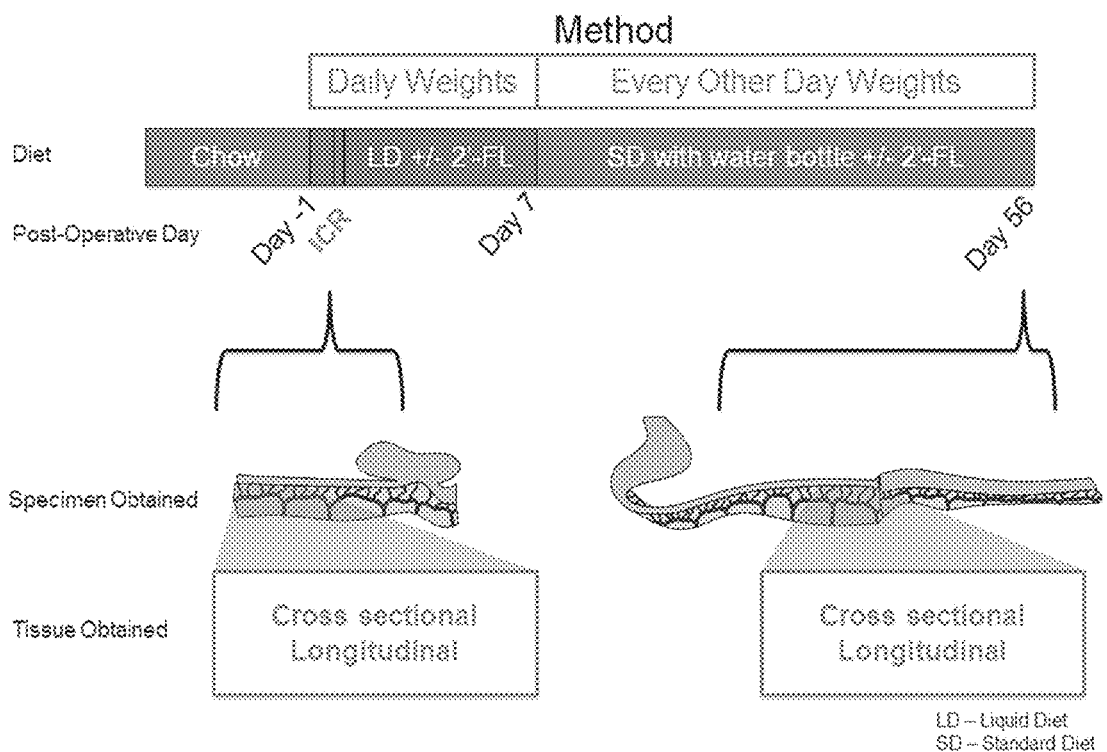
FIG. 12 is a diagram showing, at the time of resection and 56 days after ileocecal resection, the region from which tissue was obtained for histologic examination.
Figure 15:
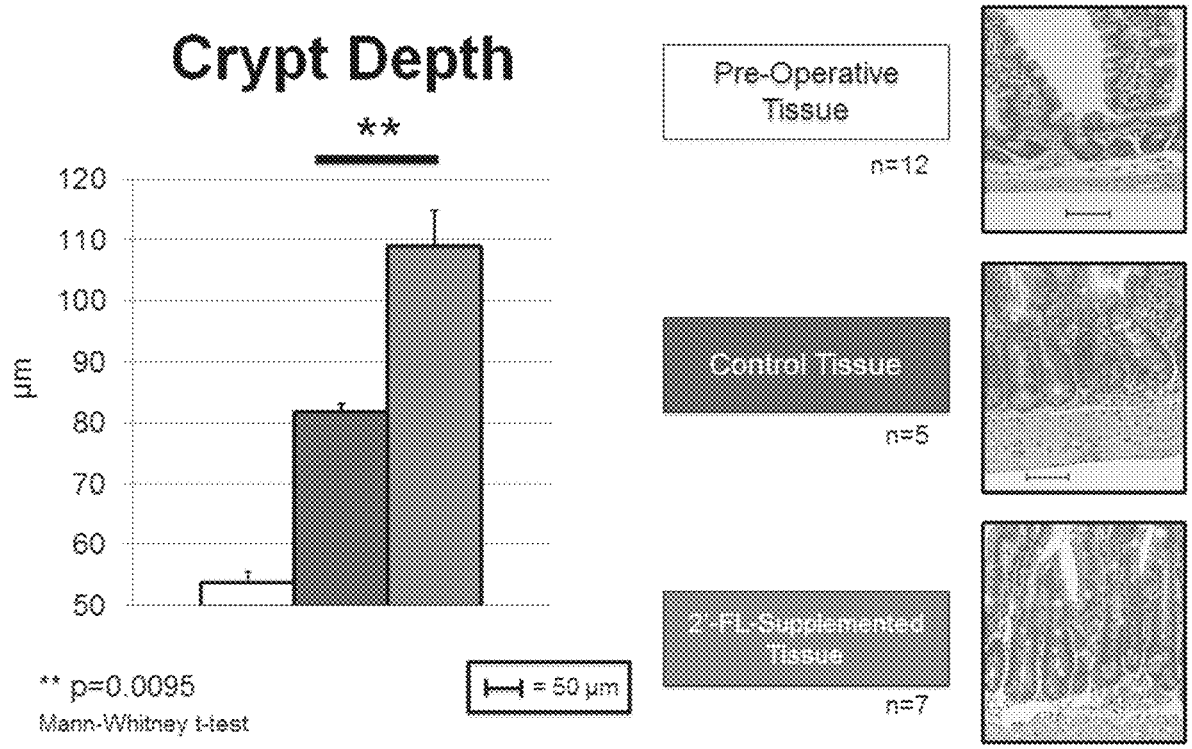
FIG. 15 shows histologic change in tissue after ICR. Even at 8 weeks post-operation, crypt depth was significantly greater in the 2' Fl supplemented animals when compared to controls (no 2' FL supplementation). Crypts of both control and 2' FL-supplemented groups were deeper than those of pre-operative tissue.
Figure 16:
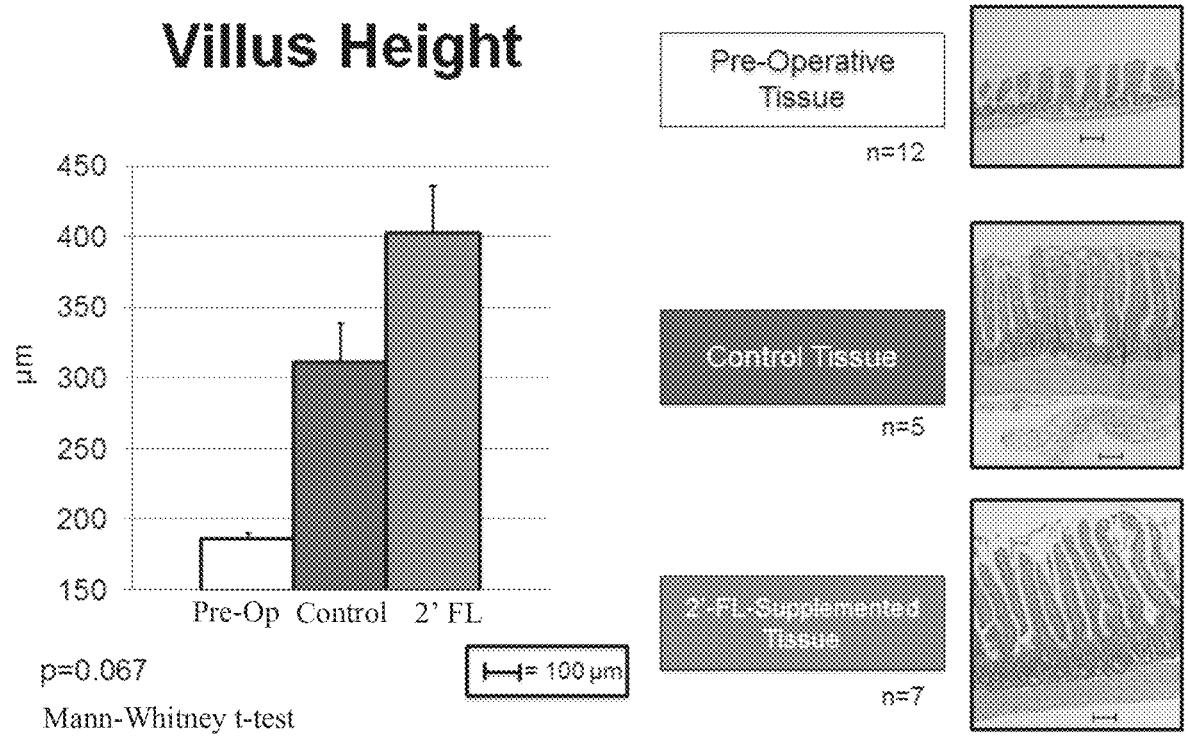
FIG. 16 shows that the villi of animals supplemented with 2'-Fl appeared longer than those of the control animals, after ICR operation. Both post-operative groups (control and 2' FL supplemented groups) displayed longer villi than there pre-operative tissue.
Figure 17:
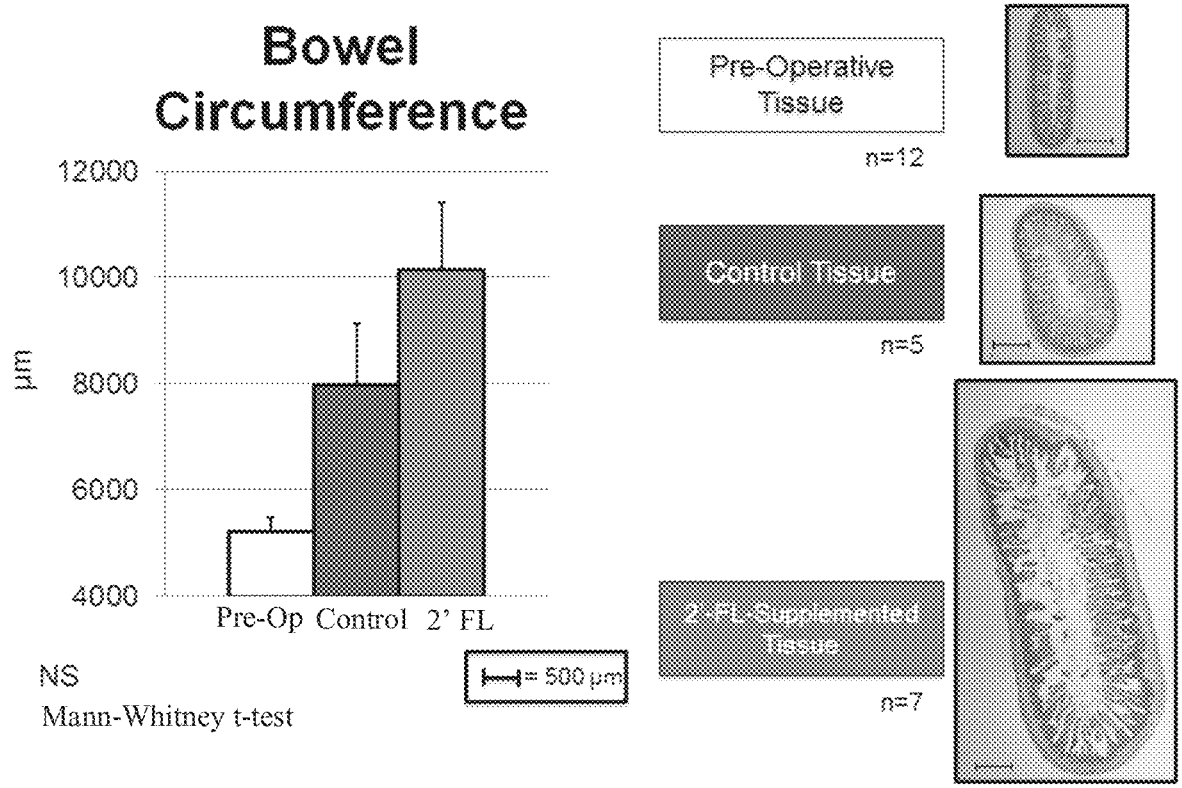
FIG. 17 shows bowel circumference following ICR was increased, but no significant difference between post-operative groups was found.

At the time of resection, tissue was obtained to prepare for histologic examination (FIG. 12). No differences in measurements of villus height, crypt depth, and bowel circumference were found at the time of resection. After resection, the animals were supported to post-operative day 56 and sacrificed and their small bowel were harvested for histology. Even at 8 weeks post-operation, crypt depth was significantly greater in the 2'FL supplemented animals when compared to post-operative controls (FIG. 15). Crypts of both post-operative control and 2' FL supplemented groups were deeper than those of pre-operative tissue. The villi of post-operative animals supplemented with 2'-FL appeared longer than those of the control post-operative animals (FIG. 16). Both post-operative groups displayed longer villi than there pre-operative tissue. Bowel circumference following ICR was increased but no significant difference between post-operative groups (control vs. 2' FL supplemented) was found (FIG. 17).

Figure 18:
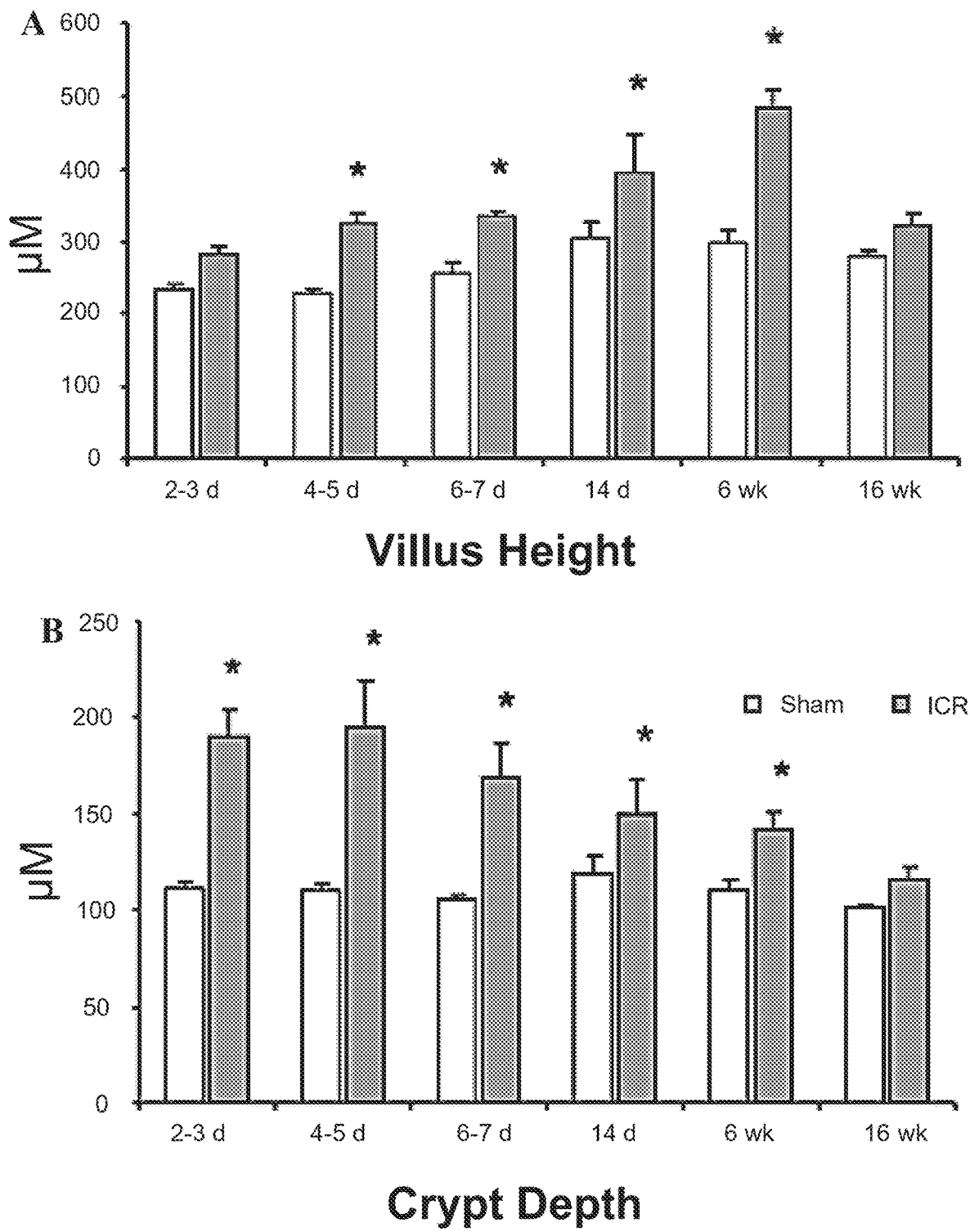
FIG. 18 shows comparison of histology markers from ileocecal resection (ICR) and sham animals. This figure shows the normal adaptive response to ICR in mice. Specifically, it shows that ICR-induced histologic change in villus height (Panel A) and crypt depth (Panel B) approaches baseline by 6 weeks after ICR. The histologic changes with 2'-FL supplementation, e.g., shown in FIGS. 15-17, indicate that 2'-FL improves and lengthens this adaptive response.

FIG. 18 shows that 2'-FL improves or sustains adaptation response to ileocecal resection. Histologic change was observed when 2'-FL improved late-term weight change when compared to no supplementation. Panel A of FIG. 18 shows villus height and Panel B of FIG. 18 shows crypt death. Taken together, these data indicate that 2'fucosyllactose improves the long term response to ileocecal resection.

Figure 19:
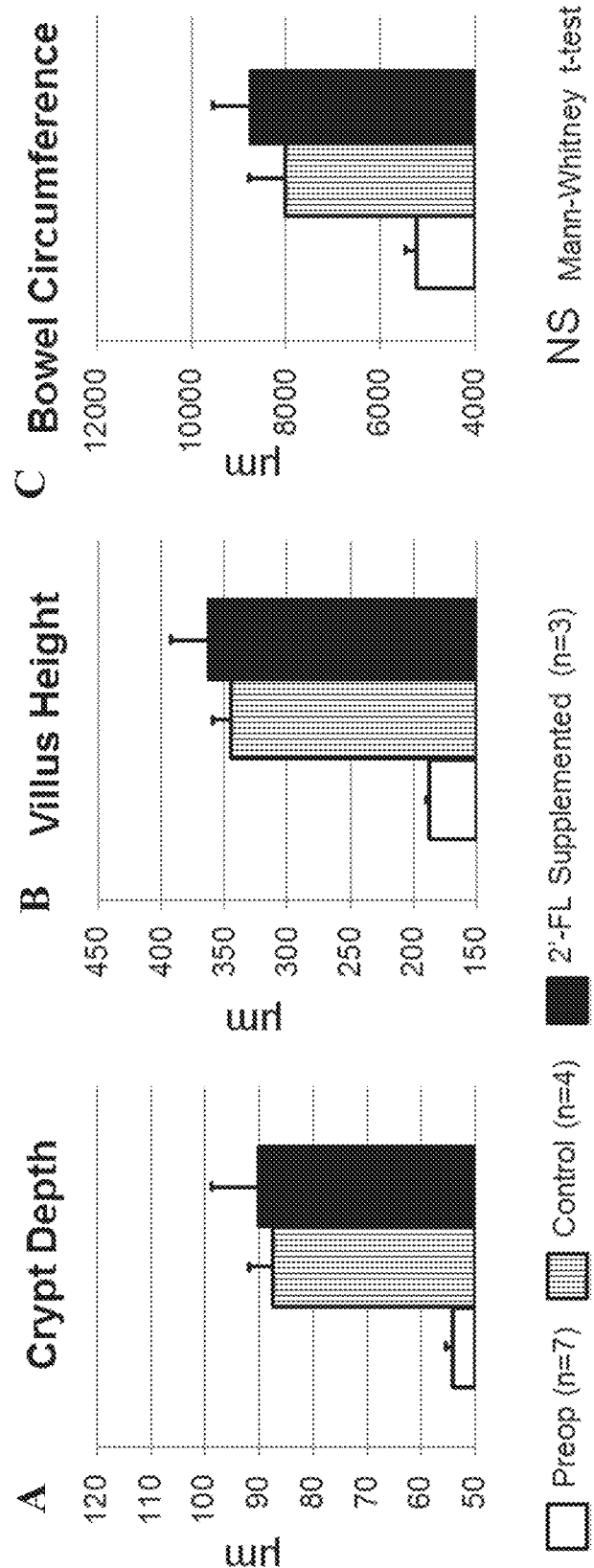
FIG. 19 is a series of graphs showing that 2'-FL did not alter histologic markers of adaptation at the point of weight divergence or 21 days post-ICR. Panel A shows crypt depth; Panel B shows villus height; and Panel C shows bowel circumference.
Figure 20:
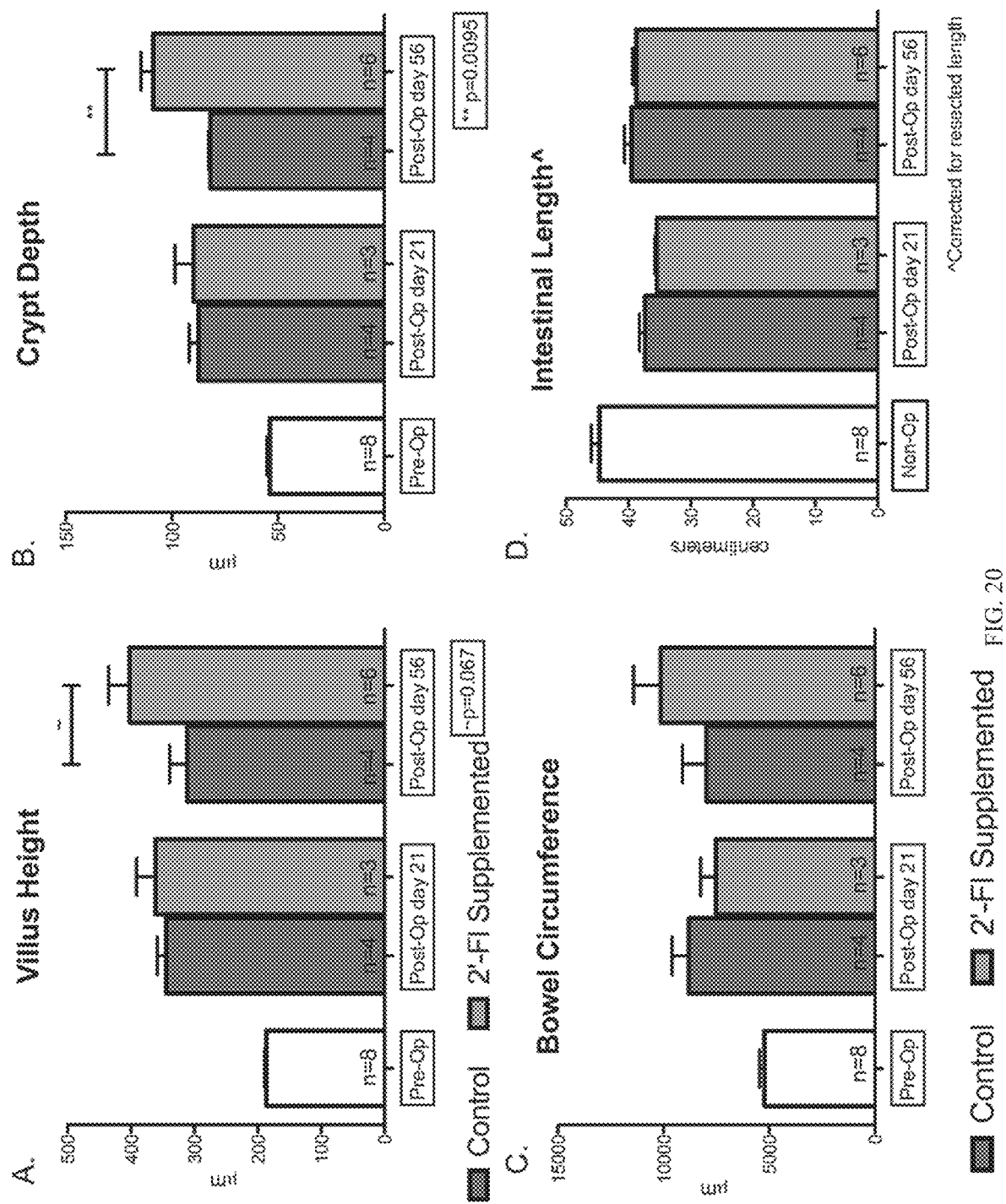
FIG. 20 is a series of graphs showing that 2'-FL sustained the acute increases in histologic markers of adaptation 21 days post-ICR Panel A shows villus height, Panel B shows crypt depth, Panel C shows bowel circumference, and Panel D shows intestinal length.

As significant differences in histologic measures were observed over a period of at least 6 weeks, it was sought to determine if a more drastic difference was observed at the point of weight divergence (e.g., as shown in FIG. 13, which shows ~21 days after ileocecal resection). Therefore, a similar experiment was performed at an endpoint of 21 days after ileocecal resection. It was found that 2'-FL did not alter histologic markers of adaptation at the point of weight divergence or 21 days post-ICR. As shown in FIG. 19, there was no difference in crypt depth (Panel A), villus height (Panel B), or bowel circumference (Panel C) at post-operative day 21. However, when the average histologic measure for each experimental group in the post-operative day 56 experiment is plotted alongside post-operative day 21 figures, it was found that 2'-FL-supplementation sustains the acute histologic response over a longer time period than as seen in the control group (FIG. 20, Panels A-D). This indicates an increased mucosal surface area in the 2' FL-supplemented animals at the late, but not early time point, also indicating that there may be a supplementary process responsible for the early difference in growth observed beginning at post-operative day 21.

Figure 21:
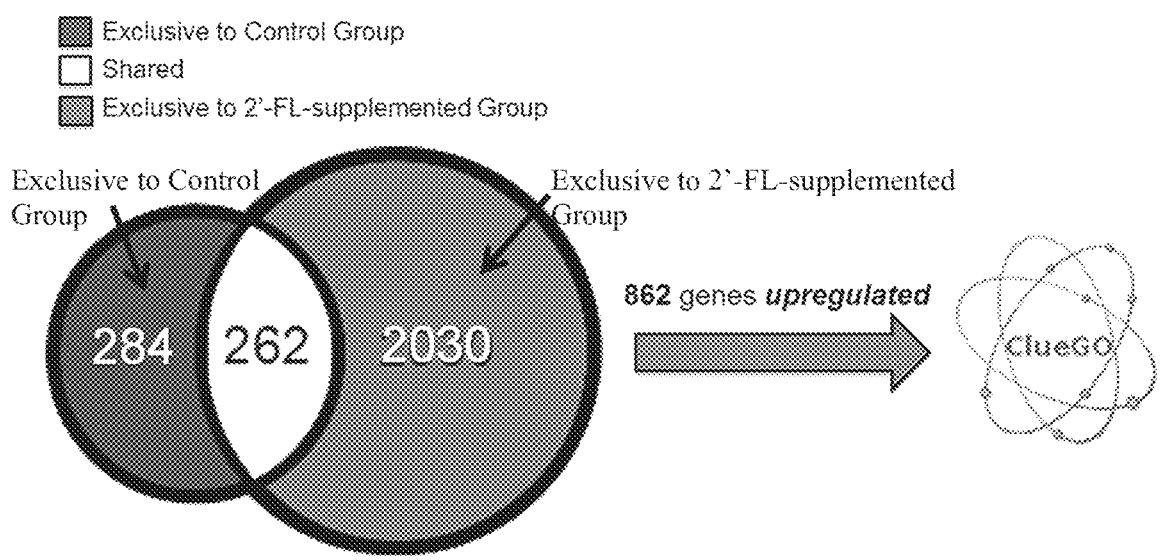
FIG. 21 is a diagram showing the transcriptional analysis of small bowel 56 days after ileocecal resection, baselined to pre-operative samples.
Figure 22:
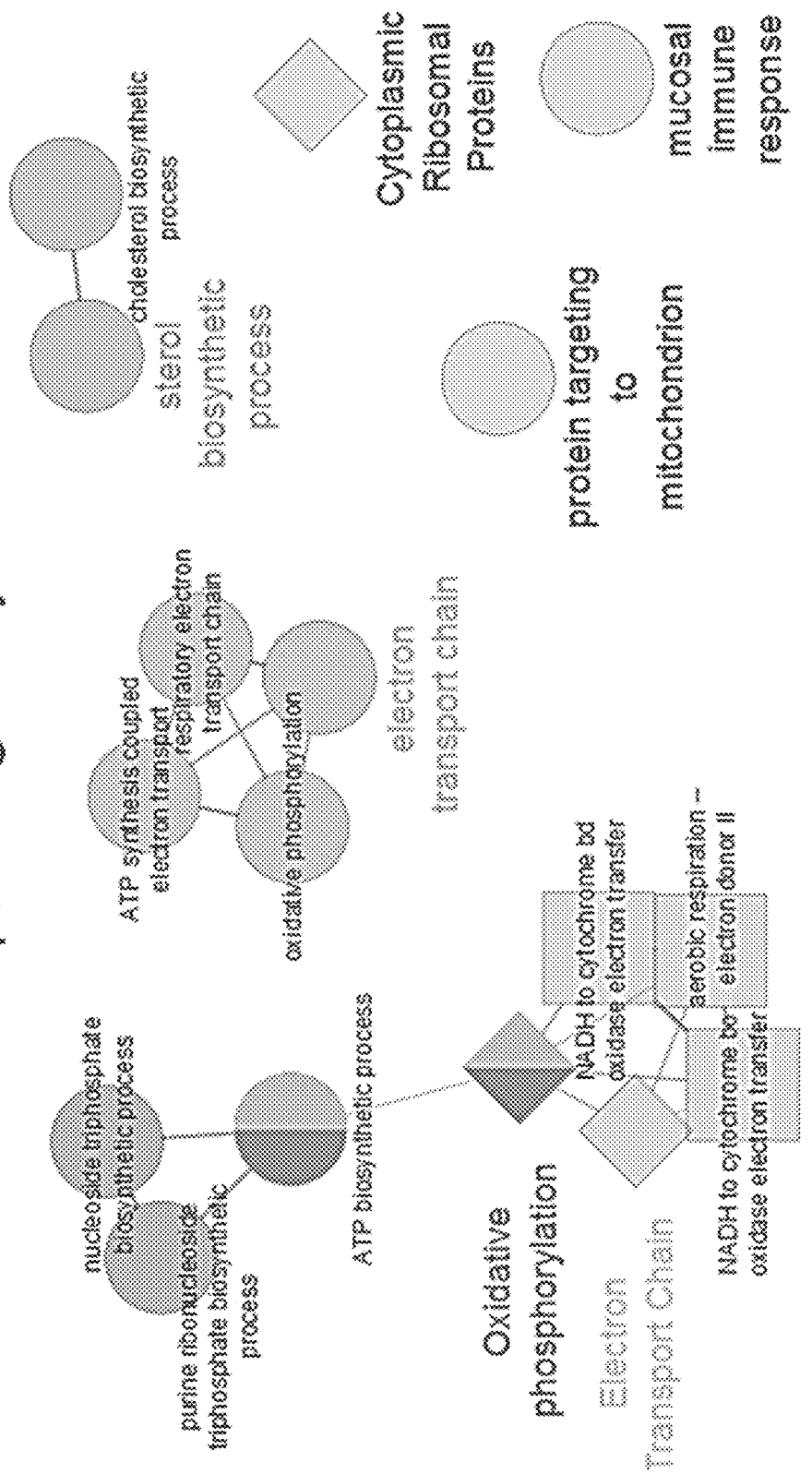
FIG. 22 is a series of diagrams showing all non-redundant gene ontologies and gene pathways discovered through the analysis as described in FIG. 21.

It was next sought to determine if 2'-FL may also shift the microbiome to one more adept at energy extraction, making available more energy for the intestinal mucosa. To this end, the microbiome and the intestinal transcriptome were analyzed. The transcriptional analysis of small bowel 56 days after ileocecal resection, baselined to pre-operative samples (FIG. 21) shows that of 2,576 genes differentially regulated among control and experimental groups, 2,030 genes were exclusive regulated by 2'-FL. 862 of these genes were upregulated. This gene list was analyzed using ClueGO, a Cytoscape plug-in designed to decipher functionally grouped gene ontology and gene pathway annotation networks. All non-redundant gene ontologies and gene pathways discovered through such an analysis are shown in FIG. 22. The results of the analysis supports increased energy harvesting by indicating a transcriptional push toward small bowel energy processing in the 2'-Fl-supplemented experimental group. Ontologies and pathways related to oxidative phosphorylation, electron transport, and cholesterol biosynthesis were discovered (FIG. 22).

Figure 23:
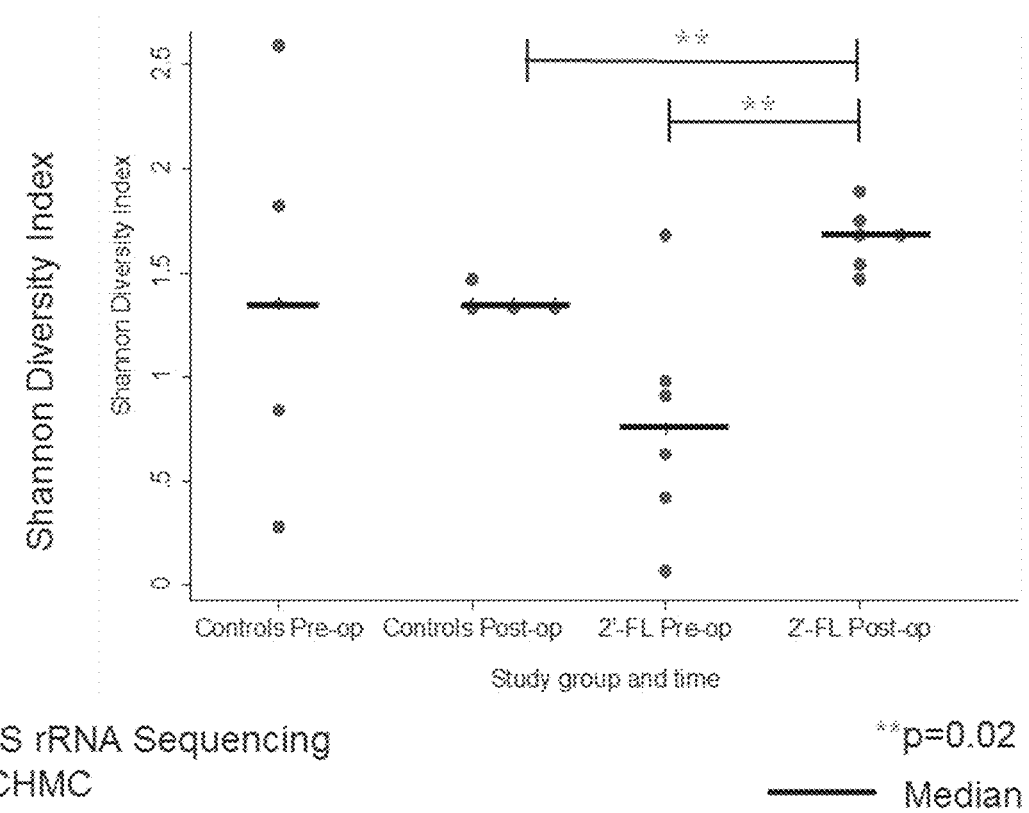
FIG. 23 is a graph showing microbiome analysis. 16S ribosomal RNA sequencing was used and microbiome diversity was evaluated with the Shannon diversity index.

16S ribosomal RNA sequencing was used and microbial diversity was evaluated with the Shannon diversity index. There was no difference in microbial diversity in pre-operative animals. However, there was a significant increase in microbial diversity in the 2'-FL supplemented post-operative group (FIG. 23). Microbial function can be also assessed, for example, using metagenomic sequencing or metatranscriptomics. Additionally, luminal short chain fatty acids can be quantified to elucidate the mechanism of the weight difference occurring prior to histologic difference.

Figure 24:
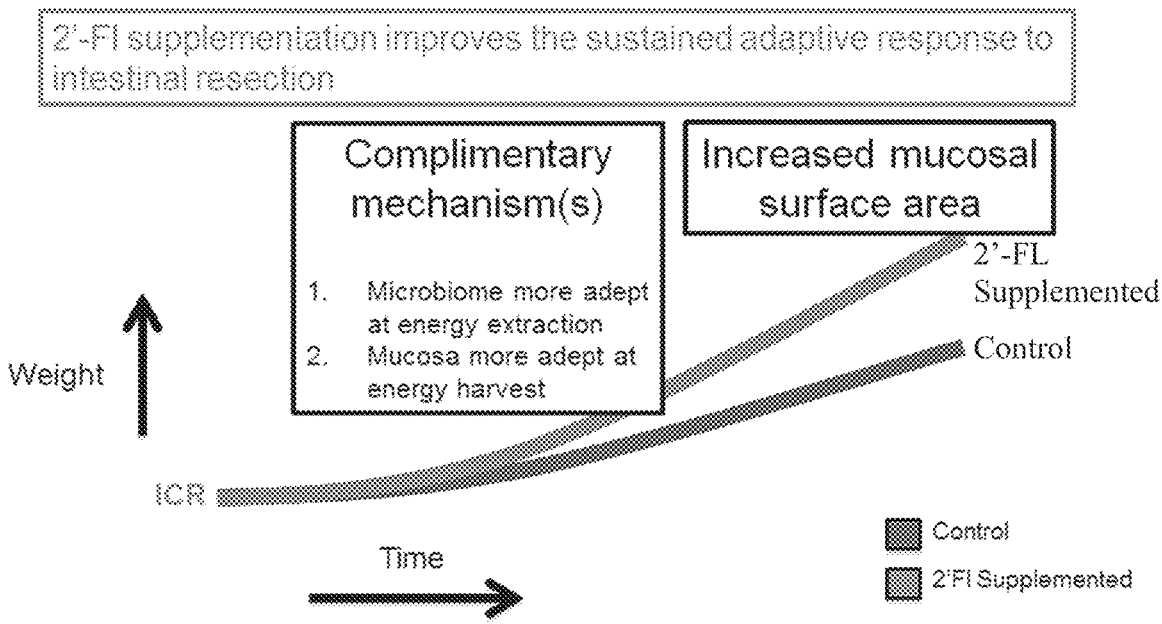
FIG. 24 is a schematic showing that 2'-Fl supplementation improves the sustained adaptive response to intestinal resection. Contemplated complementary mechanisms include, for example, a microbiome more adept at energy extraction and mucosa more adept at energy harvest. Increased mucosal surface area was also observed.

Taken together, 2'-FL supplementation improves the sustained adaptive response to intestinal resection. As shown in FIG. 24, other mechanisms may impart the early growth advantage seen beginning at 21 days. Without wishing to be bound by theory, complimentary mechanisms may be involved including a shift toward a microbiome more adept at energy extraction and a mucosa more adept at energy harvest.

Pre-Term Infant and Short Bowel Population Studies

Figure 25:
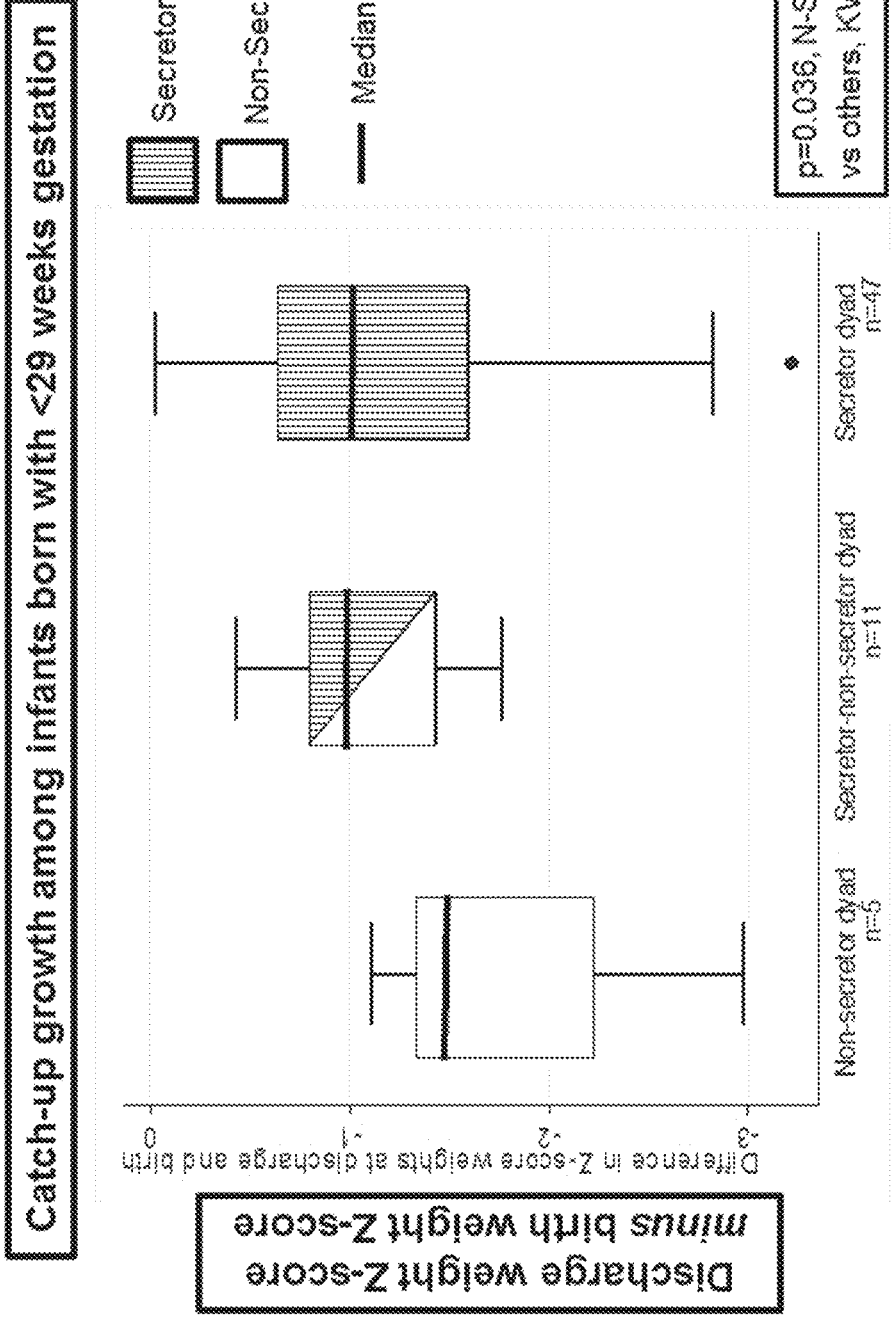
FIG. 25 is a graph showing that secretor status impacts neonatal outcomes, specifically catch-up growth among infants born with <29 weeks gestation.
Figure 26:
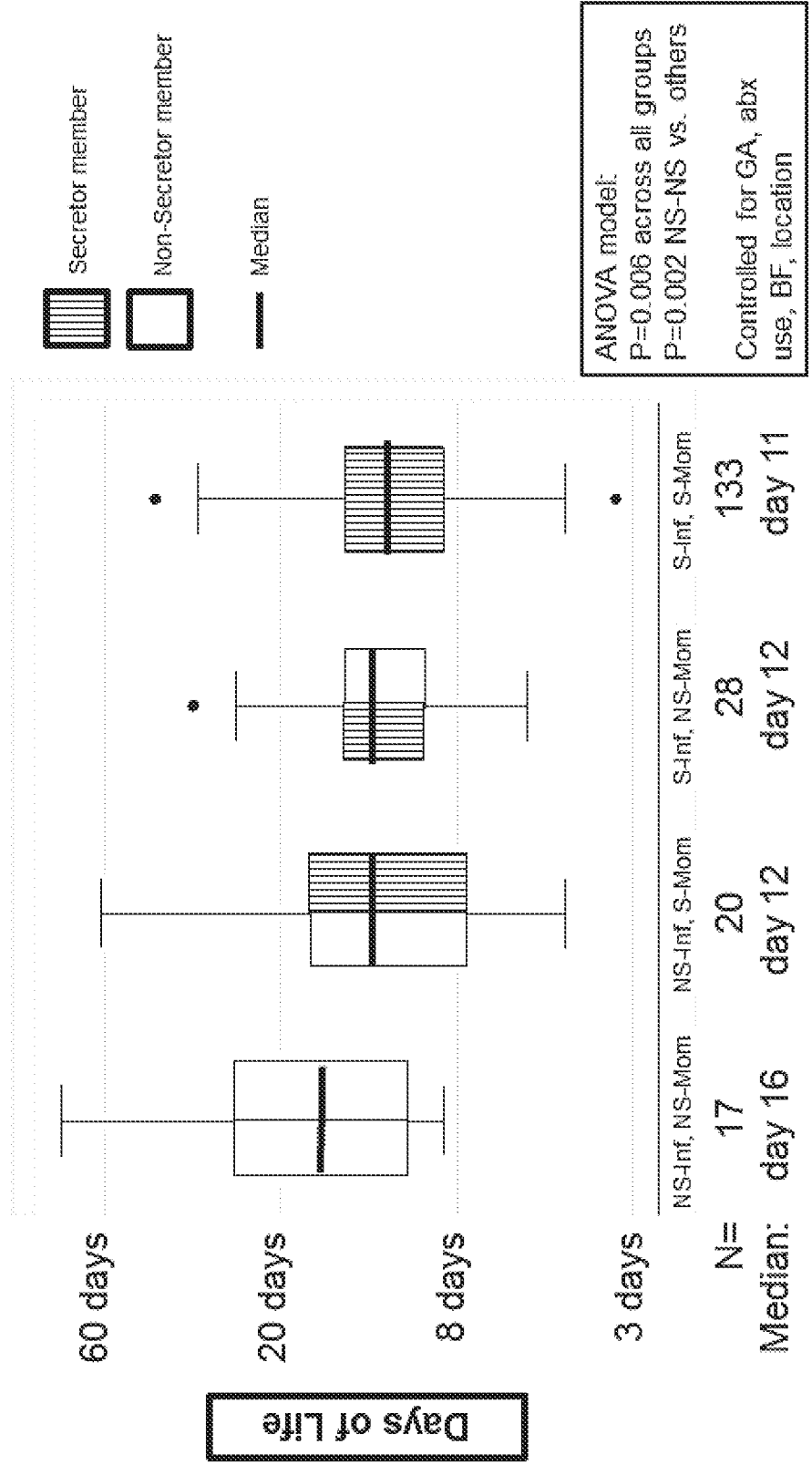
FIG. 26 is a graph showing the number of days to full enteral nutrition among infants born with <30 weeks gestation and different secretor status. NS-inf: Non-secretor infant; NS-Mom: Non-secretor mom; S-Inf: secretor infant; S-Mom: secretor mom.

FIG. 25 shows collected data on infants born very prematurely. Of those surviving to discharge, catch-up growth was the worst among non-secretor infants born to non-secretor mothers, the so-called non-secretor dyad. When both or even one of the pair are secretors of fucosylated glycans, those infants achieved better catch-up growth. FIG. 26 examined the time it took very premature infants to achieve full enteral nutrition. The Y axis indicates time to full enteral feeding in log scale. On the left of the graph in FIG. 26, the non-secretor dyad (NS-inf, NS-Mom) took significantly longer to wean to full enteral feeding than any of the dyad's containing a secretor member.

In summary, about 80% of the population fucosylate mucosal glycans, providing an additional energy source for commensal microbes. In animals, this fucosylation has been shown to improve the response to illness, stabilize the commensal microbiome, and provide fuel for a variety of bacterial taxa, some of which produce short chain fatty acids—fuel for intestinal epithelial cells. Further, it was found that secretor status impacts neonatal health outcomes specifically relating to intestinal function during a period of development similar to adaptation. Thus, the secretion of fucosylated glycans improves the symbiotic relationship with commensal organisms—the effect of this relationship is an improved response to illness or stress.

Next, it was sought to determine how secretor status impacts health outcomes of the short bowel population. An intestinal failure registry with over 200 registered patients was used to determine the impact of secretor status on various sources of morbidity among those with short bowel syndrome. Outcomes were examined related to adaptation (e.g., time to independence from parenteral nutrition), infection (e.g., CLABSI rates (comparison by organisms) and/or resistant organism acquisition), microbial function (e.g., Vitamin B12 status, SBBO status), and other peripheral outcomes (e.g., admission rate, food protein allergy development).

For FUT2-positive subjects (77%), they can have increased susceptibility to infection by norovirus, rotavirus, and some *H. pylori* cases; lower circulating serum vitamin B12 levels; Graft-versus-host disease (GVHD); and/or other infections. For FUT2-negative subjects (23%), they can have increased susceptibility to Crohn's Disease, primary sclerosing, cholangitis, Type 1 diabetes, and sepsis (minor allele frequency=0.48).

Figure 27:
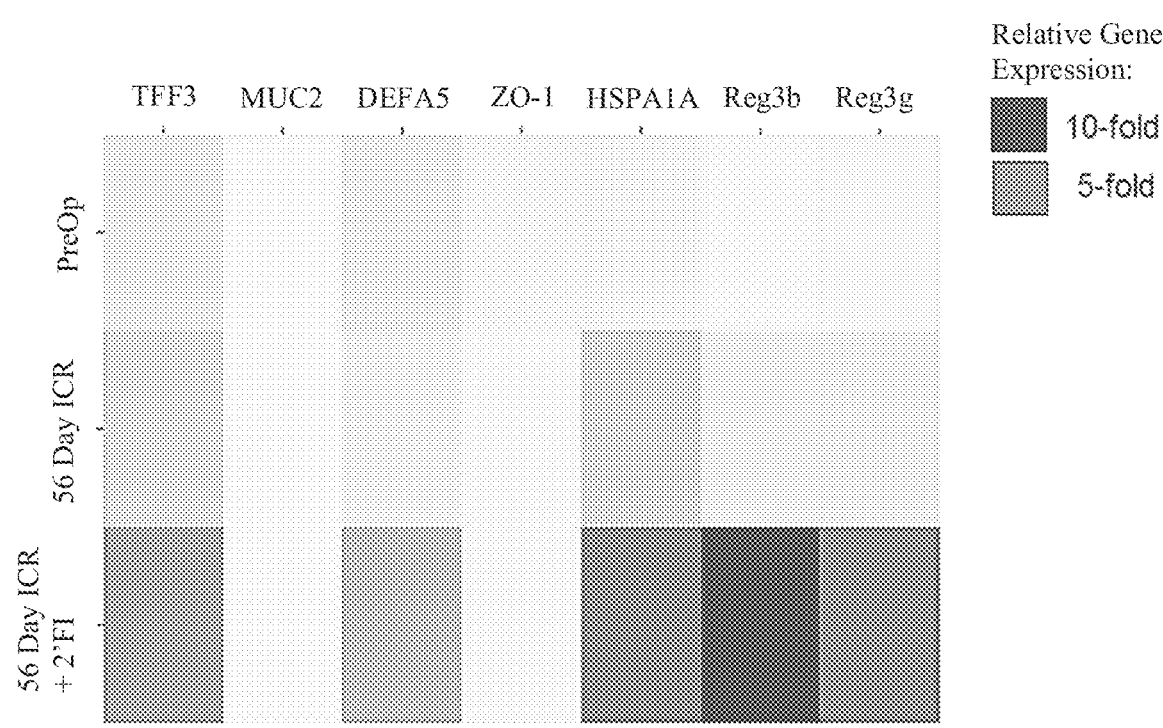
FIG. 27 is a diagram showing expression of genes (TFF3, MUC2, DEFA5, ZO-1, HSPA1A, Reg3b, Reg3g) relative to β-Actin gene expression in different groups, namely pre-operative murine subjects, post-ICR murine subjects without 2' FL supplementation, and post-ICR murine subjects with 2' FL supplementation. Subjects supplemented with 2' FL supplementation had an increased expression in genes TFF3, DEFA5, HSPA1A, Reg3b, and Reg3g.

FIG. 27 shows expression of genes (TFF3, MUC2, DEFA5, ZO-1, HSPA1A, Reg3b, Reg3g) relative to β-Actin gene expression in different groups, namely pre-operative subjects, post-ICR subjects without 2' FL supplementation, and post-ICR subjects with 2' FL supplementation. Significant differences in expression of Reg3β, Reg3γ, and ζ-Defensin 5 found by Mann-Whitney U test between standard diet and 2'Fl supplemented groups were seen.

Example 3. The Human Milk Oligosaccharide 2'-Fucosyllactose Augments the Adaptive Response to Extensive Intestinal Resection Intestinal resection resulting in short bowel syndrome (SBS) carries a heavy burden of long-term morbidity, mortality, and cost of care, which can be attenuated with strategies that improve intestinal adaptation. SBS infants fed human milk, as compared to formula, have more rapid intestinal adaptation. The hypothesis that the major non-caloric human milk oligosaccharide 2'-fucosyllactose (2'-FL) contributes to the adaptive response after intestinal resection was evaluated. Using a previously described murine model of intestinal adaptation, it showed increased weight gain from 21 to 56 days (p<0.001) and crypt depth at 56 days (p<0.0095) with 2'-FL supplementation after ileocecal resection. Further, 2'-FL increased small bowel luminal content microbial alpha diversity following resection (p<0.005) and stimulated a bloom in organisms of the genus Parabacteroides (log 2-fold=4.1, p=0.035). Moreover, transcriptional analysis of the intestine revealed enriched ontologies and pathways related to anti-microbial peptides, metabolism and energy processing. It was discovered that 2'-FL supplementation following ileocecal resection increases weight gain, energy availability through microbial community modulation, and histologic changes consistent with improved adaptation.

Intestinal failure describes a state of insufficient enteral function in which the intestine cannot support normal fluid balance, electrolyte balance, and growth. When enteral nutrition cannot meet these needs, central venous access is required for daily hydration and nutrition. The presence of a central venous catheter and the use of parenteral nutrition results in significant morbidity, mortality, cost, and lower quality of life. Lauriti et al. (2014) *JPEN Journal of parenteral and enteral nutrition* 38: 70-85; Spencer et al. (2008) *The American journal of clinical nutrition* 88: 1552-1559; Squires et al. (2012) *The Journal of pediatrics* 161: 723-728 e722; and Wales et al. (2011) *Journal of pediatric surgery* 46: 951-956. The most common cause of intestinal failure in the pediatric population is short bowel syndrome, due to extensive bowel resection. Goulet and Ruemmele (2006) *Gastroenterology* 130: S16-28. Following resection, the remaining intestine undergoes a process of adaptation presumed to compensate for the loss of absorptive surface area and restore full enteral function. Cheng et al. (2011) *Journal of clinical gastroenterology* 45: 846-849; McDuffie et al. (2011) *Journal of pediatric surgery* 46: 1045-1051; and Weser (1971) *The American journal of clinical nutrition* 24: 133-135. Thus, this process is the primary goal of intestinal rehabilitation as expeditious adaptation results in independence from central venous access and a reduction of its associated risks. Though the specific molecular mechanisms driving the adaptive response are not well understood, the major stimulus appears to be early enteral feeding. Feldman et al. (1976) *Gastroenterology* 70: 712-719; Tyson and Kennedy (2000) *Cochrane database of systematic reviews* CD000504.

While no consensus exists to suggest whether polymeric or monomeric formula is best for children with short bowel syndrome, a consistent benefit has been observed for human milk. Olieman et al. (2010) *Journal of the American Dietetic Association* 110: 420-426. Specifically, infants fed human milk achieve enteral autonomy sooner and with less morbidity than those fed formula. Andorsky et al. (2001) *The Journal of pediatrics* 139: 27-33; Kohler et al. (2013) *Journal of perinatology: official journal of the California Perinatal Association* 33: 627-630. Many growth factors are exclusively present in human milk and have been studied in the context of bowel resection. Cummins and Thompson (2000) *Gut* 748-754. However, none have solely demonstrated clear and sustained improvement of the adaptive process, prompting investigation into other components of human milk. Ballard and Morrow (2013) *Pediatr Clin North Am* 60: 49-74, 2013. Human milk oligosaccharides are carbohydrate polymers specific to human milk that may be non-nutritive yet able to modulate intestinal epithelial maturation and function by indirect mechanisms including affecting the microbiota. Abrahamsson and Sherman (2014) *The Journal of infectious diseases* 209: 323-324; Holscher et al. (2014) *The Journal of nutrition* 144: 586-591; LoCascio et al. (2007) *Journal of agricultural and food chemistry* 55: 8914-8919; and Yu et al. (2013) *Glycobiology* 23: 169-177. Thus, they may be responsible for the improved adaptive response observed in infants fed human milk. Andorsky et al. (2001) *The Journal of pediatrics* 139: 27-33.

2'-fucosyllactose (2'FL) is the most abundant oligosaccharide found in human milk, and is not a component of infant formulas. Chaturvedi et al. (2001) *Glycobiology* 11: 365-372; Coppa et al. (1999) *Acta Paediatr Suppl* 88: 89-94; Erney et al. (2000) *J Pediatr Gastroenterol Nutr* 30: 181-192; and Thurl et al. (1996) *Analytical biochemistry* 235: 202-206. The concentration of 2'-FL is about 2-3 grams per liter in milk produced by women with an active FUT2 gene allele, who are known as "secretors." Castanys-Munoz et al. (2013) *Nutrition reviews* 71: 773-789; Ferrer-Admetlla et al. (2009) *Molecular biology and evolution* 26: 1993-2003; Thurl et al. (2010) *The British journal of nutrition* 104: 1261-1271; and Totten et al. (2012) *Journal of proteome research* 11: 6124-6133. 2'-FL has not only been shown in vivo to stimulate enterocyte maturation, but it has been shown to act in a prebiotic fashion, encouraging the growth of beneficial bacteria, and discouraging the growth of pathogens. Asakuma et al. (2011) *The Journal of biological chemistry* 286: 34583-34592; Holscher et al. (2014) *The Journal of nutrition* 144: 586-591; LoCascio et al. (2007) *Journal of agricultural and food chemistry* 55: 8914-8919; and Yu et al. (2013) *Glycobiology* 23: 169-177. Though small quantities of 2'-FL may be detected in the blood stream of children receiving secretor milk, it is indigestible and not a caloric source for mammals. Coulet et al. (2014) *Regulatory toxicology and pharmacology: RTP* 68: 59-69; and Goehring et al. (2014) *PloS one* 9: e101692.

A mouse model of adaptation following extensive ileocecal resection (ICR) was previously described in Dekaney et al. (2007) American journal of physiology Gastrointestinal and liver phsuology 293: G1013-1022. This model demonstrated that murine adaptation is characterized histologically by unstained increases in villus height and crypt depth. Long-term bowel dilation and lengthening also occur, resulting in a sustained increase in mucosal surface area. Indeed, the improved intestinal function occurring as a result of the adaptive process is observed in a return to preoperative weight following resection, then further gain. In addition to anthropomorphic and histologic change, postoperative changes in the small bowel microbiome have also been reported. Devine et al. (2013) *PloS one* 8: e73140. For example, a decrease in diversity and shift to a predominance of members of the Firmicutes phylum, specifically the Clostridiaceae family were observed. Thus, increased intestinal surface area and microbial community changes characteristic of the adaptive process following intestinal resection occur as weight, a robust marker of intestinal function, increases.

In this Example, presented herein is the effect of 2'-FL supplementation on the adaptive response to ileocecal resection. Specifically, the effect of 2'-FL supplementation on a robust measure of adaptation following resection, weight change, was measured. It was discovered that supplementation with the non-caloric human milk oligosaccharide, 2'-FL, improved weight gain even before an impact on histologic measures of adaptation was observed. Pursuant to mechanistic exploration, the fecal microbiome and intestinal transcriptome at the site of resection were further characterized. This Example shows that 2'-FL supplementation augments the long-term adaptive response, not only by increasing mucosal surface area, but by augmenting microbial community shifts, which may improve food energy extraction.

Exemplary Materials and Methods

Male C57BL/6 mice (Jackson Labs, Me.) of 8 to 10 weeks of age were weighed and started on an exclusive polymeric formula diet one day prior to experiment start (Jevity 1 Cal, Abbott Nutrition, Columbus, Ohio). All mice were administered one dose of intraperitoneal Zosyn (at approximately 100 mg/kg) on experiment day 0. All animals were grouped by operation status and subgrouped into treatment and control arms (Table 4). Liquid diet was refreshed and weights obtained daily for 7 days then all mice were transitioned to a standard chow diet with access to water. Animals in both groups were weighed every other day and taken to 21 or 56 days for experiment completion. All animal studies were approved by the Cincinnati Children's Hospital Medical Center Institutional Animal Care and Use Committee.

TABLE 4

Guide to experimental group nomenclature.

| Nomenclature | Operative Group | Non-Operative Group |
|---|---|---|
| Control Group | Control ICR Subgroup | Non-Operative Control Subgroup |
| Treatment Group | 2'-FL Supplemented ICR Subgroup | Non-Operative 2'-FL Supplemented Subgroup |

Operation Status

Figure 28:
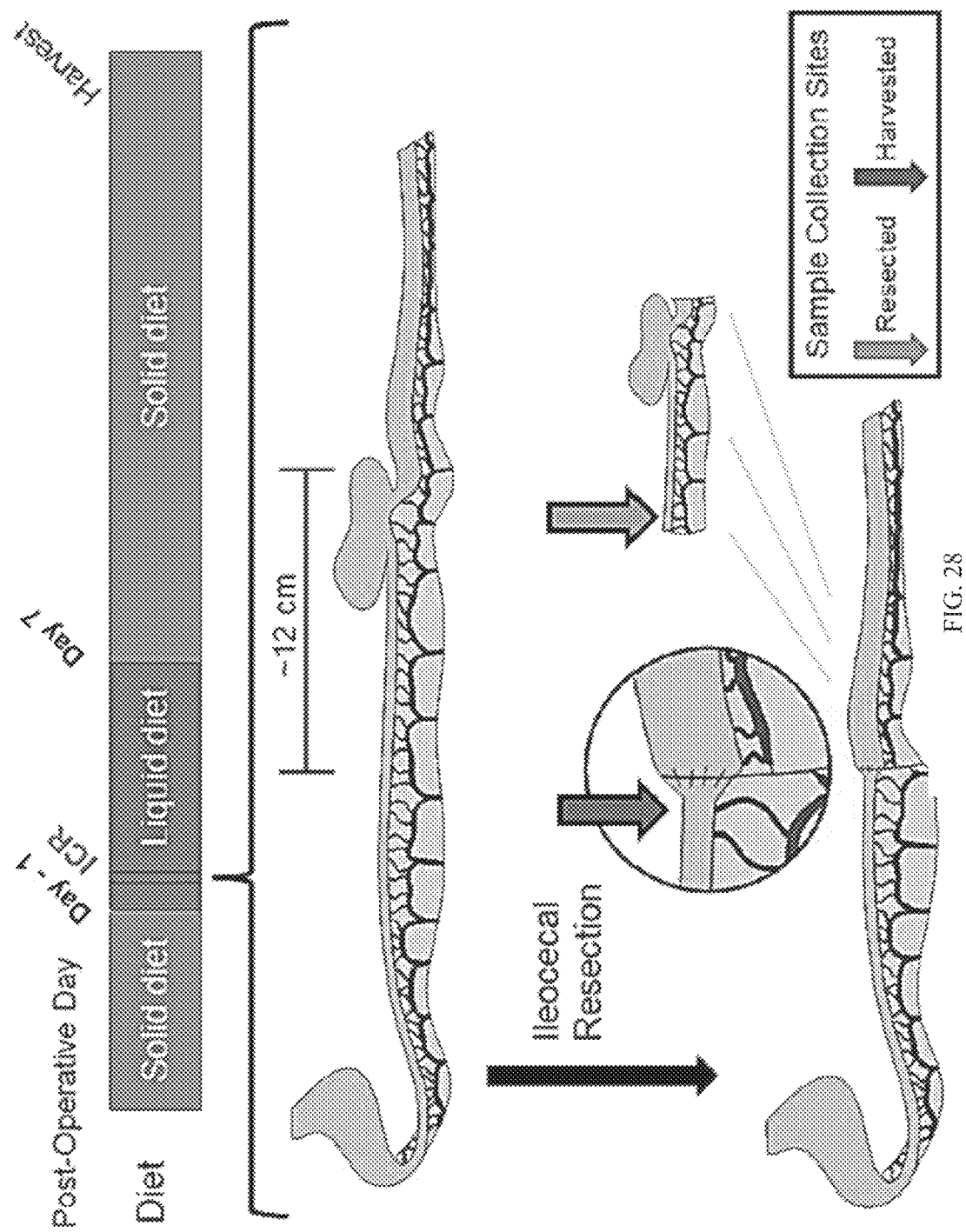
FIG. 28 is a schematic diagram of a study design of adaptive response to ileocecal resection (ICR) in mices. All operated male C57Black/6 mice were 8-10 weeks of age when placed on a liquid formula diet one day prior to undergoing ileocecal resection (ICR). Under sedation, a midline incision was made and the bowel eviscerated. Approximately 12 centimeters of ileum and cecum were identified and resected. Bowel continuity was restored by end-to-end anastomosis. Animals were recovered, maintained on liquid formula for 7 days, and then transitioned to chow through harvest occurring on either post-operative day 21 or 56. Sites of resected and harvested tissue collection are indicated by red and blue arrows, respectively.

Non-operated animals were maintained as described above. Operated animals were taken to the operating room on experimental day 0 and underwent ileocecal resection (ICR) as previously described in Dekaney et al. (2007) *American journal of physiology Gastrointestinal and liver physiology* 293: G1013-1022. Under the aid of an operating microscope and utilizing sedation with 2% isoflurane, a midline incision was made and the bowel eviscerated. The ileocecal junction was identified and approximately 12 cm of ileum and cecum were resected. Resected small bowel tissue and luminal contents were collected as described below. Intestinal continuity was restored by end-to-end anastomosis and the abdomen was closed (FIG. 28). ICR mice were then assigned to control or treatment subgroups, were administered analgesia with subcutaneous buprenorphine (0.05-0.1 mg/kg) and recovered overnight in a standard neonatal incubator warmed to approximately 38 degrees Celsius.

Control and Treatment Subgroups

Control (non-operated) animals were maintained as described above. Beginning on experiment day 0, treatment animals were supplemented with 2'-Fucosyllactose. 2'-FL was added to formula then water to a final concentration of 2.5 grams per liter. Formula was refreshed daily and water refreshed every other day.

Intestinal Tissue and Small Bowel Contents Preparation

Only weights were obtained from non-operated control animals. Resected intestine from operated animals was measured for length then the site of small bowel transection was processed for small bowel contents, histology, and RNA. At the time of experimental completion, small bowel immediately proximal to the site of anastomosis was also harvested for small bowel contents, histology, and RNA from the operated group.

Luminal small bowel contents were expressed into AllProtect Tissue Reagent (Qiagen Inc, CA). Bacterial DNA was extracted using the AllPrep DNA/RNA Mini Kit (Qiagen Inc, CA), according to kit instructions and prior to sequencing (described below). Small bowel tissue samples for RNA were placed into RNA Later (Life Technologies, NY). RNA extraction was accomplished following Qiagen RNeasy Plus Kit instruction (Qiagen Inc, CA). All nucleic acid samples were then stored at −80 Celsius until sequenced (described below).

Small bowel tissue samples for histology were cut in the longitudinal and transverse section, fixed with 4% paraformaldehyde, mounted in paraffin, and stained with hemotoxylin and eosin. Villous height, crypt depth, and bowel circumference were measured in a blinded manor. At least 10 well-oriented villus and crypt domains were assessed for each sample and two samples were averaged per mouse. The serosal circumference was measured twice per sample with two samples per mouse. The average value per mouse was determined. Measurements were performed using the Nikon Ti-Eclipse with NIS Element Advanced Research version 4.20 (Nikon Inc, NY).

Statistical Analysis of Weight and Histologic Data

In order to demonstrate the average trend in the populations measured and to assess significance, animal weight data was analyzed using a generalized estimating equation that incorporates repeated measures. Intestinal length was compared across groups using the Wilcoxon rank-sum test as values were not normally distributed. Histologic count data was averaged per mouse across two samples and compared by the Wilcoxon rank-sum test. Weight data was analyzed using Stata version 13.0 (StataCorp LP, TX). Remaining morphometric and histologic data were analyzed using GraphPad Prism version 5 (GraphPad Software Inc, CA).

16S Sequencing and Analysis

Following bacterial community DNA extraction from harvested small bowel contents obtained from operated mice taken to 8 weeks, samples were quantified using the Qubit ssDNA kit (Life Technologies, NY). The V3 and V4 regions of the 16S gene were then amplified and tagged with region-specific primers (Illumina flowcell compatible sequences), permitting sequencing of up to 576 individual bacterial communities on the same flowcell. Fadrosh et al. (2014) *Microbiome* 2:6. Two positive and 2 negative controls were included in each run. FastStart Taq kit (Roche Applied Science, Indianapolis, Ind.) was used for thermocycling then equal volumes of each amplicon were pooled and cleaned using the QIAquick PCR cleanup column (Qiagen, MD). The size of library pools was then verified using the Fragment Analyzer CE (AATI, Ames Iowa) and quantified using the Qubit high sensitivity dsDNA kit. Dilution to 1 nM and addition of PhiX V3 library (Illumina, Calif.) was followed by denaturation and further dilution to 12 pM in Illumina's HT1 buffer. The pool was then loaded to the Illumina MiSeq V2 500 cycle kit cassette, a sample sheet prepared, and the MiSeq run was initiated for FASTQ generation.

The 16S rRNA amplicon sequences were assembled and processed using an integrated, high-throughput analysis pipeline established at Cincinnati Children's Hospital Medical Center. Paired-end reads were assembled and quality filtered using Pandaseq v2.8. Masella et al. (2012) *BMC bioinformatics* 13: 31. Reads with ambiguous base calls, minimum overlap of 10 nt, or <425 nt were culled. Demultiplexing and removal of barcodes and primers was performed using the FastX-toolkit. Pearson et al. (1997) *Genomics* 46: 24-36. De novo clustering at 97% sequence similarity and chimera filtering was performed using UPARSE v7. Edgar (2013) *Nature methods* 10: 996-998. UCLUST, as implemented in QIIME v1.8, was used for taxonomic classification to the Greengenes v13.8 database. Caporaso et al. (2010) *Nature methods* 7: 335-336; Edgar (2010) *Bioinformatics* 26: 2460-2461; and McDonald et al. (2012) *The ISME journal* 6: 610-618. PyNast and FastTree were used to align sequence reads and construct a phylogenetic tree. Caporaso et al. (2010) *Bioinformatics* 26: 266-267; and Price et al. (2010) *PloS one* 5: e9490; Price M N et al. (2009) *Molecular biology and evolution* 26: 1641-1650. Additional integrated analyses included QIIME scripts for the generation of alpha and beta diversity metrics, corresponding visualizations, and summaries and plots of taxonomic composition. Alpha and beta diversity metrics were computed after subsampling to the lowest observed read depth (n=7,793 reads).

In order to estimate the treatment effect on alpha diversity metrics adjusted for housing cohort, a generalized ANCOVA model was used. The Chao1, Shannon, Simpson and Faith's Phylogenetic Diversity indices were examined. Differences between groups in community composition post-treatment, as measured by the weighted and unweighted UniFrac metrics (Lozupone and Knight (2005) *Applied and environmental microbiology* 71: 8228-8235) were tested by permutational ANOVA as implemented by the ADONIS function in the R package vegan. Oksanen et al. (2015) Vegan: Community Ecology Package. 2015; and Team (2015) R: A language and environment for statistical computing R Foundation for Statistical Computing [http://www.R-project.org/. 2015]. Pseudo-F statistics were obtained from sequential sums of squares from 1,000 permutations of the raw data. Differences in the overall abundance of specific OTUs between treatment subgroups at harvest was tested using a negative-binomial model as implemented in the R package DESeq2. Love et al. (2014) *Genome biology* 15: 550.

RNA Sequencing and Analysis

Transcriptional analysis was carried out on resected and harvested small bowel samples obtained from operated mice taken to 8 weeks. Murine RNA sequencing libraries were prepared from approximately 1.5 µg RNA using the TruSeq RNA Sample Preparation Kit (Illumina, Calif.) and sequenced using the HiSeq 2000 Sequencing System (Illumina, Calif.) with single-end 50 bp reads. Following removal of primers and barcodes, sequences were aligned to the mm10 genome using reference annotations from UCSC (Rosenbloom et al. (2015) *Nucleic acids research* 43: D670-681) (n=36,186 entities). Aligned reads were quantified and used to compute reads per kilobase per million mapped reads (RPKM); raw counts were then normalized using the DESeq algorithm and each harvested sample was baselined to its own resected sample. A filter was applied to the data, requiring at least three reads in all samples of at least one of the four experimental conditions (n=14,489 entities). The data discussed in this publication have been deposited in NCBI's Gene Expression Omnibus and are accessible through NCBI Gene Expression Omnibus (GEO) Series accession number GSE72590. Edgar et al. (2002) *Nucleic acids research* 30: 207-210.

In order to characterize the impact of 2'-FL supplementation while accounting for the effect of ileoecal resection, a t-test was applied between resected and harvested samples within control and experimental animals. Significance was set at a p-value of ≤0.05 and a fold change of 3, which generated 2,576 differentially regulated entities across two comparisons. Gene set unions and intersections of the control and experimental gene sets were identified through Venn diagrams. From the master list, the gene list specific to animals supplemented with 2'-FL were removed in order to identify genes differentially regulated only by ICR (n=546 entities); this gene set characterizes the adaptive response. Further, the 2'-FL response (n=2,030 entities) was identified by removing the adaptive response signature described above from the master list, leaving only genes regulated by 2'-FL supplementation after ICR which were not found in the non-supplemented adaptive response. Heatmaps were generated using hierarchical clustering with the Pearson's Centered distance metric and the average linkage rule; both entities and samples were clustered. All genomic analyses described above were performed in Strand NGS (Strand Life Sciences, CA).

Gene list functional enrichment was initially discovered using ToppFun, a member of the ToppGene Suite. Chen et al. (2009) *Nucleic acids research* 37: W305-311. No statistical correction was selected. Gene lists were further analyzed using ClueGO, a plugin for Cytoscape designed to decipher functionally grouped gene ontology and pathway annotation networks. Bindea et al. (2009) *Bioinformatics* 25: 1091-1093. At the time of data analysis, the annotation files were updated from sources to Jan. 1, 2015. "GO Term Fusion" was enabled to manage ontologic term redundancy and network specificity was set to medium. Results were restricted to pathways with p≤0.05 using Benjamini-Hochberg correction and Kappa scoring was set to 0.4. Biocyc annotations were assigned a rectangle, gene ontology biologic processes were assigned an ellipse, and Wikipathway annotations were assigned a diamond shape. No meaning was assigned to size or color.

Results

The median age (interquartile range) of operated mice at the time of ICR in the 21 day experiment was 93 days (93-94). In the 56 day experiment, mice were operated on at a median age of 76 days (72-77). The age of non-operated mice in the 21 and 56 day experiments were 66 days and 79 days, respectively. There was no difference in age between control and 2'-FL supplemented subgroups at each time point.

Weight Change

Figure 29:
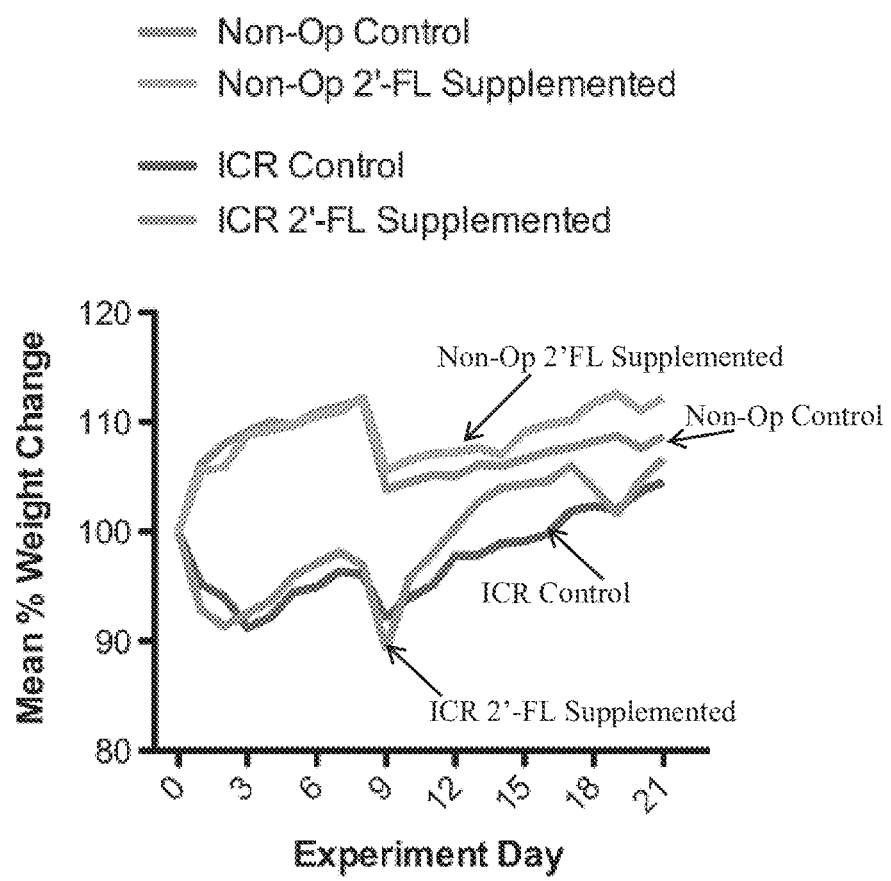
FIG. 29 is a graph showing mean weight change by group and subgroup relative to weight at experiment start. Non-operative control (n=4) and 2'-FL supplemented animals (n=5), and animals subjected to ileocecal resection (ICR) in control (n=4) and 2'-FL supplemented subgroups (n=3) were taken to experiment day 21. No significant difference between subgroups of either operated or non-operative groups was found. Multiple experiments are shown.

The median weight (interquartile range) of operated mice at the time of ICR in the 21 and 56 day experiments were 23.2 grams (21.3-25.6) and 25.8 grams (24.2-27.3), respectively. Animals in both control and 2'-FL supplemented ICR subgroups lost approximately 10% body weight during the first postoperative week. Both groups returned to their preoperative weight by 3 to 4 weeks after ICR and continued to grow. Animals taken to harvest at postoperative day 21 demonstrated no significant weight difference between control and 2'-FL supplemented subgroups (FIG. 29). When taken to 56 days, animals supplemented with 2'-FL, compared to controls, demonstrated increased weight on and beyond postoperative day 21 (FIG. 14) (p<0.001). At 56 days, animals of the control and 2'-FL supplemented ICR subgroups achieved 105% and 110% of preoperative body weight, respectively.

At the time of experiment start, the median weight (interquartile range) of non-operated mice in the 21 and 56 day groups were 23.7 grams (21.8-24.0) and 22.6 grams (22.4-24.2), respectively. Control and 2'-FL supplemented non-operative subgroups both gained an average of 108% body weight at 21 days (NS). When taken to 56 days after ICR, both groups had gained 117% body weight from study start (NS).

Histology

Figure 30:
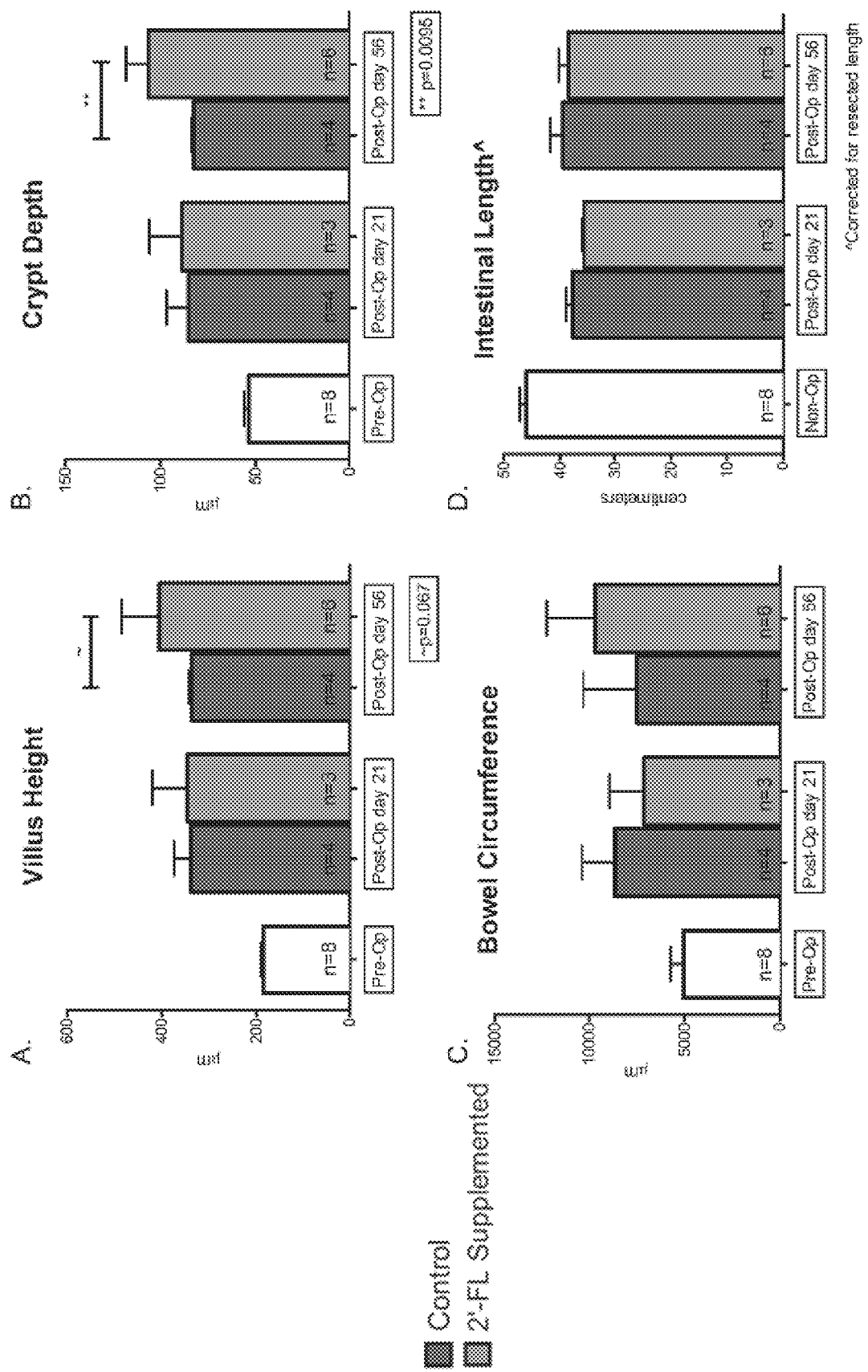
FIG. 30 is a series of graphs showing the comparison of histologic markers of adaptation following ileocecal resection among control and 2'-FL supplemented animals. Median and interquartile range of (Panel A) villus height, (Panel B) crypt depth, (Panel C) bowel circumference, and (Panel D) corrected intestinal length from three time points are shown. Tissue from pre-operative or non-operated (n=8) as well as control and 2'-FL supplemented tissues, respectively, on post-operative day 21 (n=4,3) and 56 (n=4,6). Comparisons between subgroups per time point by Mann-Whitney test, not significant unless otherwise indicated. Multiple experiments are shown.

The histologic measures of adaptation following ICR were augmented and prolonged with 2'-FL supplementation (FIG. 30). The median baseline crypt depth among all operated animals (interquartile range) was 54 µm (51-56) and increased following ileocecal resection. Crypt depth in control ICR animals was 85 µm (81-97) at 21 days and 82 µm (80-84) at 56 days. Among the 2'-FL supplemented ICR subgroups, crypts deepened to 89 µm (76-106) at 21 days and further to 106 µm (101-118) on postoperative harvest day 56. There was no difference between control and 2'-FL supplemented crypt depths on postoperative day 21. On postoperative day 56, the crypts of the 2'-FL supplemented ICR subgroup were significantly deeper than those of the control group (p=0.0095).

The median baseline villus height among all operated animals (interquartile range) was 186 µm (180-190) and also increased following ileocecal resection. Between postoperative days 21 and 56, villus heights among control ICR animals remained similarly elevated over preoperative heights at 338 µm (323-374) and 337 µm (257-342), respectively. Among the 2'-FL supplemented ICR subgroups, villus heights increased above baseline to 346 µm (318-420) on postoperative day 21 then 405 µm (340-484) on day 56. There was no difference between control and 2'-FL supplemented subgroups on postoperative day 21. On postoperative day 56, the villi of those mice supplemented with 2'-FL trended toward a greater height than those of the control subgroup (p=0.067).

The median baseline distal small bowel circumference was 5,041 µm (4,981-5,739) and increased following ileocecal resection. Between postoperative days 21 and 56, bowel circumferences decreased from 8,643 µm (7,367-10,413) to 7,491 µm (6,146-10,333), among the respective control ICR subgroups. Among the 2'-FL supplemented subgroups, small bowel circumferences tended to increase from 7,133 µm (6,529-8,930) to 9,671 µm (7,851-12,295) from postoperative harvest days 21 to 56. However, no statistical difference in small bowel circumference between control and 2'-FL supplemented subgroups on postoperative days 21 or 56.

The median baseline small bowel length (interquartile range) was 46 cm (41.38-47.13). Between postoperative days 21 and 56, intestinal lengths (corrected) increased from 37.8 cm (35.5-38.9) to 39.5 cm (37.3-41.8), respectively, among the control subgroups. Among the 2'-FL supplemented subgroups, intestinal lengths increased from 35.5 cm (35-36) to 38.5 cm (37.4-40.3) from postoperative harvest days 21 to 56. There was no difference in intestinal length between control and experimental groups on postoperative day 21 nor was there a difference on postoperative day 56.

Small Bowel Luminal Microbiome

Figure 31:
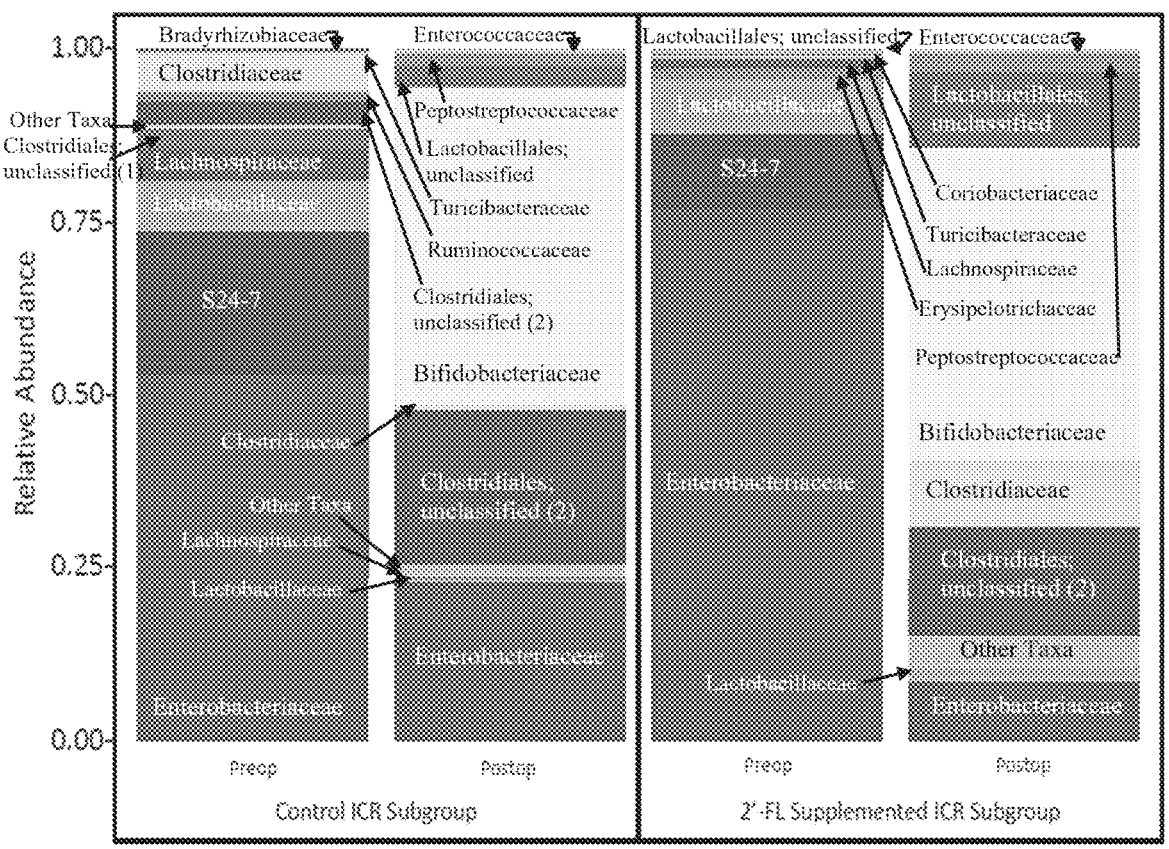
FIG. 31 is a graph depicting the relative abundance of bacterial families discovered in the luminal contents at the time of (Preop) and following (Postop) ileocecal resection. Families displayed as phylum including Firmicutes, Proteobacteria, Bacteriodetes, and Actinobacteria. Enterobacteriaceae were the most abundant taxa among preoperative samples and decreased following resection in both groups though a greater decline was observed among 2'-FL supplemented animals. A relatively larger bloom in Lachnospiraceae was also observed in this group.
Figure 32:
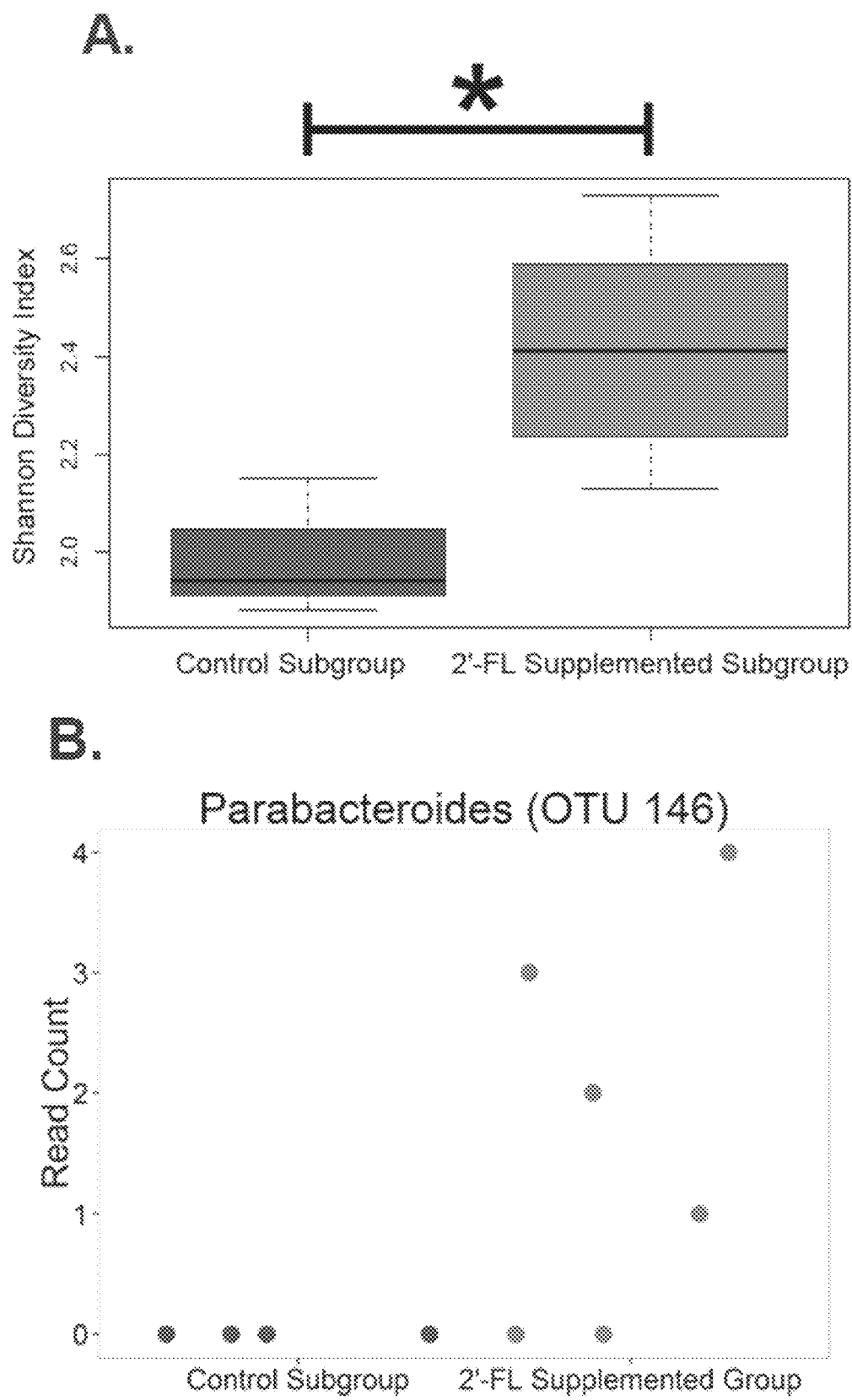
FIG. 32 is a series of graphs depicting the analysis of small bowel luminal contents at 56 days after ileocecal resection among control (n=4) and 2'-FL supplemented (n=6) animals. (Panel A) 2'-FL supplementation resulted in greater alpha diversity by Shannon diversity index (p<0.005). (Panel B) Sequence reads classified to the genus Parabacteroides were enriched by 2'-FL supplementation (log 2-fold=4.1, p=0.035) but not detected in control animals after resection.

The microbiome of the small bowel luminal contents of operated animal subgroups at 8 weeks were analyzed and relative abundance by experimental group displayed (FIG. 31). Differences in alpha diversity between control and 2'-FL supplemented subgroups were evaluated after controlling for housing cohort. A greater diversity of small bowel bacteria as measured by the Shannon Index was found among 2'-FL supplemented animals when compared to controls (p<0.005) (FIG. 32, Panel A). No differences were detected for the other alpha-diversity metrics examined. Nor were differences in the weighted or unweighted UniFrac metrics detected between 2'-FL-supplemented animals and controls post-treatment (p=0.143). Next, the log 2-fold change for 2'-FL supplemented animals was determined compared to controls, adjusted for housing cohort. Sequence reads were enriched among operated, 2'-FL supplemented animals for a single OTU that could be classified to the genus Parabacteroides: OTU_146 (log 2-fold=4.1, p=0.035). Parabacteroides was not detected in either study group at baseline, nor were Parabacteroides identified in the controls at follow-up (FIG. 32, Panel B).

Transcriptional Analysis of Small Bowel

Figure 33:
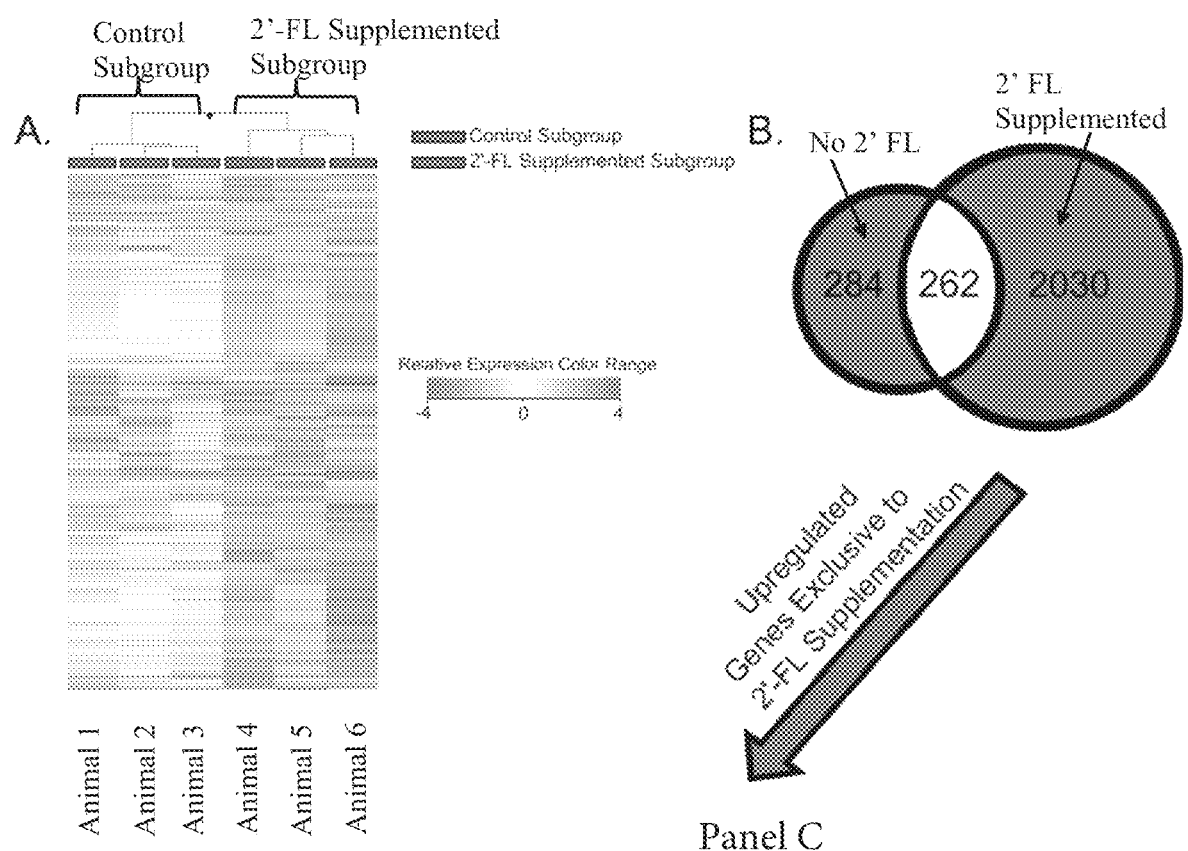
FIG. 33 is a series of diagrams showing the impact of ileocecal resection (ICR) on distal small bowel gene expression among representative control (n=3) and 2'-FL supplemented (n=3) animals. (Panel A) Hierarchical clustering of 2,567 genes differentially regulated between harvested and resected samples. (Panel B) The Venn diagram of these genes identifies those exclusively regulated by ICR in the absence of 2'-FL, those exclusively regulated by ICR in the presence of 2'-FL, and those shared between both groups. (Panel C) Non-redundant biologic functional information was extracted and deciphered from the list of genes exclusively upregulated by ICR in the presence of 2'-FL supplementation. All discovered annotations are present including Biocyc annotations as rectangles, GO Biological Processes as ellipses, and Wikipathways as diamonds. Related ontology and pathway groupings by color. No meaning assigned to size.
Figure 33:
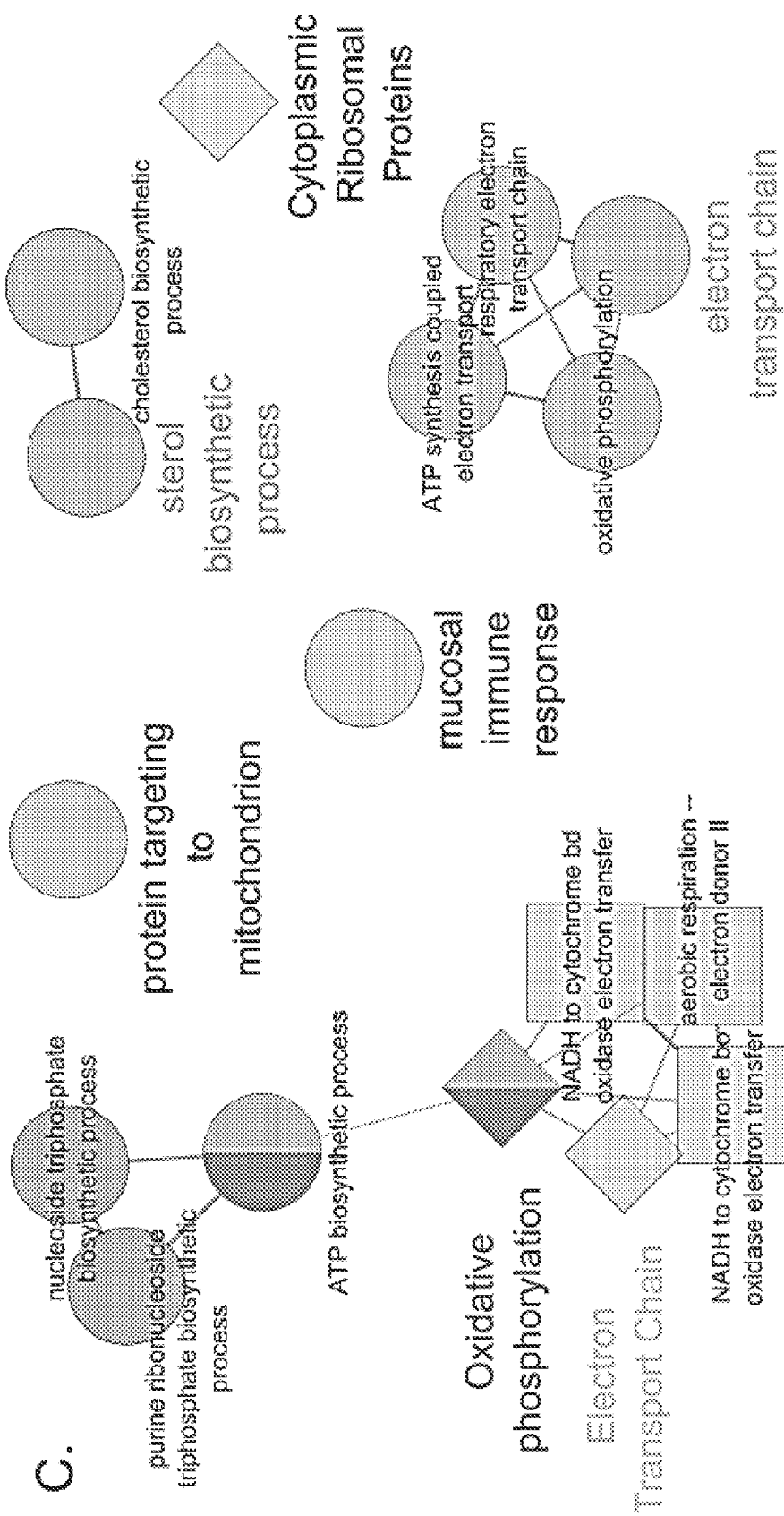

RNA-sequencing analysis was performed in Strand NGS from resected and harvested tissues among those operated subgroups taken to 8 weeks. Data were normalized using the DESeq algorithm and harvested samples were baselined to their respective resected sample. 2,576 differentially regulated entities (p-value<0.05 and fold change>2) were identified within control and/or experimental groups. Gene set unions and intersections of these groups were identified through Venn diagrams (FIG. 33, Panel B). A heatmap of all genes differentially regulated demonstrates an augmentation of the transcriptional directions appreciated among control animals when 2'-FL supplementation is considered (FIG. 33, Panel A).

The Adaptive Response

The "Adaptive Response" refers to the genes differentially regulated by harvested to resected comparison in the control subgroup, and represents 546 distinct entities (Tables 5-6). Among the upregulated entities of the adaptive response (n=154), ontologies pertaining to metabolic processes/metabolism were most salient, including glutathione derivative biosynthetic processes (p=5.0E-07), organic acid metabolic processes (p=3.4E-06), cellular modified amino acid metabolic processes (p=6.9E-06), carboxylic acid metabolic processes (p=2.7E-05), purine deoxyribonucleoside metabolic processes (p=1.1E-04), hormone metabolic processes (p=0.001), metabolism (p=2.7E-08), fatty acid metabolism (p=3.0E-07), and glutathione metabolism (p=5.7E-07), among others. Further, ontologies indicating a response to a shifting microbial community were discovered, including regulation of multi-organism processes (p=1.4E-04), response to external biotic stimulus (p=0.001), and response to other organism (p=0.001). Insulin-like growth factor signaling and purine salvage pathways (p=0.002 and p=0.003, respectively) were also discovered. Of the upregulated entities, the most strongly upregulated genes of the adaptive response include: Oas1e (FC=55.7), Cyp1a1 (FC=36.3), Upk3b (FC=27.1), Ly6g6c (FC=25.5), and Igfbp6 (FC=20.4).

Among the downregulated entities (n=392), ontologies pertaining to the regulation of cellular developmental processes were most salient, including cell development (p=7.75E-09), regulation of developmental process (2.78E-08), and regulation of cell development (p=3.54E-07). Other, tissue specific ontologies related to development include vasculature development (p=8.05E-06), brain development (p=4.92E-06), cardiovascular development (p=1.74E-05), and striated muscle development (p=1.32E-04). Ontologies related to neural function and generation were also discovered, including neurogenesis (p=8.70E-09), synaptic transmission (p=2.77E-07), neurotransmitter secretion (p=3.73E-06), and axonogenesis (p=8.62E-06). Finally, MAPK signaling was discovered, including the MAPK cascade (p=2.16E-06) and regulation of the MAPK cascade (p=4.53E-06) and may be related to co-discovered, downregulated entities including 'positive regulation of epidermal growth factor receptor signaling' (p=3.55E-05) and 'positive regulation of the ERBB signaling pathway' (p=4.53E-05).

Of the downregulated entities, the most strongly downregulated genes of the adaptive response include: Dhp (FC=−93.1), Gm129 (FC=−20.1), Bex1 (FC=−13.9), Hlf (FC=−13.0), and Abca1 (FC=−11.9).

Figure 34:
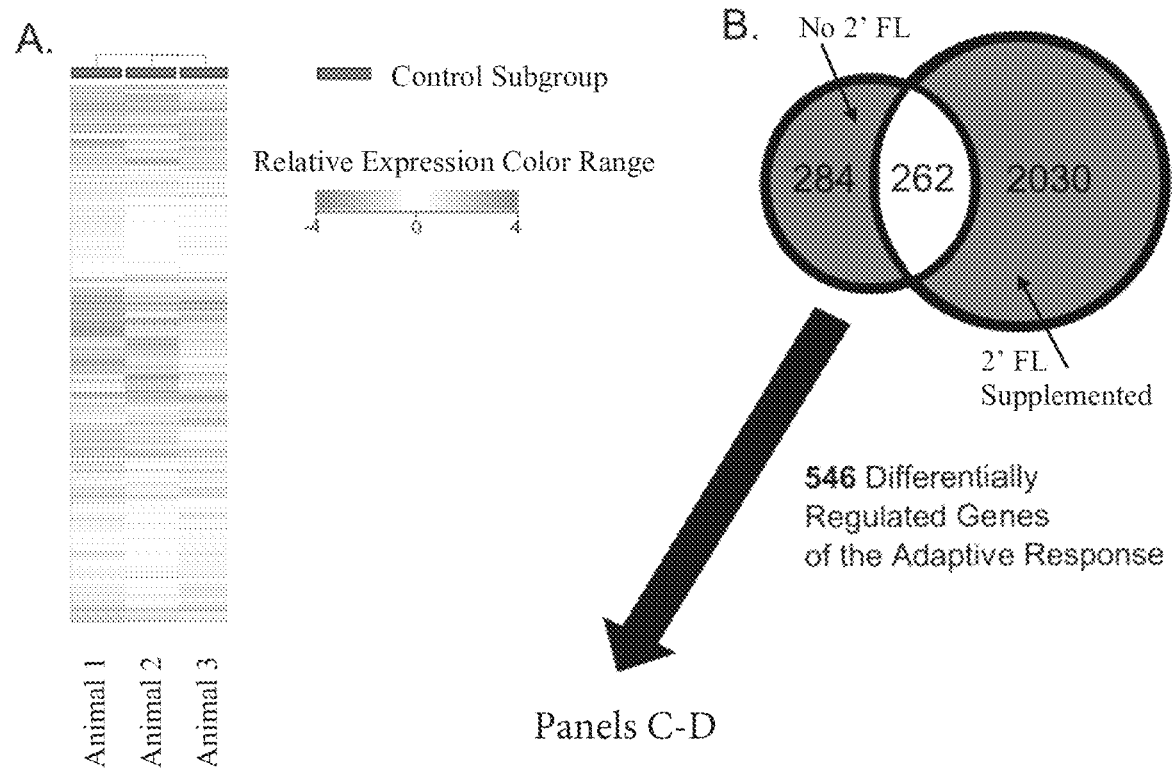
FIG. 34 is a series of diagrams showing the impact of ileocecal resection (ICR) on distal small bowel gene expression among representative control animals (n=3). (Panel A) Hierarchical clustering of 2,567 genes differentially regulated between harvested and resected samples. (Panel B) The Venn diagram of these genes identifies those regulated by the adaptive response to ICR (284 and 262 genes) and those exclusively regulated by 2'-FL supplementation following ICR (2030 genes). Non-redundant biologic functional information was extracted and deciphered from the list of genes (Panel C) up-regulated and (Panel D) down-regulated in the adaptive response to ICR. All discovered annotations are present including Biocyc annotations as rectangles, GO Biological Processes as ellipses, and Wikipathways as diamonds. Related ontology and pathway groupings by color. No meaning assigned to size.
Figure 34:
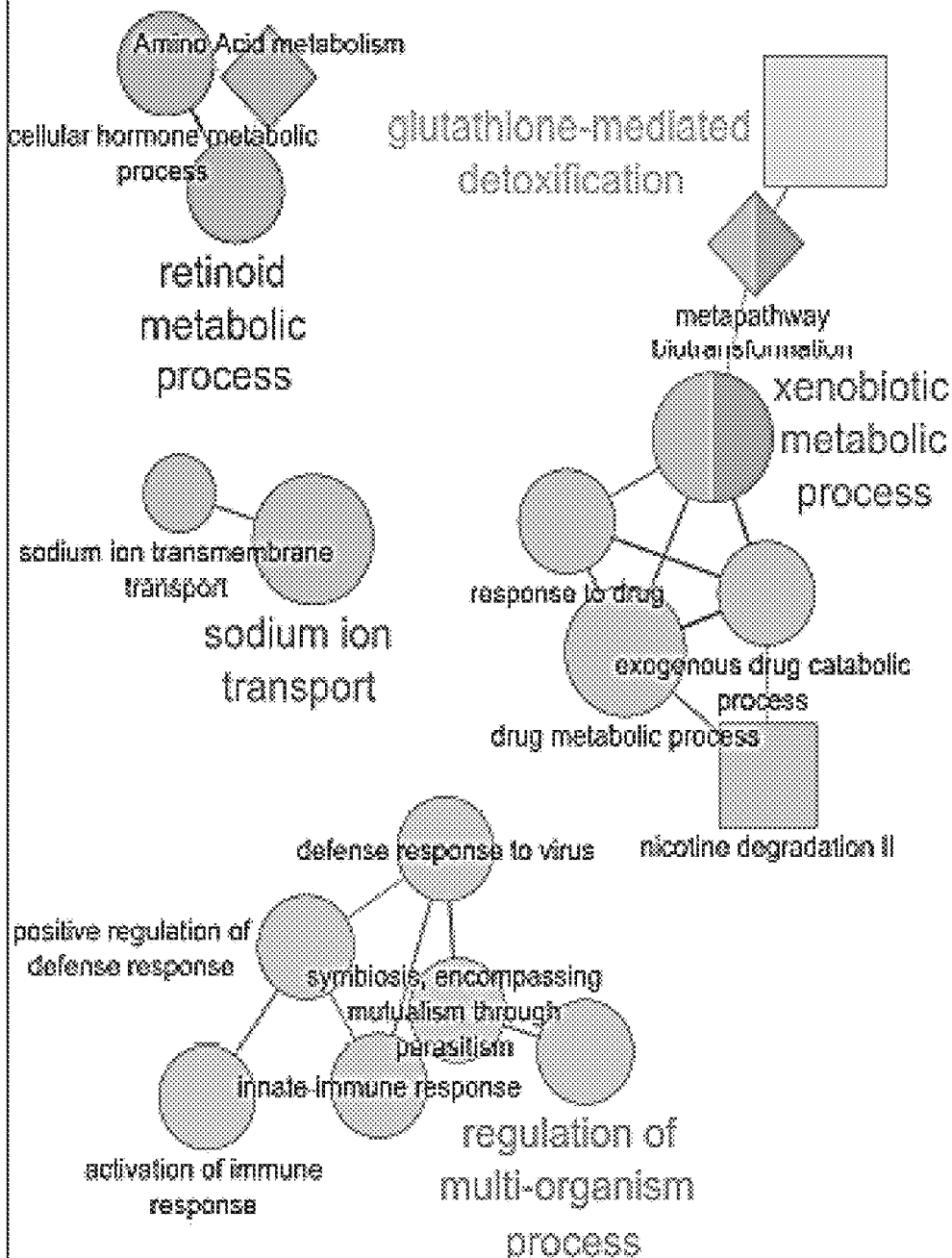
Figure 34:
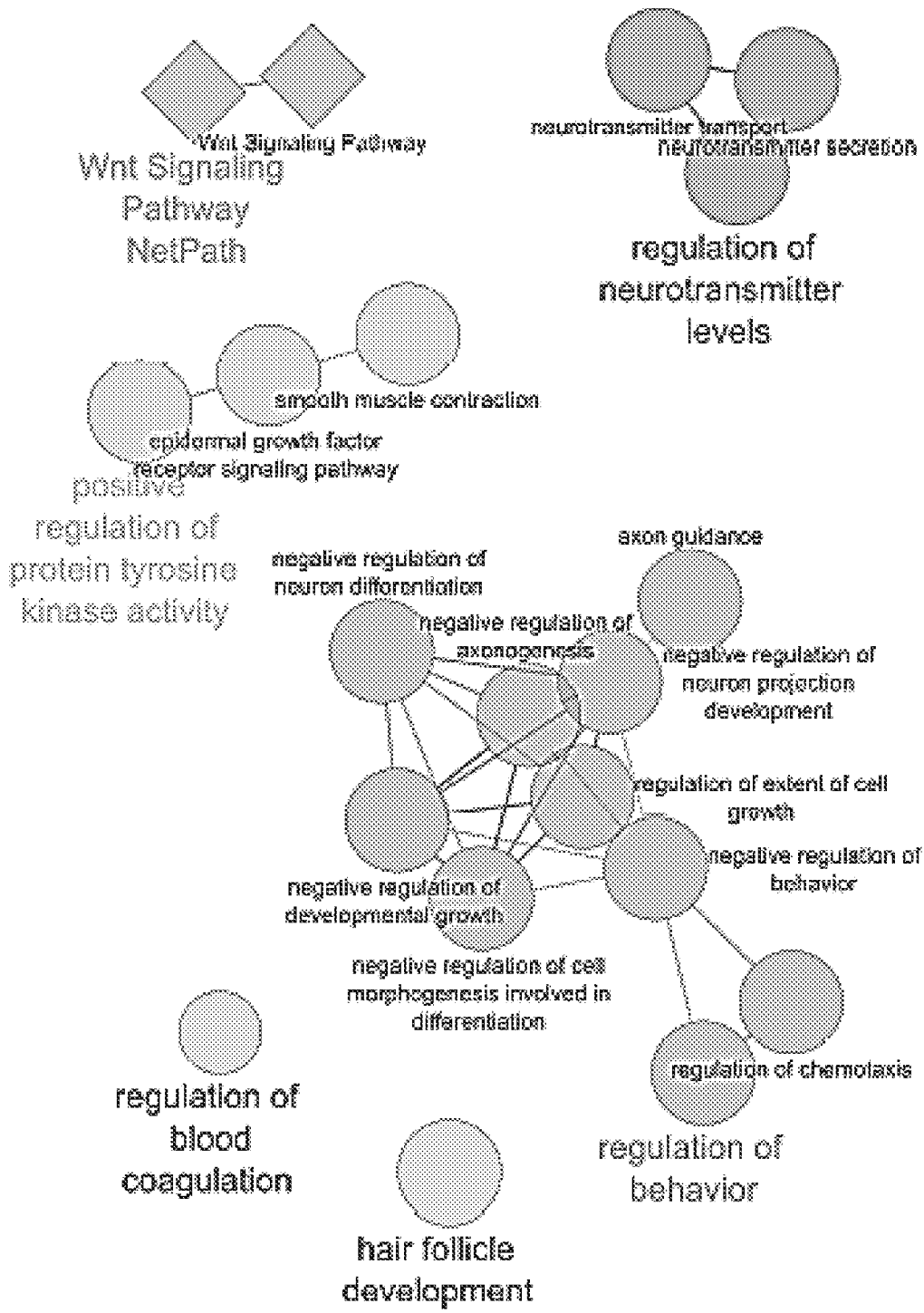

Cytoscape's ClueGO application was used to generate non-redundant, functionally grouped gene ontology and pathway annotation networks based on the up- and down-regulated gene set of the Adaptive Response (FIG. 34). Importantly, all discovered entities are described. The ClueGO network underscored the importance of multi-organism processes and retinoid metabolic processes in the adaptive response, and further highlighted xenobiotic metabolic processes and sodium ion transport.

TABLE 5

Adaptive Response

| Genes | Fold Change (Pre- to Post-op) | Genes | Fold Change (Pre- to Post-op) |
|---|---|---|---|
| Oas1e | 55.68724 | 2010005H15Rik | 10.364649 |
| Cyp1a1 | 36.291172 | Slc19a3 | 10.2076845 |
| Upk3b | 27.056425 | Hoxb13 | 10.072824 |
| Ly6g6c | 25.460863 | Catsper4 | 9.857689 |
| Igfbp6 | 20.355124 | Adad2 | 8.865586 |
| Ces1g | 18.843334 | Bglap3 | 8.41781 |
| Cyp2c29 | 18.698185 | Cox6b2 | 7.489439 |
| Slc38a8 | 15.756029 | Apol9a | 7.094183 |
| Ces1f | 14.839326 | Angptl4 | 6.967865 |
| Msln | 13.184034 | Cym | 6.9388614 |
| Lrrn4 | 12.545078 | Klre1 | 6.599061 |
| Onecut2 | 12.320146 | Arntl | 6.570107 |
| Vnn3 | 12.16223 | Nfil3 | 6.437701 |
| Rsad2 | 6.3033814 | Ankrd37 | 4.3686967 |
| C87414 | 6.2582345 | I730028E13Rik | 4.3372173 |
| Ccl24 | 6.213139 | Mir143hg | 4.2919316 |
| Gm2061 | 6.18331 | Cyp2c66 | 4.2673874 |
| Sprr2b | 6.169141 | Ttyh1 | 4.2295012 |
| Slc22a13b-ps | 6.16468 | Npas2 | 4.1654706 |
| Asic3 | 6.147054 | Cyp3a41a | 4.0965557 |
| 5730480H06Rik | 6.147054 | Glipr2 | 4.0920568 |
| Tmem252 | 6.1424704 | 2210019I11Rik | 4.0570517 |
| Gml | 6.090658 | Slc34a2 | 3.9986978 |
| Mfsd7c | 6.0234556 | Asprv1 | 3.9370272 |
| Anxa8 | 5.9349155 | Fmo1 | 3.9181147 |
| Ypel2 | 5.8253684 | Adh7 | 3.9138682 |
| Neat1 | 5.778688 | Cyp2b13 | 3.9024904 |
| BC018473 | 5.6765428 | Gm156 | 3.8947997 |
| Oit1 | 5.6431484 | Dab1 | 3.893036 |
| Gstm6 | 5.535627 | E330011O21Rik | 3.8816361 |
| Ada | 5.437839 | Fer1l4 | 3.8724012 |
| Hsf5 | 5.4258375 | Gstm3 | 3.8690388 |
| Cyp3a44 | 5.4117475 | C8g | 3.863791 |
| Ppm1n | 5.4074955 | Slfn4 | 3.8513834 |
| Apol9b | 5.3755107 | Drc1 | 3.837852 |
| Bbox1 | 5.301439 | Cpa3 | 3.8237495 |
| Enpp3 | 5.2613087 | Ccl4 | 3.767824 |
| Tmprss7 | 5.2385883 | Klrd1 | 3.7654612 |
| Krt12 | 5.21434 | Rspo1 | 3.762065 |
| Sprr2a3 | 5.124969 | Snhg11 | 3.7257493 |
| Yy2 | 5.0790377 | Gltpd2 | 3.700185 |
| Adh4 | 5.064387 | Meg3 | 3.6570597 |
| Sprr2a1 | 5.04428 | Tnip3 | 3.594819 |
| Sprr2a2 | 5.0251 | Gm14137 | 3.574975 |
| Igfbp2 | 4.985017 | Prdm1 | 3.5730839 |
| Zfp773 | 4.9729567 | Rhbdl1 | 3.5523345 |
| 9130230L23Rik | 4.917618 | Ces1e | 3.5306282 |
| Bhmt | 4.861276 | Gm10499 | 3.5262358 |
| 2010109I03Rik | 4.7730813 | Tm7sf2 | 3.484693 |
| Gm5535 | 4.684543 | Apol7a | 3.4661095 |
| Aqp8 | 4.59124 | Rtn4rl1 | 3.4524424 |
| Otop3 | 4.5608582 | 2900076A07Rik | 3.4501865 |
| Isg15 | 4.557051 | Gm12603 | 3.4317899 |
| Col7a1 | 4.5526123 | B230206H07Rik | 3.4107378 |
| Hsd17b6 | 4.5503354 | Snhg7 | 3.4104471 |
| Slc28a1 | 4.5437965 | Apoc2 | 3.4092906 |

TABLE 5-continued

Adaptive Response

| Genes | Fold Change (Pre- to Post-op) | Genes | Fold Change (Pre- to Post-op) |
|---|---|---|---|
| Cnpy1 | 4.533548 | Gpm6a | 3.4065084 |
| Gstm7 | 4.5193195 | H2-Q10 | 3.4034703 |
| Gm3336 | 3.3988173 | Syt4 | −3.0144246 |
| Tmem140 | 3.3811278 | Sema4f | −3.0175133 |
| D7Ertd715e | 3.368934 | Lrrn1 | −3.0229526 |
| Ccbl1 | 3.3553753 | Bend3 | −3.0284889 |
| Fgfl1 | 3.3246849 | Gpr124 | −3.0357914 |
| Tppp | 3.3226123 | Tbkbp1 | −3.03679 |
| 3110062M04Rik | 3.317721 | Uhrf1 | −3.0501406 |
| Ccdc114 | 3.311733 | Prkcb | −3.0517447 |
| Gzma | 3.2811782 | Tlr7 | −3.055157 |
| Atat1 | 3.260353 | Ror2 | −3.0573814 |
| Slc16a11 | 3.249878 | Dclk3 | −3.0580695 |
| Il1f9 | 3.2346494 | Ttpa | −3.0637584 |
| Slc17a4 | 3.2287903 | Sox9 | −3.0647893 |
| 5033406O09Rik | 3.2268305 | Morc4 | −3.0658197 |
| Hspa11 | 3.2018707 | Xkr5 | −3.0724082 |
| Gstt1 | 3.1978972 | Astn1 | −3.0724084 |
| Gm3776 | 3.1742485 | Zbtb20 | −3.0733223 |
| Scamp5 | 3.1641972 | Dusp7 | −3.074938 |
| Nfkbiz | 3.1616163 | Gprasp2 | −3.082746 |
| Ambp | 3.1549852 | Kcng1 | −3.0856562 |
| Gm10639 | 3.146311 | Frem1 | −3.0856562 |
| Mx1 | 3.141914 | F5 | −3.0943365 |
| E330033B04Rik | 3.1351166 | Stab2 | −3.0949304 |
| Pnp2 | 3.119203 | Map3k15 | −3.0970185 |
| Gsta2 | 3.0938945 | Rab6b | −3.1134045 |
| Gsta1 | 3.0922368 | Tmem132b | −3.1194944 |
| Gm14085 | 3.090995 | Map9 | −3.1194944 |
| Ier5 | 3.0884144 | Zfp503 | −3.1199274 |
| Fabp1 | 3.0856547 | Gm18392 | −3.122367 |
| Slc28a2 | 3.0826354 | Pcsk1n | −3.1224627 |
| Ddc | 3.0764577 | Slc6a9 | −3.1253529 |
| Rdh19 | 3.0736911 | Pid1 | −3.129461 |
| Gngt1 | 3.0735269 | 9-Mar | −3.1365216 |
| Trim15 | 3.0533676 | Kcnq5 | −3.1392205 |
| Tmem150a | 3.0491831 | Plcb1 | −3.1398296 |
| Zbp1 | 3.034771 | Nmu | −3.1420853 |
| G6pc | 3.0311456 | Slc7a2 | −3.1492507 |
| Vamp5 | 3.0293875 | Gm15284 | −3.1504245 |
| Ano1 | −3.000228 | 2610528A11Rik | −3.1537778 |
| Entpd3 | −3.0018487 | Pik3ip1 | −3.1560452 |
| Cxxc5 | −3.0019693 | Fibin | −3.156425 |
| E130311K13Rik | −3.0034944 | Ubxn10 | −3.1601262 |
| AY761184 | −3.0086164 | Hepacam | −3.160871 |
| Paqr5 | −3.0118387 | Sirpa | −3.163981 |
| 1190005I06Rik | −3.0118387 | Ccdc8 | −3.1706429 |
| Penk | −3.1706429 | Cdk6 | −3.3120325 |
| Prr16 | −3.170643 | Piezo2 | −3.3129106 |
| Serpine1 | −3.170643 | Scube2 | −3.3149579 |
| Kbtbd13 | −3.170643 | Pacsin3 | −3.3149579 |
| Sult1c2 | −3.1766703 | Akp3 | −3.324673 |
| Dagla | −3.179887 | Slc14a1 | −3.3280606 |
| Slc20a1 | −3.1827092 | Gm15293 | −3.333046 |
| Fam107a | −3.187331 | Lrrn2 | −3.3352954 |
| Slc7a5 | −3.1880612 | Pygm | −3.3553877 |
| Bik | −3.1881607 | Adcy3 | −3.3601408 |
| Pitpnm2 | −3.1962147 | Phf19 | −3.3621473 |
| Syk | −3.202356 | Itln1 | −3.370239 |
| Ppp1r3d | −3.2038457 | Cd33 | −3.372964 |
| Kif1a | −3.2040887 | Fzd8 | −3.375392 |
| 1810041L15Rik | −3.2067497 | Hand1 | −3.379186 |
| Lgr5 | −3.2140648 | Atp10d | −3.381623 |
| Phgdh | −3.215673 | Cadps | −3.3870444 |
| Abcg1 | −3.2179577 | Smarca1 | −3.4016457 |
| Afap1 | −3.2188642 | Rrad | −3.404594 |
| Ephx1 | −3.2245295 | 1810013A23Rik | −3.4163682 |
| Mecom | −3.2272325 | Cybb | −3.4327676 |
| Wdfy4 | −3.229249 | C4bp | −3.4354908 |
| Zfp69 | −3.2395914 | Olfml2b | −3.4356816 |
| Zfp202 | −3.240555 | Defa24 | −3.4384172 |
| AI118078 | −3.242401 | Slc8a3 | −3.445398 |
| Selp | −3.2440002 | Dgkh | −3.4551592 |
| Uchl1 | −3.245549 | Hhex | −3.4571273 |

TABLE 5-continued

Adaptive Response

| Genes | Fold Change (Pre- to Post-op) | Genes | Fold Change (Pre- to Post-op) | Genes | Fold Change (Pre- to Post-op) | Genes | Fold Change (Pre- to Post-op) |
|---|---|---|---|---|---|---|---|
| Itprip | −3.2523966 | Timp3 | −3.4575524 | Colgalt2 | −4.260577 | Defa-rs1 | −4.8519726 |
| Scn7a | −3.2540767 | Klf2 | −3.4643986 | Adcy8 | −4.267848 | Me3 | −4.8793035 |
| 1810008I18Rik | −3.255729 | Crocc | −3.4658413 | Slc4a8 | −4.273749 | Fam64a | −4.905607 |
| Clspn | −3.255835 | Sgcd | −3.4688468 | Hoxc8 | −4.2842755 | Nr1d1 | −4.9202027 |
| A730056A06Rik | −3.262746 | Rab11fip5 | −3.4793274 | Col4a3 | −4.2971287 | Pdgfb | −4.955794 |
| Larp6 | −3.273854 | Defa5 | −3.4871445 | Nrxn2 | −4.299426 | Dok7 | −4.9784865 |
| Hlx | −3.27429 | Fjx1 | −3.490782 | Adra2b | −4.3304358 | Slc5a7 | −4.9784865 |
| Lrp11 | −3.28288 | Samd5 | −3.49182 | Sox10 | −4.3304358 | Celsr1 | −4.993364 |
| Jazf1 | −3.283975 | Plxna3 | −3.4926012 | Hoxa7 | −4.356792 | Nr1d2 | −5.002184 |
| Fcrla | −3.289944 | Bambi | −3.4937003 | Rab3c | −4.3957705 | Cdh19 | −5.0156455 |
| Tbc1d16 | −3.2959993 | Per2 | −3.5011175 | Bhlha15 | −4.4140763 | Dpysl5 | −5.0405602 |
| Klf11 | −3.3001049 | Adamts8 | −3.5061762 | Fam83c | −4.418704 | Ccdc24 | −5.066972 |
| Pvrl4 | −3.3003337 | Hao2 | −3.5071278 | Abcb1a | −4.4244623 | Tgfbr3 | −5.0822115 |
| Arhgef4 | −3.3047411 | Rnf122 | −3.509137 | Hmgcs2 | −4.426689 | Wnt3 | −5.0908365 |
| Zc3h7b | −3.3054862 | Syt7 | −3.5109363 | Plb1 | −4.44904 | Slc16a7 | −5.094879 |
| Ltbp2 | −3.3075354 | Cc2d2a | −3.5138056 | Iglon5 | −4.450286 | Hspa2 | −5.09768 |
| Gng3 | −3.30875 | Rad51c | −3.5144947 | Tmem200c | −4.4626145 | Ang5 | −5.1138015 |
| Fam57b | −3.3120162 | Spata24 | −3.5146868 | Zfp518b | −4.468894 | Figf | −5.115606 |
| Insrr | −3.531931 | Epb4.2 | −3.794679 | E130309D14Rik | −4.472729 | Adora1 | −5.1329474 |
| Mmp7 | −3.5359716 | Angptl1 | −3.8179603 | Sptbn2 | −4.492491 | Klhdc8a | −5.1939282 |
| Gfra1 | −3.540921 | Gm14851 | −3.8273768 | Arid5b | −4.496057 | Slfn9 | −5.2157965 |
| Pcdhgb2 | −3.5487092 | Mylip | −3.8279898 | Slc4a11 | −4.496311 | Fgf13 | −5.238472 |
| Zc3hav1l | −3.5528026 | Abi3bp | −3.8372395 | Fry | −4.499457 | Tns4 | −5.268194 |
| Gm21498 | −3.5529468 | LOC101055828 | −3.8466678 | Kcnh2 | −4.5156918 | Ncam1 | −5.3607063 |
| Gm14850 | −3.5529468 | 2310044G17Rik | −3.8493059 | Serpina3n | −4.5188556 | Clstn3 | −5.391138 |
| Kcnma1 | −3.5543756 | Prph | −3.856163 | Siglech | −4.540081 | Stmn2 | −5.395782 |
| Clps | −3.5582554 | Cdh13 | −3.860055 | Ms4a4c | −4.545475 | Slc2a13 | −5.4095836 |
| Mef2c | −3.559267 | Enpp2 | −3.8604732 | Pnmal2 | −4.5566707 | Kif5c | −5.4152894 |
| Xkrx | −3.5630527 | Mapk10 | −3.868413 | Ang4 | −4.56656 | Epha7 | −5.4327784 |
| H2-Ob | −3.5643182 | Syngr3 | −3.8709915 | Mfi2 | −4.570622 | Cubn | −5.4417152 |
| Serpina1f | −3.5685515 | Tmem200b | −3.8805606 | Klf12 | −4.578422 | Cxcl13 | −5.493069 |
| Tspan4 | −3.5760953 | Bves | −3.8972876 | Pla2g2f | −4.5851336 | Igsf11 | −5.517324 |
| Themis2 | −3.5798643 | Aatk | −3.8972876 | Cbs | −4.5956373 | Sdk1 | −5.6657996 |
| Raet1e | −3.580587 | Pycr1 | −3.9035506 | Zfp521 | −4.596926 | Pou2f2 | −5.684467 |
| Shisa4 | −3.5863278 | Galnt16 | −3.9092424 | Gng7 | −5.7032747 | Aldh1l2 | −7.850667 |
| Tnxb | −3.5865886 | Sorcs2 | −3.9172468 | Fam19a5 | −5.7901397 | Dner | −7.8670692 |
| Dlg2 | −3.5935102 | Notch2 | −3.9188633 | Aff3 | −5.791566 | Vat1l | −7.8689246 |
| Gm10104 | −3.5939157 | Prune2 | −3.9193692 | Inmt | −5.801482 | Abca9 | −7.8750873 |
| Cbfa2t3 | −3.594331 | Pms1 | −3.9196439 | Slc22a3 | −5.8876524 | Fzd9 | −8.097951 |
| Lyz1 | −3.5977657 | Nynrin | −3.9245465 | Wfikkn2 | −5.895476 | Syt1 | −8.29709 |
| Col24a1 | −3.6179214 | Zfp791 | −3.930317 | E2f7 | −5.903148 | Fam222a | −8.3604145 |
| Dusp26 | −3.6243188 | Fzd2 | −3.951704 | Timd4 | −5.984188 | Gdf10 | −8.434473 |
| Nol3 | −3.6401176 | Tmem179 | −3.9551704 | Lefty1 | −6.124838 | Ngfr | −8.473508 |
| Nhs | −3.648163 | Pacsin1 | −3.9597423 | Gper1 | −6.1332235 | Phox2b | −8.620394 |
| Defa3 | −3.6499734 | Nupr1 | −3.967268 | Muc2 | −6.1446185 | Faim2 | −8.639057 |
| Pirt | −3.650044 | Syn1 | −3.9691548 | Robo1 | −6.1466436 | Car14 | −8.680829 |
| Thsd7a | −3.6528337 | Sox7 | −4.0200205 | Chl1 | −6.1497965 | Gal | −8.915272 |
| Defa17 | −3.6595685 | Foxred2 | −4.0200205 | Snord17 | −6.171313 | Serpina1b | −9.094129 |
| Kcna2 | −3.6772928 | Sorl1 | −4.0285826 | Adamts18 | −6.190691 | Col4a6 | −9.335449 |
| Gm15315 | −3.6885705 | Hoxb7 | −4.0312195 | Pcsk2 | −6.322834 | Cd22 | −9.601347 |
| Ascl2 | −3.6944556 | Cyp2u1 | −4.0396624 | Gm7849 | −6.337134 | 1810010D01Rik | −10.0115 |
| Prickle1 | −3.6977992 | Kif5a | −4.0417614 | Gm7861 | −6.337134 | 1700011H14Rik | −10.430209 |
| Tanc2 | −3.698227 | Rbm20 | −4.0571885 | Defa21 | −6.3872523 | Per3 | −11.01521 |
| Clip3 | −3.711623 | Gpr37l1 | −4.084971 | Epb4.1l4a | −6.495958 | Esp38 | −11.234799 |
| 5930430L01Rik | −3.7153935 | Map1b | −4.08517 | Rasd2 | −6.509617 | Abca1 | −11.871628 |
| Gm6696 | −3.7282917 | Agt | −4.0913033 | Eef1a2 | −6.5577006 | Hlf | −13.019251 |
| Sphkap | −3.7309775 | Unc5c | −4.0953956 | Mchr1 | −6.583243 | Bex1 | −13.881219 |
| Igf1r | −3.7351139 | Fmn2 | −4.1019616 | Sowahd | −6.600195 | Gm129 | −20.128527 |
| Necab1 | −3.7765453 | Apcdd1 | −4.1027784 | Defa22 | −6.601852 | Dbp | −93.14646 |
| Pcdh9 | −3.7779388 | Clu | −4.1128726 | Mylk3 | −6.6076283 | | |
| Gucy1b3 | −3.7831593 | Pla2g2a | −4.112886 | Bank1 | −6.6160755 | | |
| Gm16576 | −3.7883856 | Htr3a | −4.13878 | Nfasc | −6.658203 | | |
| Il1rl2 | −3.794679 | Rtn1 | −4.146246 | Gp2 | −6.6705914 | | |
| Ptprd | −4.146578 | Zcchc12 | −4.596926 | Hif3a | −6.6777143 | | |
| Syn2 | −4.169232 | Abca8a | −4.6146426 | Cd109 | −6.7721906 | | |
| Zfhx3 | −4.1713805 | Sema5a | −4.619509 | Tubb3 | −6.9163113 | | |
| Klb | −4.175414 | Egf | −4.6377954 | Habp2 | −7.003255 | | |
| Ndrg4 | −4.1881275 | Dpp10 | −4.6455445 | Chrna3 | −7.010726 | | |
| Slc10a4 | −4.1890545 | Plagl1 | −4.6560197 | Defa2 | −7.0445547 | | |
| Sema3a | −4.2196455 | Syne4 | −4.7077384 | Akr1c14 | −7.107737 | | |
| Sell | −4.2247725 | Fbxo10 | −4.7088304 | Defa20 | −7.2500515 | | |
| Abcb1b | −4.2314973 | Abcb4 | −4.761966 | Gm21002 | −7.3369637 | | |
| Chrm3 | −4.233805 | Hpd | −4.788614 | Cys1 | −7.3584113 | | |
| Angptl2 | −4.243333 | Ces2a | −4.8405895 | Svep1 | −7.449047 | | |

TABLE 5-continued

Adaptive Response

| Genes | Fold Change (Pre- to Post-op) |
|---|---|
| Tlr9 | −7.557876 |
| Il6ra | −7.5621767 |
| Gm15308 | −7.627997 |
| Abca8b | −7.720741 |
| Tef | −7.849214 |

TABLE 6

2'-FL Signature Response

| Genes | Fold Change (Pre- to Post-op) | Genes | Fold Change (Pre- to Post-op) |
|---|---|---|---|
| Tmem202 | 18.021654 | AA467197 | 6.5654736 |
| Map3k12 | 16.205387 | Usmg5 | 6.5642724 |
| 2200002J24Rik | 15.954933 | Akr1c13 | 6.5072913 |
| Hemt1 | 15.358652 | 9430038I01Rik | 6.4743285 |
| 2010308F09Rik | 14.343246 | Cox7a1 | 6.410991 |
| Mcpt2 | 13.424349 | 1700001C19Rik | 6.3904114 |
| Fmr1nb | 12.732647 | Gramd2 | 6.347158 |
| Tpsb2 | 11.687032 | Ccl8 | 6.2504 |
| A630001O12Rik | 10.8832855 | Atp5e | 6.205875 |
| 5830416P10Rik | 10.248166 | S100a14 | 6.184321 |
| Apoa2 | 9.395423 | Insl6 | 6.1054854 |
| Guca1a | 9.305832 | 2810433D01Rik | 6.1000423 |
| Ccl20 | 9.2800865 | A930006K02Rik | 6.0947804 |
| Pbx4 | 9.261663 | Gpx4 | 6.0650196 |
| Tex14 | 9.1516485 | Hoga1 | 6.0542 |
| Styxl1 | 9.073148 | Leap2 | 6.029594 |
| Slpi | 8.998916 | Fscn3 | 6.023785 |
| Ubd | 8.9709635 | Chac2 | 6.0174036 |
| Gm12408 | 8.867987 | Ctla2b | 5.9207687 |
| Akr1c19 | 8.797366 | Prg2 | 5.9193745 |
| Krt14 | 8.677704 | Gsta3 | 5.904769 |
| 0610008F07Rik | 8.362063 | Gm17619 | 5.8839293 |
| Fabp2 | 8.144174 | Tmigd1 | 5.848611 |
| C87977 | 8.093846 | BC061194 | 5.8445396 |
| Gm14399 | 8.007578 | Nqo1 | 5.8303804 |
| Gm15133 | 7.7414575 | Ctxn3 | 5.820405 |
| Ly6g6d | 7.662457 | Acn9 | 5.819402 |
| 3110070M22Rik | 7.550518 | 1700012D14Rik | 5.7961235 |
| Upb1 | 7.462941 | Sprr1a | 5.777962 |
| Slc6a18 | 7.38246 | Znhit3 | 5.7161274 |
| Tnni1 | 7.3797774 | Mrpl33 | 5.6899858 |
| Zfp92 | 7.305564 | Aldoc | 5.6542244 |
| Nkain4 | 7.287613 | Vwa7 | 5.625549 |
| Guk1 | 7.262392 | Timm8b | 5.6092095 |
| AA465934 | 7.2209053 | Pet100 | 5.5675244 |
| Mcpt1 | 7.1459274 | Fam96a | 5.558428 |
| D130040H23Rik | 6.9918375 | Psma7 | 5.53758 |
| Gchfr | 6.9584966 | Ndufb2 | 5.525405 |
| D330045A20Rik | 6.802458 | A730063M14Rik | 5.513688 |
| Timp1 | 6.762784 | Snhg9 | 5.5063033 |
| Spp1 | 6.6851497 | Tomm5 | 5.494981 |
| Syce3 | 6.6169295 | Gm9926 | 5.4830647 |
| Mmp12 | 5.473943 | Gmfg | 4.95341 |
| Rpl41 | 5.463827 | Dbi | 4.946616 |
| 1110046J04Rik | 5.4621553 | Uqcrh | 4.9392786 |
| 5730408K05Rik | 5.4477134 | Cox7b | 4.9324193 |
| Tmem256 | 5.430485 | Dnajc15 | 4.927067 |
| Polr2k | 5.388984 | Tmem17 | 4.923312 |
| Insig1 | 5.3790574 | 1500011K16Rik | 4.9220147 |
| Immp1l | 5.3770976 | Mien1 | 4.9175024 |
| 1500012F01Rik | 5.373659 | Snrnp25 | 4.916217 |
| C1d | 5.3728213 | Rbp7 | 4.897103 |
| Myeov2 | 5.372405 | 4930415O20Rik | 4.8826404 |
| Uqcc2 | 5.3635793 | Rpl13a | 4.8343067 |
| Reg3d | 5.356067 | Gm6297 | 4.8270454 |
| Fam162a | 5.3559866 | 15-Sep | 4.813177 |
| Atp5k | 5.3249736 | Cyp51 | 4.805249 |

TABLE 6-continued

2'-FL Signature Response

| Genes | Fold Change (Pre- to Post-op) | Genes | Fold Change (Pre- to Post-op) |
|---|---|---|---|
| Gm14295 | 5.3051767 | Cbr3 | 4.7688994 |
| Uqcrq | 5.267751 | Gm20939 | 4.7585793 |
| Med21 | 5.2514105 | Commd6 | 4.744962 |
| Sec61g | 5.2194567 | Fam136a | 4.7376046 |
| Mrpl54 | 5.1961365 | Ndufb8 | 4.700318 |
| Rnd2 | 5.1744657 | Uqcr10 | 4.682153 |
| Ifrd1 | 5.1716685 | Chchd1 | 4.6808085 |
| Gt(ROSA)26Sor | 5.1703796 | Atp5l | 4.679488 |
| Prrx1 | 5.165311 | Lrp2bp | 4.670487 |
| Hrasls | 5.154323 | BC147527 | 4.670078 |
| Erich2 | 5.1460314 | 5033403H07Rik | 4.670078 |
| Ccl7 | 5.1269 | Hcrtr1 | 4.641202 |
| Sar1b | 5.099512 | 2310040G24Rik | 4.6380315 |
| Ndufb4 | 5.0829487 | Lrrc48 | 4.6338224 |
| Mgst2 | 5.061266 | Rpl17 | 4.6188574 |
| Tefm | 5.0467796 | Dkk4 | 4.6169024 |
| Bloc1s2 | 5.046474 | Sptssa | 4.6155534 |
| Tnfsf13 | 5.04074 | Ptrh1 | 4.615183 |
| BC035044 | 5.0402517 | Idi1 | 4.6092377 |
| Pdcd10 | 5.0402403 | Serpina3a | 4.6050606 |
| Ndufb6 | 5.0373144 | Cox16 | 4.5856004 |
| Ccdc90b | 5.0221066 | Dynlt1a | 4.5785227 |
| Pmvk | 5.0135884 | Slc51b | 4.575268 |
| Tstd1 | 5.0120335 | Phlda2 | 4.563902 |
| Mrpl14 | 5.00511 | LOC101055731 | 4.556948 |
| Stmnd1 | 5.0028076 | Commd2 | 4.5432124 |
| Gm15441 | 4.991624 | Rpl35a | 4.542264 |
| Rps27l | 4.9911604 | Cox14 | 4.5388374 |
| Hint3 | 4.975102 | Ndufa4 | 4.5291686 |
| Mgst3 | 4.9630594 | Lsm7 | 4.528298 |
| Mrps33 | 4.516323 | 1110034G24Rik | 4.268987 |
| 2010106C02Rik | 4.51394 | Pycard | 4.267532 |
| Tusc2 | 4.5015144 | Ccdc107 | 4.2636857 |
| 4933422H20Rik | 4.4994235 | Medag | 4.2618217 |
| Ndufb9 | 4.4957895 | Hddc2 | 4.255046 |
| Apoc4 | 4.485836 | Sdcbp2 | 4.252303 |
| Hint1 | 4.4824147 | 1700019L03Rik | 4.2511144 |
| Zswim7 | 4.4751177 | S100a6 | 4.2369013 |
| Rabl5 | 4.4482875 | Dgcr6 | 4.23661 |
| 1700020N01Rik | 4.446137 | Rilpl2 | 4.2352657 |
| Atp5j2 | 4.4449143 | Med11 | 4.234935 |
| 1810011O10Rik | 4.4428964 | 1810059H22Rik | 4.229534 |
| Smim6 | 4.424439 | Smim4 | 4.229385 |
| 3300005D01Rik | 4.4100385 | Hscb | 4.227304 |
| Dnah2 | 4.3921566 | Sec22a | 4.221071 |
| Gm6251 | 4.382552 | Rps25 | 4.2178516 |
| Wfdc17 | 4.381717 | Ndufb7 | 4.217327 |
| Casq1 | 4.3797865 | Cd320 | 4.215386 |
| Gm10433 | 4.3769193 | Hspb2 | 4.189284 |
| Dynlt1b | 4.3762574 | Ormdl1 | 4.184094 |
| Coa4 | 4.37474 | Gm10451 | 4.182007 |
| Rps15a-ps4 | 4.3724627 | Tm6sf1 | 4.1730814 |
| Rpl34 | 4.3699155 | 0610040B10Rik | 4.168404 |
| Rbp1 | 4.36435 | Dynlt1c | 4.1479883 |
| Ndufa7 | 4.3618383 | Fam216a | 4.146741 |
| Bambi-ps1 | 4.353083 | Atpif1 | 4.1447463 |
| Oaz1 | 4.3471713 | Pstk | 4.1416993 |
| Elof1 | 4.342603 | Gm5485 | 4.1393094 |
| Ndufaf5 | 4.338274 | Rps24 | 4.13081 |
| Ift20 | 4.336743 | Mpc2 | 4.127742 |
| Tnfsf11 | 4.335316 | Zfp433 | 4.119211 |
| Gm8274 | 4.3307257 | Sh2d1b1 | 4.1181784 |
| Rpa3 | 4.326587 | Clec11a | 4.1181784 |
| Rpl9 | 4.3226027 | Coa6 | 4.1180997 |
| Ppih | 4.322347 | Phgr1 | 4.1157846 |
| Sgcg | 4.3209896 | Clec4a4 | 4.112521 |
| 1110001J03Rik | 4.3182683 | Mvd | 4.1095605 |
| Ccdc122 | 4.317091 | Cript | 4.106506 |
| Rhebl1 | 4.3066297 | Ccdc142 | 4.101328 |
| Rhod | 4.3015037 | Uqcr11 | 4.100463 |
| Rpl35 | 4.2831683 | Rpl36 | 4.099126 |
| C330018D20Rik | 4.2796044 | Xlr | 4.0954247 |
| Nudt5 | 4.277685 | Fam221b | 4.0946984 |
| 6720489N17Rik | 4.273342 | 3110056K07Rik | 4.0925984 |

TABLE 6-continued

2'-FL Signature Response

| Genes | Fold Change (Pre- to Post-op) | Genes | Fold Change (Pre- to Post-op) | Genes | Fold Change (Pre- to Post-op) | Genes | Fold Change (Pre- to Post-op) |
|---|---|---|---|---|---|---|---|
| Rps14 | 4.2726626 | Prdx5 | 4.089377 | Alkbh7 | 3.6698294 | Ndufb3 | 3.5633318 |
| Mrpl11 | 4.0843887 | Cela1 | 3.9119165 | 2810001G20Rik | 3.6683493 | 2310009B15Rik | 3.5616167 |
| Mrpl12 | 4.0843306 | 0610007P14Rik | 3.908003 | Tma7 | 3.664375 | Mrpl46 | 3.5603695 |
| 1110001A16Rik | 4.081685 | Map2k3os | 3.9020815 | Hspe1 | 3.6640694 | Psmg4 | 3.5588083 |
| Lsmd1 | 4.0807924 | 1700123I01Rik | 3.900538 | Rpl5 | 3.662464 | Cox7c | 3.5568962 |
| Sc4mol | 4.0729136 | 2210407C18Rik | 3.8993602 | Smdt1 | 3.6616132 | Rps21 | 3.5568318 |
| Nudt7 | 4.071544 | Dynlt1f | 3.8889713 | Mrps18c | 3.6615586 | Tmsb10 | 3.553955 |
| Marcksl1-ps4 | 4.068557 | Tmem205 | 3.888747 | BC025446 | 3.6506467 | Bud31 | 3.5532992 |
| Nme2 | 4.0668707 | 2410015M20Rik | 3.8790472 | Gpx1 | 3.6475065 | Mterfd3 | 3.5499108 |
| Mvk | 4.0614204 | Gsta4 | 3.877381 | Mrp63 | 3.647295 | Abhd11os | 3.5492322 |
| Nudt14 | 4.06117 | Ghrl | 3.87218 | Phospho2 | 3.6468587 | Arf5 | 3.547803 |
| Gm10872 | 4.0493236 | 2010107G23Rik | 3.867532 | Rbm3 | 3.6466675 | 1600020E01Rik | 3.547719 |
| Ndufv2 | 4.047272 | Minos1 | 3.8648329 | Ndufa1 | 3.6404665 | Tmem126a | 3.546729 |
| Mrpl27 | 4.040231 | Rps7 | 3.8637013 | Hebp2 | 3.6346507 | Tmem14c | 3.542431 |
| Ssna1 | 4.0336494 | Rab9 | 3.8572958 | Cox6c | 3.6339245 | Sub1 | 3.5405016 |
| 9530052C20Rik | 4.033236 | Coq3 | 3.8543258 | Bbip1 | 3.630689 | Mrps36 | 3.5388138 |
| Cox7a2 | 4.0196576 | Spdya | 3.8535683 | Rdh16 | 3.6305258 | Cdkn2b | 3.5385904 |
| Gm4013 | 4.0138745 | Barx2 | 3.8516104 | Frmd8os | 3.537976 | Dpm3 | 3.4599342 |
| BC096441 | 4.0125637 | Pfdn5 | 3.849007 | Tmem120a | 3.535416 | Glod5 | 3.4523466 |
| Tmem208 | 4.011355 | Chchd6 | 3.847894 | Snrpe | 3.534698 | Khk | 3.451373 |
| Deb1 | 4.009011 | Med31 | 3.8477094 | Gm11627 | 3.5339854 | 2200002D01Rik | 3.4503496 |
| Pts | 3.997378 | Rpl22l1 | 3.8455873 | Cetn3 | 3.5317113 | Rpl32 | 3.4491684 |
| Mei1 | 3.9932103 | Prdx2 | 3.841748 | Gm15421 | 3.531105 | Gm20748 | 3.4460552 |
| Gm4787 | 3.9869359 | Cycs | 3.837267 | Gm3258 | 3.5294492 | Ifi27l2a | 3.443592 |
| Prap1 | 3.9812539 | Cmpk1 | 3.8336692 | H2afz | 3.5285115 | Anxa9 | 3.4409428 |
| Ociad2 | 3.9796128 | 1810022K09Rik | 3.8291261 | Bola2 | 3.524859 | Arsg | 3.4360607 |
| 2610044O15Rik8 | 3.9778166 | Apitd1 | 3.8260782 | Ccng2 | 3.5242922 | Csf2 | 3.4354722 |
| Smlr1 | 3.976706 | 1810037I17Rik | 3.822861 | Atox1 | 3.524113 | Akr1b8 | 3.4351058 |
| Atp6v0b | 3.974425 | Psmd14 | 3.8223858 | Myl4 | 3.5222642 | Jmjd7 | 3.4329875 |
| Vps29 | 3.9707558 | Ndufa2 | 3.8178277 | Atp5o | 3.5218987 | Mocs2 | 3.4304788 |
| Prss16 | 3.9681728 | Dph3 | 3.8169212 | Hnmt | 3.520993 | Chchd2 | 3.4287024 |
| B9d1 | 3.9678593 | A430005L14Rik | 3.813188 | Fbxl5 | 3.5170178 | Psmd10 | 3.4284284 |
| Gm6484 | 3.9622033 | Ndufs4 | 3.807048 | BC029214 | 3.5161948 | Lage3 | 3.425594 |
| Acyp1 | 3.9620159 | BC051226 | 3.8022168 | Snhg10 | 3.515769 | Idnk | 3.422531 |
| Mrpl41 | 3.9537487 | Mpc1 | 3.8016982 | Ndufa11 | 3.5146124 | Htatip2 | 3.4211614 |
| Lrrc51 | 3.9485974 | Churc1 | 3.800203 | Gm10069 | 3.51388 | Zfp2 | 3.4183106 |
| Spryd7 | 3.94847 | Romo1 | 3.7980874 | Tmem242 | 3.5134962 | Lsm1 | 3.4148033 |
| Cox4i1 | 3.9456635 | Arl1 | 3.796871 | Acot13 | 3.5104759 | Chpt1 | 3.4084725 |
| Serf2 | 3.9453354 | LOC100503676 | 3.7918305 | Nat2 | 3.50773 | Insig2 | 3.4078364 |
| 1500009L16Rik | 3.9388957 | Tmem141 | 3.78503 | Mgst1 | 3.5065954 | 0610009B22Rik | 3.407388 |
| Atf3 | 3.9379454 | Pigf | 3.7843397 | Atg4a-ps | 3.505213 | Pam16 | 3.4057934 |
| Hsd11b1 | 3.9294748 | Iyd | 3.776449 | 5033411D12Rik | 3.5052059 | Arl4a | 3.4048054 |
| Dctpp1 | 3.9249203 | Smim20 | 3.7692003 | Atp5f1 | 3.5045538 | Ndufab1 | 3.4039354 |
| BC002163 | 3.924025 | Tomm40l | 3.7670097 | Rps27a | 3.5045276 | Dbndd2 | 3.4024577 |
| Ssr4 | 3.9177623 | Oas1c | 3.7610757 | Gin1 | 3.5036402 | Atg5 | 3.4022467 |
| Ndufs5 | 3.9150894 | 2010107E04Rik | 3.7595193 | Adh6a | 3.499855 | Pomp | 3.3980699 |
| Tspo2 | 3.7585492 | Nudt8 | 3.6304493 | Art2a-ps | 3.4935386 | Commd1 | 3.3970575 |
| Rmdn1 | 3.7567465 | Sdhd | 3.6296287 | Lamtor5 | 3.4930997 | Ptges3l | 3.395808 |
| Tomm20 | 3.750628 | Stk16 | 3.628363 | Apoc3 | 3.4912055 | Nudcd2 | 3.3937488 |
| 1700024P16Rik | 3.748312 | Gtf2a2 | 3.625132 | 1700066M21Rik | 3.4868617 | Bri3 | 3.392808 |
| Oxld1 | 3.7429264 | Pdcd6 | 3.6215408 | Pcbd2 | 3.4829736 | Ndufaf6 | 3.3926394 |
| Bet1 | 3.7404535 | Slirp | 3.6210694 | Bad | 3.480909 | Lsm3 | 3.3897974 |
| Mrps16 | 3.7403965 | Dusp19 | 3.6079843 | Mrpl24 | 3.478746 | Mrps24 | 3.3892732 |
| Crip1 | 3.7367299 | Agbl3 | 3.601981 | Cisd1 | 3.4776886 | Mrpl28 | 3.3892148 |
| Fahd2a | 3.7346845 | Stra13 | 3.5996208 | Sirt3 | 3.476838 | 1110059E24Rik | 3.3863382 |
| Myl7 | 3.7329671 | 2010315B03Rik | 3.5992854 | Fopnl | 3.4759912 | Rgs17 | 3.3854337 |
| Pih1d2 | 3.7292542 | 1700007L15Rik | 3.59756 | Rplp0 | 3.4701855 | Rbp2 | 3.3834207 |
| Gm10012 | 3.7289279 | Fbxw9 | 3.5974886 | Akr1c12 | 3.4689095 | Prdx1 | 3.3813324 |
| Gabarapl2 | 3.7192447 | Tmem29 | 3.5959547 | Gstt2 | 3.4679153 | Thoc7 | 3.3812966 |
| Mycbpap | 3.7088478 | S100a1 | 3.5933428 | Tmem167 | 3.4653878 | Cbr1 | 3.380513 |
| Rps10 | 3.7083945 | Rps3 | 3.5900042 | Tceb1 | 3.46362 | Fau | 3.3792768 |
| Ptpmt1 | 3.7068653 | Hist1h2bc | 3.5881894 | Trappc2l | 3.4605398 | Vti1b | 3.377168 |
| Tm2d1 | 3.7037346 | Rps12 | 3.5854213 | Aldh1a1 | 3.377019 | Chrna1 | 3.2954175 |
| Cd302 | 3.7015936 | Ereg | 3.5847306 | Mrpl13 | 3.375623 | Hist1h2ba | 3.2942517 |
| Ppp1r14d | 3.7009626 | Dcun1d5 | 3.5814614 | Plac9b | 3.370909 | Tmem147 | 3.2939303 |
| Calml4 | 3.698567 | Dnajc19 | 3.5782223 | Plac9a | 3.370909 | Glrx3 | 3.2930737 |
| Sec61b | 3.6902537 | Urm1 | 3.5757036 | Gm9780 | 3.370909 | Ube2t | 3.2887106 |
| Eif4a2 | 3.6898928 | Cox6b1 | 3.5737221 | 2810008D09Rik | 3.3702745 | 2410018M08Rik | 3.2865233 |
| Coa3 | 3.6875594 | Car4 | 3.572675 | Rap1b | 3.368019 | Casp6 | 3.2837499 |
| Coprs | 3.6814995 | Actr6 | 3.5712993 | Tmem243 | 3.3677986 | C330022C24Rik | 3.283687 |
| Gstm4 | 3.6814702 | Tbca | 3.5678298 | Fis1 | 3.365829 | Gm14207 | 3.2807858 |
| Gng11 | 3.6788304 | Rpl12 | 3.567502 | Nt5c | 3.3631854 | Mkks | 3.279587 |
| Psma6 | 3.670204 | Higd1a | 3.5668323 | Rpl11 | 3.3630352 | Cox6a1 | 3.276204 |
| Rhoc | 3.6699429 | Adprm | 3.566585 | Reg1 | 3.3622527 | Smim8 | 3.2759259 |

TABLE 6-continued

2'-FL Signature Response

| Genes | Fold Change (Pre- to Post-op) | Genes | Fold Change (Pre- to Post-op) | Genes | Fold Change (Pre- to Post-op) | Genes | Fold Change (Pre- to Post-op) |
|---|---|---|---|---|---|---|---|
| Cnih1 | 3.3586035 | Mcfd2 | 3.2748985 | Gm20559 | 3.1799858 | Apopt1 | 3.110317 |
| 2010010A06Rik | 3.358349 | Ddt | 3.2717464 | Timm10 | 3.1768801 | Gm15401 | 3.1087332 |
| Pfdn1 | 3.3579636 | Aldh1a7 | 3.2703896 | Psma3 | 3.1767964 | Dusp14 | 3.100091 |
| Sla2 | 3.3546937 | Rbm7 | 3.2703564 | Casp4 | 3.1760414 | Abhd17a | 3.0944982 |
| Sepw1 | 3.3540747 | Rps18 | 3.2694192 | Nubp1 | 3.0931432 | Ptgis | 3.0301259 |
| Vamp8 | 3.352907 | Rasl2-9 | 3.2671046 | Nhp2 | 3.092994 | Cetn2 | 3.0298786 |
| Nat8 | 3.352171 | Rpl19 | 3.2664082 | Lamtor1 | 3.0929098 | Echs1 | 3.0280921 |
| Spa17 | 3.350083 | Igj | 3.2641342 | Serhl | 3.090854 | Commd8 | 3.0273046 |
| Plac8 | 3.3446345 | Gtf2h5 | 3.262752 | Ndufs8 | 3.089257 | C330013E15Rik | 3.0262513 |
| Pla2g12b | 3.3437746 | Prorsd1 | 3.2581737 | C1ql3 | 3.0892384 | Sult1d1 | 3.0240126 |
| Lyrm2 | 3.3430162 | Sun3 | 3.2571268 | Hist2h2aa2 | 3.081118 | Dpy30 | 3.0217187 |
| Ifitm6 | 3.342575 | Ict1 | 3.2546237 | Lekr1 | 3.0779405 | Ndufb10 | 3.0192056 |
| Gm5617 | 3.3393013 | Fdx1 | 3.2525601 | Endog | 3.0778866 | Rps9 | 3.0180128 |
| Hagh | 3.3373187 | Rpl39 | 3.2523634 | Mrps23 | 3.0778031 | Nme3 | 3.017964 |
| Pthlh | 3.3349125 | Ran | 3.2513626 | Tvp23a | 3.0774145 | 2810013P06Rik | 3.0176237 |
| Cox19 | 3.331135 | Mrps28 | 3.2493541 | Cd3d | 3.0767117 | Eif3h | 3.0163243 |
| Ugt2b35 | 3.3307369 | Slc6a3 | 3.2488563 | Rps8 | 3.0762024 | Sod1 | 3.0133636 |
| Nr1i3 | 3.3282504 | Gm2382 | 3.2483294 | Klhl9 | 3.0735815 | 1110008F13Rik | 3.012545 |
| Ebpl | 3.3278725 | Atp6v1g1 | 3.247866 | Atp5j | 3.0726945 | Mal2 | 3.0123682 |
| 1190002F15Rik | 3.3270686 | Cck | 3.2458475 | Fdxacb1 | 3.071525 | Haus7 | 3.0117428 |
| Tomm7 | 3.3202686 | Snrpd2 | 3.2453558 | Sumo1 | 3.0711617 | Mrpl34 | 3.0068102 |
| Pafah1b3 | 3.3184855 | Triqk | 3.242175 | 2210404O09Rik | 3.0709414 | Slfn2 | 3.0053267 |
| Trub2 | 3.3133502 | 3110040N11Rik | 3.2334318 | Lsm5 | 3.0686824 | Prkrip1 | 3.0046287 |
| Atp5h | 3.3124814 | Rps15 | 3.2328143 | Tatdn3 | 3.064178 | Mff | 3.0042667 |
| Sectm1a | 3.310934 | Ndufa5 | 3.2327724 | Immp2l | 3.0618308 | Hist1h2bf | 3.0019574 |
| 1110008P14Rik | 3.3096504 | LOC100503295 | 3.231871 | Immp2l | 3.0605798 | Slc35d2 | 3.0017087 |
| 2310011J03Rik | 3.3085678 | 1110065P20Rik | 3.2311847 | Psmb9 | 3.058844 | Rpl27a | 3.0011718 |
| Vmp1 | 3.3074524 | Polr1d | 3.2307022 | Gm9895 | 3.0570443 | Sdf2 | 3.00101 |
| Tgds | 3.3067267 | Tmem261 | 3.2290423 | Atp6v0e | 3.0541134 | Map3k5 | -3.0020726 |
| C1qtnf4 | 3.3022997 | Kbtbd3 | 3.227809 | Snrpd1 | 3.0533085 | Vars | -3.0022135 |
| H3f3a | 3.301596 | Atg12 | 3.2273695 | Mea1 | 3.052453 | Sall1 | -3.0022635 |
| Fdps | 3.2983522 | Eef1b2 | 3.2266586 | Vcpkmt | 3.052408 | Agbl5 | -3.0033512 |
| Nr1h3 | 3.2960114 | Rps11 | 3.2251387 | Ndufa6 | 3.0500488 | Sh3bp4 | -3.0042028 |
| Il18 | 3.2236009 | Timm10b | 3.175424 | Psma5 | 3.049309 | Ncoa3 | -3.005688 |
| Tcta | 3.2227125 | Rpl10a | 3.1753023 | Gm14057 | 3.048015 | Tead4 | -3.006273 |
| Ubxn6 | 3.220703 | Hist1h2bp | 3.1722658 | Lypla1 | 3.048012 | Hlcs | -3.007877 |
| Snrpg | 3.2205303 | Pla2g16 | 3.1713479 | Scoc | 3.0462081 | Tsc2 | -3.008184 |
| Tmem160 | 3.219463 | Crot | 3.167718 | Tubal3 | 3.046013 | Arhgap11a | -3.008637 |
| Uxt | 3.2193577 | Pold4 | 3.1675038 | 2410006H16Rik | 3.0433002 | Myh10 | -3.0089598 |
| Polr2j | 3.2189968 | Acot12 | 3.166188 | Tcrg-V7 | 3.0419424 | Ankrd13b | -3.009658 |
| Cyb5 | 3.218755 | Bola1 | 3.164679 | Zfp647 | 3.040848 | Fam83h | -3.0098403 |
| S100a4 | 3.217675 | Tnnt1 | 3.1644328 | Psmb6 | 3.0400455 | Safb | -3.0118165 |
| Cxcl16 | 3.215844 | S100a16 | 3.164077 | Gch1 | 3.039039 | Rnf123 | -3.0156345 |
| Rps13 | 3.2142391 | Hist1h2bb | 3.1627207 | Rab17 | 3.0389378 | Ptger1 | -3.0164857 |
| Rps27 | 3.2141616 | Mettl23 | 3.1614387 | 2410004B18Rik | 3.037604 | Ocrl | -3.0166333 |
| Mmp23 | 3.2127616 | Hist1h2bg | 3.159531 | Zfand2b | 3.034227 | Traf3 | -3.0203717 |
| Ccdc28a | 3.2101393 | Ceacam10 | 3.1586473 | Commd3 | 3.0318627 | Sorbs3 | -3.0209057 |
| Mob4 | 3.2083678 | Psme2 | 3.1558945 | Med28 | 3.0316966 | Glp2r | -3.0217009 |
| Ccdc58 | 3.2082965 | Cklf | 3.1551805 | Tagln | 3.03035 | Zcchc14 | -3.022241 |
| Hist1h2bq | 3.2052646 | 1700011J10Rik | 3.1530848 | Eppk1 | -3.0235007 | Mapre2 | -3.0822885 |
| P2ry10 | 3.203865 | Mtfr1 | 3.152518 | Elac2 | -3.023771 | Chrm1 | -3.0857024 |
| Hist1h2bj | 3.202875 | Mzt1 | 3.1486738 | Kcnh3 | -3.0239713 | Kif18b | -3.0882776 |
| Xcl1 | 3.2017045 | E030024N20Rik | 3.1483626 | Simc1 | -3.0239716 | Tnks | -3.0890706 |
| Erh | 3.2009733 | Pex2 | 3.1472304 | Grrp1 | -3.0247173 | Foxo4 | -3.0909917 |
| Gm12511 | 3.1990347 | Rnf7 | 3.1464407 | Vcl | -3.0254452 | Insm1 | -3.0912166 |
| Hist1h2br | 3.1986375 | Lyrm5 | 3.1460083 | Ylpm1 | -3.0271857 | Iffo2 | -3.0926178 |
| Ndufaf2 | 3.1974425 | Dtd2 | 3.1431317 | Myo1b | -3.0284219 | Ccnd2 | -3.093455 |
| S100a10 | 3.1967392 | Cyp2r1 | 3.1427584 | Arsb | -3.0289369 | Itsn1 | -3.0947387 |
| Acbd4 | 3.196085 | Cenpw | 3.13941 | Fbf1 | -3.0305462 | Fam115a | -3.0952141 |
| Cox17 | 3.195562 | Hist1h2bl | 3.1367228 | Fndc5 | -3.0305884 | Hhatl | -3.0964913 |
| Cystm1 | 3.1950765 | Rps19 | 3.1363246 | Dpp9 | -3.0329862 | Tmem2 | -3.0978527 |
| Fam132a | 3.193759 | Gm12657 | 3.1320236 | Il2rg | -3.036746 | Irak3 | -3.0991771 |
| Myl6 | 3.1927085 | Hist1h4i | 3.1287484 | Stim1 | -3.0381591 | Camsap1 | -3.1014283 |
| Mzb1 | 3.1920977 | Hmbs | 3.1281512 | Brpf3 | -3.0400147 | Tbc1d9b | -3.1015904 |
| A930015D03Rik | 3.1916633 | LOC100505179 | 3.1263034 | Itgb7 | -3.0420604 | Zkscan8 | -3.103521 |
| Hist1h2bh | 3.1901064 | Gng10 | 3.1241057 | Plekhg1 | -3.0425673 | Ube2o | -3.1044157 |
| Rpl27 | 3.189822 | Cox7a2l | 3.123006 | Zfp871 | -3.0448644 | Tm9sf4 | -3.1063747 |
| Polr2i | 3.1893945 | Cst6 | 3.121027 | Plcb2 | -3.0460985 | Igf2bp2 | -3.1067445 |
| Ly6g6f | 3.1860645 | Lsm4 | 3.1202157 | Tmem63a | -3.0462244 | Usp48 | -3.1110376 |
| Hdhd3 | 3.1857402 | Zfp53 | 3.119412 | Mid1 | -3.0475676 | Celf3 | -3.1154883 |
| Hist1h2bm | 3.1855896 | Smim15 | 3.1178117 | Prrt2 | -3.0491812 | Samd14 | -3.1170206 |
| Cenpa | 3.1831837 | Ndufc1 | 3.112162 | A4gnt | -3.0491817 | Mfsd6 | -3.1174235 |
| Ccl12 | 3.1831615 | Gm13446 | 3.112128 | Tpp1 | -3.0503604 | Bach2os | -3.118038 |
| Wdpcp | 3.181735 | Fam96b | 3.1118205 | Cspg4 | -3.0523267 | Znfx1 | -3.1199987 |

TABLE 6-continued

2'-FL Signature Response

| Genes | Fold Change (Pre- to Post-op) | Genes | Fold Change (Pre- to Post-op) | Genes | Fold Change (Pre- to Post-op) | Genes | Fold Change (Pre- to Post-op) |
|---|---|---|---|---|---|---|---|
| Kif12 | −3.055565 | Usp36 | −3.1200933 | Dennd1c | −3.312244 | Spred2 | −3.3806496 |
| Pole | −3.0571873 | Usp11 | −3.120745 | Bcl11b | −3.3124213 | Gna12 | −3.3819816 |
| Gli1 | −3.0572908 | Ttll5 | −3.1213777 | Pip4k2b | −3.316574 | Rapgef1 | −3.3820071 |
| Usp43 | −3.0575101 | Myo5a | −3.1238954 | Cd300lg | −3.3181157 | Ino80 | −3.3822517 |
| 8-Sep | −3.0584426 | Als2 | −3.1262133 | BC021891 | −3.3188012 | Slc26a2 | −3.3845513 |
| Zkscan17 | −3.0606449 | Dmtn | −3.1264732 | Gtf3c1 | −3.3224137 | Gfod1 | −3.385178 |
| Snapc4 | −3.0609922 | Kcnq1ot1 | −3.1275516 | Hspg2 | −3.3234692 | Smarcc1 | −3.3857787 |
| Camsap2 | −3.0631297 | Rgp1 | −3.1283731 | Ints9 | −3.325528 | Gns | −3.3908603 |
| Slc2a10 | −3.0655406 | Erc1 | −3.1290927 | Adam12 | −3.3267465 | Ppp1r12a | −3.393221 |
| Qser1 | −3.0659401 | Cdc42bpg | −3.1305099 | Ehd3 | −3.3273013 | Sox4 | −3.3932478 |
| Trpc4 | −3.0675054 | Fat1 | −3.1316473 | Ppp2r2c | −3.3278549 | Dip2c | −3.3956358 |
| Ncoa1 | −3.067747 | Nfatc4 | −3.1341817 | Sf3b3 | −3.3283467 | Ppm1l | −3.3988905 |
| Map4 | −3.068253 | Cblb | −3.1355562 | Cped1 | −3.3287168 | Bmp6 | −3.3990114 |
| Efna5 | −3.0685537 | Fbrs | −3.1361158 | Ccnk | −3.3287828 | Rai1 | −3.399646 |
| Cramp1l | −3.06957 | Fyb | −3.1365278 | Plbd2 | −3.329498 | Sema6a | −3.399786 |
| Llgl1 | −3.0721898 | Acvr2b | −3.1389143 | Fzd3 | −3.3337612 | Orm1 | −3.3998487 |
| Plagl2 | −3.0729702 | Kit | −3.1474662 | Spry1 | −3.3399081 | Rgs12 | −3.4048998 |
| Cgn | −3.0736747 | Rexo1 | −3.1487596 | Pltp | −3.3402333 | Atp2a3 | −3.4052458 |
| Cpt1a | −3.0751243 | Ephb2 | −3.1487758 | Cacng7 | −3.3429463 | Proser1 | −3.4070573 |
| Copa | −3.0805163 | Fam171a1 | −3.149028 | Sympk | −3.344075 | Asap2 | −3.4089835 |
| Chst1 | −3.1504972 | Mbp | −3.221309 | Mxra8 | −3.3466833 | Tram2 | −3.4110854 |
| Il2ra | −3.1551785 | Man2b1 | −3.2214227 | Ssbp3 | −3.3471336 | B4galnt4 | −3.4191854 |
| Ly75 | −3.1552887 | Esrp2 | −3.2239873 | Sncaip | −3.3524659 | Eng | −3.4192147 |
| Ticrr | −3.1597023 | Fam222b | −3.2264998 | Dhx34 | −3.352613 | Gtse1 | −3.4197483 |
| Il17re | −3.161177 | Ctnnd1 | −3.2270815 | Lmf2 | −3.3531837 | Stk32a | −3.422598 |
| Crispld2 | −3.16234 | Polr1a | −3.2271206 | Tert | −3.35584 | Sox6 | −3.4241712 |
| Lrp4 | −3.1663153 | Slc12a4 | −3.229783 | Bace1 | −3.3574953 | Cfd | −3.424793 |
| Dzip1 | −3.1691394 | Rps6ka3 | −3.2300725 | Tub | −3.3585992 | Iqsec2 | −3.4304843 |
| Chadl | −3.171233 | Itgb3 | −3.2309468 | Ap2a1 | −3.3586602 | Madd | −3.4315333 |
| App | −3.1715465 | Pip5k1c | −3.2349064 | Slc44a2 | −3.359958 | Ceacam1 | −3.4346342 |
| Col6a1 | −3.1720002 | Sltm | −3.235045 | Stard13 | −3.3621497 | Clstn2 | −3.4367335 |
| Mcf2l | −3.1738975 | Mrvi1 | −3.2354243 | Slc38a3 | −3.3630846 | Pbx3 | −3.4367342 |
| Dennd1a | −3.1742208 | Dclk1 | −3.2398963 | Abcc1 | −3.3635278 | Cnnm3 | −3.4369743 |
| Ptpn9 | −3.1749165 | Sox5 | −3.240239 | Slc27a1 | −3.3649423 | Smc1a | −3.439649 |
| St3gal2 | −3.1784637 | Slc7a1 | −3.2429357 | Sh3rf1 | −3.3670368 | Chpf | −3.439913 |
| Gm3230 | −3.1791387 | Lct | −3.2438145 | Cp | −3.3691866 | Enpp6 | −3.4413233 |
| Pelp1 | −3.1799726 | Glul | −3.2455862 | Apba2 | −3.4413238 | Hpcal4 | −3.5253482 |
| Dock1 | −3.1805909 | Gsk3b | −3.251327 | Macc1 | −3.441324 | Nrip2 | −3.5254579 |
| Ercc2 | −3.182226 | Atp10a | −3.2521956 | Bicc1 | −3.4427848 | Aqr | −3.5279844 |
| Numa1 | −3.182554 | Nup214 | −3.2535243 | Zfp704 | −3.445937 | Rcan2 | −3.529663 |
| Col5a3 | −3.1846642 | Arid5a | −3.253791 | Gm21553 | −3.4485805 | Slc52a3 | −3.5307436 |
| Elk3 | −3.1848805 | Zfp553 | −3.2578642 | Fosl2 | −3.4500785 | Pik3r5 | −3.531263 |
| Klf3 | −3.1854932 | Arhgef10l | −3.257994 | Pcdhga3 | −3.450209 | Acin1 | −3.5332682 |
| Atp2a2 | −3.1859634 | Rnf26 | −3.258163 | A430048K04Rik | −3.4573383 | Wscd1 | −3.5383573 |
| Rad54l2 | −3.187921 | Flii | −3.2588305 | Sipa1l2 | −3.457526 | Slfn8 | −3.5401933 |
| Myrf | −3.1901155 | Igsf9b | −3.2599583 | Wfs1 | −3.4577177 | Cbx6 | −3.5403223 |
| Kcna5 | −3.1916084 | Wdr81 | −3.2612648 | Mvb12b | −3.4587219 | Asic2 | −3.5426505 |
| Xylb | −3.1917624 | Atxn2 | −3.262126 | Fmnl3 | −3.4595995 | Phf8 | −3.5440848 |
| Clstn1 | −3.195237 | Tll1 | −3.2638414 | Trrap | −3.4611585 | Pds5a | −3.5460124 |
| Pfkfb3 | −3.1968427 | Smg6 | −3.2693381 | Wipf2 | −3.4649026 | Peli2 | −3.5464203 |
| Smarca4 | −3.1991322 | Zbtb4 | −3.273273 | Arfgef2 | −3.467604 | Szt2 | −3.548842 |
| Nbea | −3.2025425 | Zfp398 | −3.276649 | Prdm2 | −3.4696872 | Scnn1a | −3.5508385 |
| Col28a1 | −3.2030636 | Havcr2 | −3.2769685 | Ikzf2 | −3.471778 | Clca1 | −3.5537283 |
| Nos1 | −3.2030911 | Nsf | −3.2782152 | Grn | −3.4719632 | Kmt2b | −3.5550706 |
| Tek | −3.2035434 | Ncl | −3.2826457 | Dhx8 | −3.473971 | Pcdhga1 | −3.5570645 |
| Ints1 | −3.2036636 | Mlph | −3.2827647 | Dopey2 | −3.473979 | 6430548M08Rik | −3.5590043 |
| Hs6st1 | −3.204002 | Dock5 | −3.2842026 | Nbr1 | −3.47411 | Ampd2 | −3.5602858 |
| Ncoa6 | −3.2072992 | Dhdh | −3.284631 | Taf15 | −3.4750698 | Spata13 | −3.562386 |
| Nfat5 | −3.2121406 | Pi4ka | −3.286215 | Pkd2 | −3.478211 | Phactr1 | −3.5663443 |
| Tbc1d9 | −3.2133777 | Tet1 | −3.291508 | Xpo5 | −3.4826427 | Mark1 | −3.5663443 |
| Slc12a7 | −3.2137733 | Sbf2 | −3.2942991 | Hcfc1 | −3.4831636 | Hipk2 | −3.5667038 |
| Mink1 | −3.2142534 | Zbed3 | −3.297465 | Mast2 | −3.4846668 | Itga9 | −3.5689063 |
| Lrp8 | −3.2149615 | Phf3 | −3.2983792 | Pogz | −3.4849987 | Map1a | −3.5706897 |
| Slc35d3 | −3.2187114 | Arid3a | −3.2993932 | Braf | −3.4865203 | Trps1 | −3.5745804 |
| Rfx2 | −3.2208707 | Mlxip | −3.3002846 | Farp2 | −3.490377 | Farp1 | −3.5781984 |
| Sart1 | −3.3014445 | Abcc4 | −3.3695242 | Lpcat1 | −3.4904416 | Xrn1 | −3.5813835 |
| Plxdc1 | −3.3044188 | Darc | −3.3705246 | Nup210 | −3.4927437 | Chst14 | −3.5817165 |
| Ipo9 | −3.3062513 | Etl4 | −3.372149 | Antxr1 | −3.4952302 | Arhgap31 | −3.5841453 |
| Extl3 | −3.3078992 | Pcdhga12 | −3.3721926 | Dsp | −3.4962633 | BC043934 | −3.5866683 |
| Jph4 | −3.3088315 | Atxn1l | −3.3726687 | Ntn1 | −3.4970722 | Xpo6 | −3.586813 |
| Tgfb1 | −3.3088923 | Eif4g1 | −3.3745375 | Dlgap3 | −3.4990947 | Gpr1c | −3.5950077 |
| Sec31a | −3.3094733 | Dnm2 | −3.3764126 | Nid1 | −3.5043943 | B130055M24Rik | −3.600321 |
| Sdc3 | −3.3104954 | Gbf1 | −3.377503 | Scaf4 | −3.507997 | Sema4c | −3.600328 |
| Pacs2 | −3.3110354 | Kdm5c | −3.378133 | Plod1 | −3.5096967 | Wwc2 | −3.6007683 |

TABLE 6-continued

2'-FL Signature Response

| Genes | Fold Change (Pre- to Post-op) | Genes | Fold Change (Pre- to Post-op) | Genes | Fold Change (Pre- to Post-op) | Genes | Fold Change (Pre- to Post-op) |
|---|---|---|---|---|---|---|---|
| Gm608 | -3.5139318 | Paqr3 | -3.6038818 | Runx1t1 | -3.8461158 | Kcnc1 | -3.997205 |
| Pygb | -3.5162807 | Eya1 | -3.605546 | Dapk1 | -3.8510735 | Sema6c | -4.005463 |
| Sort1 | -3.516864 | Myadm | -3.606445 | Lhfpl4 | -3.865108 | Pde2a | -4.0090804 |
| Gsn | -3.5169852 | Dst | -3.6080844 | Fus | -3.8655748 | Dnah8 | -4.012101 |
| Zc3h13 | -3.523498 | Fam193a | -3.609822 | Arhgef40 | -3.8658917 | Siglece | -4.0160804 |
| Map4k2 | -3.5240316 | Dab2ip | -3.610647 | Ddr2 | -3.873039 | Adrbk2 | -4.0170226 |
| Ern1 | -3.5251977 | Foxj2 | -3.611917 | Synj2 | -3.8795857 | Itih5 | -4.0178256 |
| Dlg5 | -3.612822 | 9930021J03Rik | -3.7021093 | Rnf44 | -3.881643 | Lhx6 | -4.0196285 |
| Kat6a | -3.6136205 | Zfp628 | -3.7040431 | Fryl | -3.8850935 | Prkar1b | -4.0241795 |
| Agap1 | -3.6147504 | Lcp1 | -3.7044704 | Mast4 | -3.8879266 | Zan | -4.0249963 |
| Pcdhga8 | -3.6162553 | Sun2 | -3.705175 | Nckap1l | -3.8922083 | Fbxl7 | -4.0249968 |
| Arhgap32 | -3.6182532 | Pak6 | -3.7059443 | Hdac7 | -3.8924627 | Pik3cg | -4.0295277 |
| Gltscr1l | -3.621261 | 4933417A18Rik | -3.7060876 | Ubap2l | -3.8952832 | A530020G20Rik | -4.0297756 |
| Ago1 | -3.6226287 | Vldlr | -3.7076874 | Cul9 | -3.8966796 | Dot1l | -4.03153 |
| Cux2 | -3.622773 | Kank2 | -3.7084403 | Cntn1 | -3.8988085 | Pcdhgc4 | -4.0340695 |
| Gpr126 | -3.6248188 | Supt6 | -3.7089944 | Pcdha2 | -3.9060335 | 4833432E10Rik | -4.0356417 |
| Csf1 | -3.6268225 | 4-Mar | -3.7091248 | Tcf7 | -3.907541 | Cers6 | -4.0363693 |
| Rfx1 | -3.628195 | Nfatc1 | -3.7097428 | Mrap | -3.915371 | Itga11 | -4.037414 |
| Wdfy3 | -3.6286135 | Pard3b | -3.7101946 | Cyyr1 | -3.9175227 | Setd2 | -4.038532 |
| Tmem201 | -3.6287882 | Grb10 | -3.710719 | Srrm2 | -3.9230103 | Sgtb | -4.0407844 |
| Fbxo32 | -3.6301525 | Prex1 | -3.7153468 | Klf5 | -3.9269304 | Cnot3 | -4.0416946 |
| Pcdhga11 | -3.6307678 | Rnf145 | -3.7179437 | Gm17644 | -3.9308157 | Myo1f | -4.0462036 |
| Fbxo42 | -3.6324549 | Irs1 | -3.721594 | Eml2 | -3.93305 | Mef2d | -4.04646 |
| Tchh | -3.6392055 | Col15a1 | -3.7220936 | Map3k9 | -4.0467887 | F830016B08Rik | -4.1309 |
| Map1s | -3.6411023 | Pcdhga7 | -3.723701 | Col6a4 | -4.0480375 | Lcor | -4.132236 |
| Ocstamp | -3.6423874 | Rasgrp3 | -3.7265992 | Wnt2b | -4.048786 | Slc10a6 | -4.135364 |
| Neurl1a | -3.6461504 | Camsap3 | -3.731904 | S1pr3 | -4.0495124 | Myo1d | -4.139379 |
| Eef2k | -3.6480718 | Pcdhga2 | -3.7322114 | Shroom3 | -4.0511737 | Myo1d | -4.144757 |
| Pkd1 | -3.649904 | Chrnb2 | -3.7370374 | Nid2 | -4.054951 | 9530026P05Rik | -4.1470394 |
| Zfp592 | -3.6545382 | Kcnn3 | -3.7397006 | Lamc3 | -4.0553217 | Rgl1 | -4.147127 |
| Zfyve26 | -3.6556888 | Smarca2 | -3.7480974 | Astn2 | -4.06034 | Pcdhgb6 | -4.1491647 |
| Tbc1d2b | -3.6596959 | Plvap | -3.7562704 | Pyy | -4.066705 | Atp13a2 | -4.150653 |
| Pld4 | -3.6627781 | Tigd5 | -3.7567062 | Abl1 | -4.067037 | Ppp1r9b | -4.15373 |
| Slco2a1 | -3.6634712 | Slco3a1 | -3.761777 | Nol6 | -4.067434 | Prpf8 | -4.160904 |
| Ccbe1 | -3.664766 | Tnfrsf19 | -3.7657285 | Dnase1l3 | -4.067944 | Tacc2 | -4.161365 |
| Hnf1a | -3.6663907 | Lrig3 | -3.7660775 | Satb1 | -4.0682206 | Bgn | -4.1619368 |
| Arhgef12 | -3.6683536 | Npnt | -3.768393 | Sp2 | -4.0727754 | Duox1 | -4.168964 |
| Ctc1 | -3.6687658 | Uhrf1bp1 | -3.7745569 | Cep164 | -4.0787563 | Dnajc16 | -4.169465 |
| Pik3r1 | -3.6692247 | Mmp14 | -3.776523 | Slc25a23 | -4.0795193 | Eml6 | -4.1713467 |
| Rassf8 | -3.6712968 | Rimbp2 | -3.7766013 | Rnf39 | -4.0801406 | Mapk7 | -4.1765256 |
| Ltk | -3.6712968 | Plxna1 | -3.7770166 | Nefm | -4.085786 | Wnk4 | -4.1777415 |
| Mab21l2 | -3.67398 | Cacnb1 | -3.777234 | Ern2 | -4.085957 | Kat6b | -4.17779 |
| Sf1 | -3.6781216 | C2cd3 | -3.7775476 | Golga4 | -4.0879183 | LOC100503956 | -4.187942 |
| Sik3 | -3.6814513 | Pml | -3.7785082 | Bend5 | -4.095315 | Iqgap3 | -4.188123 |
| Myof | -3.6855872 | Itga4 | -3.7798607 | Fgfr4 | -4.096144 | Safb2 | -4.1951475 |
| 9430020K01Rik | -3.6900547 | Tacr2 | -3.7840707 | Megf6 | -4.0971327 | Kmt2e | -4.1983366 |
| Megf9 | -3.6904507 | Ets1 | -3.789067 | Taok3 | -4.0990605 | Smarcc2 | -4.201095 |
| Apc | -3.6933367 | Emilin1 | -3.789171 | Kdm2a | -4.1019144 | Sh3pxd2b | -4.2025847 |
| Trabd2b | -3.696617 | Myo1e | -3.7917228 | Ece1 | -4.105552 | Cnnm1 | -4.202585 |
| Dmp1 | -3.697096 | Actn1 | -3.7937815 | Fbxl16 | -4.1071024 | Larp1 | -4.204811 |
| Reck | -3.6972272 | Maml1 | -3.798721 | Cpne4 | -4.10729 | Ppard | -4.206696 |
| Sh3kbp1 | -3.7002585 | zfp777 | -3.8008387 | Kif26b | -4.10729 | Zfp78 | -4.207849 |
| Hnrnpul1 | -3.8014574 | Osbpl7 | -3.933423 | Snx29 | -4.1086183 | Gab2 | -4.212853 |
| Plekhm1 | -3.8031092 | Strn | -3.9340444 | Man2a2 | -4.109705 | Zfp385a | -4.213635 |
| Irf2bp1 | -3.8036022 | Zfp39 | -3.9348488 | Npr2 | -4.1111894 | Taf3 | -4.214854 |
| Caskin2 | -3.8042371 | Mmp2 | -3.9379535 | Sobp | -4.113141 | Myo7b | -4.2153554 |
| Bptf | -3.8054695 | Rreb1 | -3.939714 | BC031361 | -4.113771 | Drosha | -4.2159386 |
| Tie1 | -3.806474 | Smad3 | -3.9429595 | Zbtb7a | -4.11611 | Pcp2 | -4.2183514 |
| Pbx1 | -3.8075013 | Numbl | -3.9467473 | Dnmt3a | -4.1206045 | Lamc1 | -4.2192445 |
| Msn | -3.8085234 | Maml2 | -3.9547844 | Hap1 | -4.1230197 | Gm15800 | -4.2289042 |
| Chd4 | -3.8136652 | Ret | -3.961364 | Tgfb1i1 | -4.12322 | Kirrel | -4.230369 |
| Gprc5c | -3.81437 | Pcnt | -3.9678864 | Cacna1g | -4.123272 | Ptprb | -4.231066 |
| Myo18a | -3.8196607 | Zfp526 | -3.969983 | Itgal | -4.1238036 | Grlf1 | -4.2311497 |
| Elmsan1 | -3.819913 | Gm4980 | -3.9711947 | Gm19361 | -4.125236 | Nrxn1 | -4.233197 |
| Xpo4 | -3.8226562 | Flnb | -3.9750788 | Gm2115 | -4.1273193 | C030034L19Rik | -4.2333245 |
| Eif4ebp2 | -3.8249176 | Tgfb2 | -3.975276 | Midn | -4.127541 | Sptan1 | -4.2337613 |
| Hivep1 | -3.8300369 | Tshz1 | -3.9792788 | C77080 | -4.1280594 | Tmed8 | -4.233967 |
| Slc18a3 | -3.831088 | Elf4 | -3.9806077 | Ly9 | -4.129388 | Anks1 | -4.2406545 |
| Cdk5r1 | -3.831088 | Slc16a2 | -3.9816978 | Gprc5b | -4.2453117 | Fto | -4.2233413 |
| Rcor2 | -3.8320394 | Rarg | -3.981728 | Bcr | -4.2455306 | Dag1 | -4.4236593 |
| Creb3l2 | -3.8323138 | Tacc1 | -3.9827433 | Dmwd | -4.250221 | Adhfe1 | -4.4241734 |
| Zfp629 | -3.8323925 | D630003M21Rik | -3.9873774 | Cacna1b | -4.2541018 | Fhod3 | -4.4241734 |
| Ano8 | -3.8353221 | Jak3 | -3.9919577 | Chrm2 | -4.255423 | Grik5 | -4.4261847 |
| Ctnnd2 | -3.844075 | Ptprm | -3.99713 | Col6a2 | -4.2586346 | A630081J09Rik | -4.427341 |

TABLE 6-continued

2'-FL Signature Response

| Genes | Fold Change (Pre- to Post-op) | Genes | Fold Change (Pre- to Post-op) | Genes | Fold Change (Pre- to Post-op) | Genes | Fold Change (Pre- to Post-op) |
|---|---|---|---|---|---|---|---|
| Acacb | −4.267258 | Cit | −4.429508 | Slit2 | −4.688915 | D430019H16Rik | −4.8766685 |
| Lrrc47 | −4.268472 | Pknox2 | −4.430082 | Slc35f1 | −4.695442 | Amer1 | −4.883436 |
| Sparcl1 | −4.2843194 | Chst15 | −4.432434 | 2900026A02Rik | −4.69737 | Disp2 | −4.88868 |
| Per1 | −4.284555 | Pcsk6 | −4.4335117 | Robo4 | −4.701385 | Kri1 | −4.8890862 |
| Nedd4 | −4.292223 | Pitpnc1 | −4.4337797 | Camk2a | −4.7199683 | Elavl3 | −4.9023004 |
| Patl1 | −4.294661 | Dvl3 | −4.4450216 | Foxm1 | −4.731404 | Scg3 | −4.9046216 |
| Sall2 | −4.297699 | Cadm3 | −4.449833 | Esyt1 | −4.7482824 | Gm4951 | −4.905149 |
| Scd4 | −4.2982802 | Rgs7bp | −4.454611 | Olfml2a | −4.749002 | L3mbtl3 | −4.906046 |
| Fat4 | −4.2990828 | Epas1 | −4.456918 | Glt1d1 | −4.749003 | Myh14 | −4.9095874 |
| Acvr1b | −4.3128395 | Kdr | −4.467747 | Med13l | −4.7498035 | Steap4 | −4.9147515 |
| Socs7 | −4.3131185 | Ankrd63 | −4.471507 | Ski | −4.9168715 | Cdh5 | −5.1172233 |
| Ppp1r12b | −4.323171 | Podxl | −4.472682 | Klf9 | −4.9183517 | Dtx1 | −5.1172767 |
| Brwd3 | −4.3255105 | Rrp1b | −4.4761367 | Ppp1r26 | −4.9196367 | Negr1 | −5.1174483 |
| Clip1 | −4.327361 | Mamld1 | −4.4766836 | Cd4 | −4.924234 | Ubr4 | −5.1175075 |
| Tmem131 | −4.3279204 | AI661453 | −4.47738 | Zfp532 | −4.9277363 | Trf | −5.1282306 |
| Limch1 | −4.3300138 | Zfp703 | −4.4867244 | Pde7b | −4.930655 | Tcof1 | −5.1314826 |
| Piezo1 | −4.3302298 | Lrp5 | −4.491227 | Lama5 | −4.9314804 | Arid1a | −5.1333942 |
| Epb4.1l3 | −4.3332763 | Nptxr | −4.5004888 | Sfxn5 | −4.939162 | Pcdh20 | −5.133799 |
| Card11 | −4.334349 | Gpr56 | −4.503473 | Atxn1 | −4.9407554 | Btbd11 | −5.1357737 |
| Pcsk5 | −4.3404045 | Ap3b2 | −4.5146284 | Hip1 | −4.943426 | Adamtsl3 | −5.143559 |
| Vps13d | −4.3435187 | Frmd4a | −4.516533 | Zfp516 | −4.9528127 | Mep1a | −5.1705327 |
| Itgax | −4.3593884 | Megf8 | −4.516678 | Bdkrb2 | −4.961331 | Pag1 | −5.174592 |
| Foxp2 | −4.375012 | Sox18 | −4.517504 | Arhgef17 | −4.970473 | Ntsr1 | −5.174861 |
| Zfp369 | −4.375357 | Trip11 | −4.535579 | Zmiz2 | −4.9708333 | Tmem163 | −5.176623 |
| Pcdhgc3 | −4.3756924 | Uaca | −4.542734 | Ptpn14 | −4.9750147 | Camta2 | −5.1961904 |
| Zfp142 | −4.377688 | Galnt15 | −4.552306 | Zbtb38 | −4.9796386 | Sez6l2 | −5.2013564 |
| Pappa | −4.3778944 | Setd1a | −4.5583797 | Nav1 | −4.981116 | Nos3 | −5.218715 |
| Abcc9 | −4.379655 | Tnfrsf26 | −4.5600734 | Col4a1 | −4.9823756 | Slfn10-ps | −5.223731 |
| Pogk | −4.380037 | Syde1 | −4.562801 | Dock2 | −4.982716 | Ltbp3 | −5.228651 |
| Ptprn2 | −4.390874 | Trpm2 | −4.5635514 | Wiz | −4.998267 | Ace | −5.2463965 |
| Trio | −4.393027 | Grip2 | −4.564409 | Sv2a | −5.0053463 | Ago2 | −5.2492127 |
| Porcn | −4.3976808 | Zcchc3 | −4.5677176 | Fnbp1 | −5.008047 | Thada | −5.2677145 |
| Radil | −4.408583 | Pcdh1 | −4.5682573 | Kcnb1 | −5.010388 | Laptm5 | −5.2779336 |
| Plch2 | −4.409762 | LOC101055680 | −4.5691104 | Jup | −5.0150137 | Fkbp5 | −5.2862225 |
| Csf2rb2 | −4.4100227 | Cdk5rap2 | −4.569881 | Crtc3 | −5.0191708 | Ust | −5.2888474 |
| Mapk4 | −4.4114933 | Vwa5b2 | −4.585038 | Palld | −5.0217223 | Gli2 | −5.3054004 |
| 2310067B10Rik | −4.4123216 | Rcc2 | −4.586135 | Tead1 | −5.050662 | Shisa7 | −5.3106127 |
| Cdon | −4.4179325 | Gm1966 | −4.5880904 | Gm2366 | −5.055023 | Pvrl1 | −5.3143053 |
| Calcoco1 | −4.4182973 | Ncapd2 | −4.589574 | Zbtb16 | −5.0555153 | Cdc42ep1 | −5.31651 |
| Cdh2 | −4.59065 | Nell2 | −4.7506185 | Gm11201 | −5.0556564 | Fbxo21 | −5.321967 |
| Hoxc6 | −4.5949407 | Clmn | −4.751724 | Adam19 | −5.059814 | Col1a1 | −5.342879 |
| LOC101056227 | −4.5958233 | Siglec1 | −4.7526827 | Gpr116 | −5.0676403 | Kmt2a | −5.3545256 |
| Hoxa5 | −4.596142 | Maml3 | −4.760116 | Tacr1 | −5.076394 | Zfp366 | −5.3598323 |
| Nuak1 | −4.5972643 | Hpn | −4.76763 | Khsrp | −5.0784163 | Bahcc1 | −5.363503 |
| Ash1l | −4.5976686 | Itgb4 | −4.7685833 | R3hdm2 | −5.0837603 | Tfcp2l1 | −5.3767548 |
| Pnliprp2 | −4.6042123 | Tln2 | −4.7695293 | Mira | −5.0844316 | C6 | −5.3849826 |
| Zcchc2 | −4.607047 | Grasp | −4.7808456 | Ebf3 | −5.0845904 | Col23a1 | −5.3898787 |
| Ggn | −4.6074705 | Lrp3 | −4.7833815 | Colq | −5.0845904 | Foxo6 | −5.39518 |
| Pde4a | −4.6094265 | 4833424O15Rik | −4.7847824 | Slc6a6 | −5.088749 | Garem | −5.4109907 |
| Phactr4 | −4.61111 | Dusp2 | −4.787413 | Sema4d | −5.097991 | Cacna1c | −5.4129567 |
| Xylt1 | −4.613241 | Pglyrp2 | −4.793648 | Kcnd3 | −5.1022906 | D8Ertd82e | −5.422087 |
| Chd6 | −4.614547 | Cpm | −4.7953043 | 6330408A02Rik | −5.106721 | Tmem104 | −5.4254866 |
| Mnt | −4.6214833 | Cep250 | −4.807102 | Phf2 | −5.109892 | Nfatc2 | −5.432931 |
| Tnrc6c | −4.6343555 | Tet3 | −4.819702 | Cmklr1 | −5.1149483 | Nell1 | −5.4362507 |
| Zfp462 | −4.644206 | 6530402F18Rik | −4.8258195 | Cplx1 | −5.1157084 | Nrp2 | −5.453444 |
| Chst11 | −4.644287 | Acaca | −4.828735 | Gm11747 | −5.457425 | Sipa1 | −5.7499647 |
| Cdk5r2 | −4.6447372 | Amotl1 | −4.8289275 | Atf7ip | −5.4581237 | Ankrd35 | −5.7507935 |
| Kif13a | −4.6449 | Zfp319 | −4.83489 | Ssh1 | −5.471464 | Rere | −5.7533846 |
| Tnfrsf22 | −4.647929 | Atp2b4 | −4.839279 | Col13a1 | −5.478471 | Mbd6 | −5.762398 |
| Tshz2 | −4.651497 | Klf13 | −4.8399653 | Creb3l1 | −5.493979 | Shroom4 | −5.773704 |
| Gpr81 | −4.653481 | Irgq | −4.846592 | Snph | −5.4958516 | Igdcc4 | −5.775498 |
| Bcorl1 | −4.654811 | Bicd1 | −4.847597 | Scn9a | −5.495918 | Fgd1 | −5.7782965 |
| Mical2 | −4.65618 | Pecam1 | −4.847935 | Rftn1 | −5.5102477 | D10Bwg1379e | −5.781159 |
| Sipa1l1 | −4.659589 | Gaa | −4.848122 | Vwf | −5.510766 | Cul7 | −5.7837934 |
| Mllt6 | −4.660232 | Samd4b | −4.8494883 | Plekhg2 | −5.529776 | Unc45b | −5.7871437 |
| Pom121 | −4.660895 | Cdc42bpb | −4.850499 | 4930470H14Rik | −5.5310645 | Lrrc32 | −5.7874193 |
| N4bp2 | −4.664106 | Gpr20 | −4.8509173 | Trim44 | −5.531987 | Nat8l | −5.812604 |
| Mypop | −4.6661606 | Adcy9 | −4.853269 | Cep170b | −5.543748 | Pcnxl3 | −5.827555 |
| Slc38a1 | −4.667554 | Tspan18 | −4.8583994 | Dlc1 | −5.5460204 | Rnf169 | −5.831864 |
| Ank2 | −4.668032 | Arhgef11 | −4.866661 | H1fx | −5.5563064 | Akna | −5.832198 |
| Golga3 | −4.6702375 | Gm7694 | −4.867113 | Abca3 | −5.574395 | Myh11 | −5.837445 |
| Amotl2 | −4.6704555 | Zfp362 | −4.867447 | Myh9 | −5.5906363 | Alppl2 | −5.837605 |
| Npc1 | −4.681958 | Zfp574 | −4.8711977 | Timp4 | −5.5927744 | Lphn1 | −5.838535 |
| Ctif | −4.6889114 | Aebp1 | −4.871624 | Rcor1 | −5.595832 | Ahdc1 | −5.84686 |

TABLE 6-continued

2'-FL Signature Response

| Genes | Fold Change (Pre- to Post-op) | Genes | Fold Change (Pre- to Post-op) |
|---|---|---|---|
| Tln1 | −5.596702 | Il12rb2 | −5.8473353 |
| Sh3pxd2a | −5.597526 | Igfbp5 | −5.8487153 |
| Mgat5 | −5.622285 | Lmln | −5.848787 |
| Akap2 | −5.630095 | Xpnpep2 | −5.8541245 |
| Stxbp1 | −5.639406 | Slc9a1 | −5.8618016 |
| Gap43 | −5.6414924 | Ift122 | −5.8630185 |
| Syne1 | −5.6437426 | Sik2 | −5.8707633 |
| Filip1 | −5.6474614 | Chd3 | −5.8761563 |
| Gpam | −5.656237 | Scube1 | −5.889338 |
| Zc3h3 | −5.6595454 | Zbtb39 | −5.896369 |
| Arhgef10 | −5.6626935 | Jade2 | −5.9055915 |
| Kmt2d | −5.6735272 | Adcyap1r1 | −5.913129 |
| Calb2 | −5.6839123 | Mn1 | −5.9321766 |
| Mpp2 | −5.693481 | Cd93 | −5.940118 |
| Helz | −5.695566 | Chrnb4 | −5.9437118 |
| Ksr1 | −5.7027316 | 9330159F19Rik | −5.9446855 |
| Angel1 | −5.7037864 | D930015E06Rik | −5.9454174 |
| Arhgap20 | −5.714819 | Chst8 | −5.9597144 |
| Pear1 | −5.72119 | Msi1 | −5.9620185 |
| Wasf2 | −5.7250338 | Rusc2 | −5.979772 |
| Card10 | −5.7258663 | Mpdz | −6.001348 |
| Plxnd1 | −5.727163 | Tns3 | −6.014395 |
| Ano7 | −5.7371073 | Brd4 | −6.02844 |
| Sh3bp1 | −5.738779 | Inpp5d | −6.0621934 |
| Malat1 | −5.7421117 | Srgap3 | −6.0965333 |
| Kcnj10 | −5.742256 | Zfp423 | −6.1029797 |
| Nfic | −6.1067474 | Jag2 | −6.52813 |
| Mtss1l | −6.109766 | Cdc42bpa | −6.528735 |
| Aoc3 | −6.1320453 | Mfhas1 | −6.535573 |
| Kcna6 | −6.135476 | Gpr132 | −6.5452857 |
| Prrc2b | −6.1435466 | Rin3 | −6.5626183 |
| Cmip | −6.159686 | Dbh | −6.5871367 |
| Fam65a | −6.1830106 | Dnmbp | −6.599508 |
| Lpl | −6.2096405 | Zfp316 | −6.6049 |
| Gse1 | −6.2440376 | Klhdc7a | −6.608837 |
| Sntb1 | −6.247363 | Ppp1r3e | −6.6151266 |
| Daam2 | −6.2539988 | Slc29a3 | −6.656874 |
| Col9a2 | −6.2607245 | Med12 | −6.660314 |
| Ttyh3 | −6.2627654 | Kcna1 | −6.6635137 |
| Atp11a | −6.2652125 | Adipoq | −6.6703973 |
| Prox1 | −6.279515 | Pdgfrb | −6.671171 |
| Sipa1l3 | −6.2824764 | Trpm6 | −6.6845455 |
| Auts2 | −6.2862473 | Csf1r | −6.702886 |
| Hoxb5 | −6.299032 | Tmem130 | −6.7176085 |
| Ankrd11 | −6.321779 | Gli3 | −6.732471 |
| Dhx9 | −6.336916 | 5031414D18Rik | −6.733136 |
| Azi1 | −6.3425527 | Slc8a2 | −6.7361636 |
| Stox2 | −6.3468223 | Foxk1 | −6.746511 |
| 4922501C03Rik | −6.3521485 | Adamtsl4 | −6.748529 |
| Wdr19 | −6.3581853 | Hk1 | −6.772794 |
| Kcnc3 | −6.358278 | Zbtb12 | −6.7807746 |
| Aox1 | −6.358278 | Sh2b2 | −6.790647 |
| Foxp4 | −6.370567 | Zmiz1 | −6.799131 |
| Tnrc6b | −6.379 | Slc41a1 | −6.8051305 |
| Magee1 | −6.3891907 | Cyp2e1 | −6.806272 |
| Abl2 | −6.4011426 | Apbb1ip | −6.816424 |
| Adam23 | −6.410632 | Ptprn | −6.8339634 |
| Dpysl3 | −6.418519 | Tns1 | −6.857737 |
| Ncdn | −6.445858 | Whrn | −6.861942 |
| Gbp5 | −6.4491224 | Nrip1 | −6.8683486 |
| Mark4 | −6.4511843 | Snap91 | −6.8734684 |
| Hdac4 | −6.4641075 | Hyal1 | −6.874232 |
| Glg1 | −6.4643683 | Plcb4 | −6.8800087 |
| Tenc1 | −6.478705 | Plec | −6.8957624 |
| Ablim2 | −6.480041 | Kif21b | −6.9017057 |
| Fasn | −6.4808755 | Thsd4 | −6.920586 |
| Ncor2 | −6.48242 | Tmem8b | −6.931616 |
| Gpr65 | −6.495445 | Hr | −6.9388337 |
| Fam214a | −6.502225 | Pde11a | −6.9536076 |
| 5330417C22Rik | −6.512623 | Tmod2 | −6.959487 |
| Prrg3 | −6.5163846 | Gm8995 | −6.993875 |
| Tmem59l | −6.998191 | Pianp | −7.762673 |
| Tusc5 | −7.013599 | Kif13b | −7.7728205 |
| Il27ra | −7.022937 | Rgma | −7.77704 |
| Notch3 | −7.0860233 | 1500004A13Rik | −7.7786875 |
| Prrc2a | −7.106074 | Sf3a2 | −7.791673 |
| Itpkb | −7.1062007 | Crebbp | −7.8226275 |
| Ltbp4 | −7.1191564 | Gdnf | −7.824902 |
| Anks6 | −7.1227174 | Il7r | −7.866939 |
| Bmpr2 | −7.125927 | Itga2 | −7.8919287 |
| Cpeb4 | −7.155012 | Glb1l2 | −7.8930554 |
| Cic | −7.1640706 | Kdm6b | −7.911397 |
| Chd5 | −7.198922 | Gm4759 | −7.9212666 |
| Abcd2 | −7.22994 | Tubb4a | −7.9681025 |
| Col4a2 | −7.238271 | Ache | −7.9681053 |
| Plxna4 | −7.2494235 | Prelp | −7.9925165 |
| Ston1 | −7.252846 | Akap13 | −8.026527 |
| Armcx4 | −7.2888837 | Dpp6 | −8.042486 |
| Snx30 | −7.295525 | Spock2 | −8.059016 |
| Erbb3 | −7.300009 | Ubap2 | −8.098392 |
| Celsr2 | −7.304149 | Nhsl2 | −8.107769 |
| Adcy1 | −7.3139043 | Hcn2 | −8.180631 |
| Atp1a3 | −7.338341 | Cgnl1 | −8.2398 |
| Cbl | −7.3394046 | Kif26a | −8.286204 |
| L1cam | −7.3658 | Iqsec1 | −8.356945 |
| B230344G16Rik | −7.415622 | Cachd1 | −8.437805 |
| Dchs1 | −7.4220014 | Arhgap23 | −8.446765 |
| P2rx2 | −7.4226885 | Sufu | −8.462171 |
| Phc1 | −7.423785 | Fgfr1 | −8.590408 |
| Arhgef15 | −7.457891 | Akap12 | −8.621501 |
| Satb2 | −7.470253 | Pik3ap1 | −8.642886 |
| Man1c1 | −7.4863563 | Bcl9 | −8.6600275 |
| Elavl4 | −7.4957004 | Coro2b | −8.66336 |
| Grik3 | −7.5566597 | Slc29a4 | −8.7953615 |
| Slc2a3 | −7.5652304 | Atf7 | −8.820167 |
| Wnk2 | −7.59136 | Srgap1 | −8.900707 |
| Foxq1 | −7.5950203 | C1qtnf1 | −8.932076 |
| Obsl1 | −7.6073546 | Il17rd | −8.946743 |
| Zfp395 | −7.634175 | Fmnl1 | −8.990396 |
| Tmem231 | −7.662053 | Cacna2d2 | −9.019706 |
| Zdhhc23 | −7.6683893 | Smad9 | −9.062572 |
| Cyfip2 | −7.6827292 | Rdh1 | −9.097828 |
| Gnao1 | −7.71014 | Kcnk3 | −9.119993 |
| Tnrc18 | −7.7115493 | Vps13c | −9.13157 |
| Slc7a8 | −7.745732 | Unc5a | −9.201129 |
| Mmrn2 | −7.7559443 | Fras1 | −9.209607 |
| Scd3 | −9.215791 | Setd1b | −12.66494 |
| Lect2 | −9.259112 | Shank2 | −12.675208 |
| Lpin1 | −9.312303 | Flt4 | −12.718141 |
| Fan1 | −9.33016 | Pacs1 | −12.765819 |
| Sptb | −9.371043 | Slc36a2 | −12.88352 |
| Pnpla3 | −9.606205 | Zbtb34 | −13.147643 |
| AI414108 | −9.671371 | Gltscr1 | −13.3046255 |
| Parvb | −9.684021 | Soga1 | −14.403646 |
| Trim56 | −9.711379 | Spen | −14.444155 |
| Zbed6 | −9.794251 | Tenm3 | −14.717207 |
| Agap2 | −9.80083 | Shank3 | −15.223462 |
| Rgs9 | −9.820603 | Tiam1 | −15.276154 |
| Car3 | −9.900808 | Peg3 | −15.365936 |
| Leprel1 | −9.902655 | D830031N03Rik | −15.567059 |
| Trerf1 | −9.926495 | Flt1 | −15.792703 |
| Lyst | −9.937674 | Plin1 | −16.340084 |
| Ptpru | −10.006784 | Nfix | −16.561 |
| Tmem151a | −10.064172 | Sema3g | −18.019087 |
| Bcl9l | −10.077599 | Polr2a | −18.451906 |
| Ldoc1l | −10.252967 | Atp1a2 | −18.469486 |
| Nos1ap | −10.381967 | Atp1b2 | −18.713383 |
| Ebf1 | −10.391403 | Apba1 | −18.876522 |
| Ankrd52 | −10.579999 | Scd1 | −20.279074 |
| Fscn1 | −10.734042 | Rnf150 | −20.412802 |
| Zfp609 | −11.218482 | P2ry4 | −22.221027 |
| Chd7 | −11.263155 | Ttc28 | −24.21734 |
| Nav2 | −12.390556 | Irs2 | −43.59841 |
| Tomm6os | −12.407566 | Fgf15 | −64.61133 |

2'-FL Signature Response

Those genes differentially regulated following ICR in animals supplemented with 2'-FL, less the adaptive response observed in the control group, included 2,030 entities. Among the upregulated entities (n=783) (Tables 5-6), ontologies pertaining to energy presence and processing were most salient, including electron transport chain (p=1.87E-35), cellular respiration (p=4.53E-30), mitochondrial ATP synthesis coupled electron transport (p=2.67E-20), generation of precursors metabolites and energy (p=3.01E-20), energy derivation by oxidation of organic compounds (p=4.26E-20), and organic cyclic compound catabolic process (p=1.10E-08). Also discovered were ontologies suggesting host-microbial interaction, including multi-organism metabolic process (p=1.59E-22), symbiosis, encompassing mutualism through parasitism (p=1.47E-13), interspecies interaction between organisms (p=1.47E-13), multi-organism cellular process (p=8.20E-13), and mucosal immune response (p=1.40E-06). Finally, ontologies involving biosynthetic processes were discovered, including sterol biosynthetic process (p=6.22E-08), cholesterol biosynthetic process (p=1.76E-07), and various nucleoside biosynthetic processes. Of the upregulated entities, the most strongly upregulated genes of the 2'-FL signature response were: Tmem202 (FC=18.0), Map3k12 (FC=16.2), Hemt1 (FC=15.4), Mcpt2 (FC=13.4), and Fmr1nb (FC=12.7).

Among the downregulated entities of the 2'-FL signature response (n=1,247), similar ontologies to those downregulated in the adaptive response were strongly present. These included neurogenesis (p=7.34E-20), regulation of developmental process (p=5.83E-18), cardiovascular system development (p=2.91E-17), circulatory system development (p=2.91E-17), and axonogenesis (p=7.60E-16). Further, regulation of development at a cellular lever was observed, with ontologies including cell development (p=2.76E-20), cell morphogenesis involved in differentiation (p=1.96E-18), epithelial development (p=2.78E-13), epithelial tube morphogenesis (p=7.39E-13), cell junction assembly (p=2.60E-09), and cellular response to growth factor stimulus (p=4.30E-09). Finally, ontologies relevant to control over cell cycle were discovered, including regulation of Ras protein signal transduction (p=1.50E-11) and positive regulation of Ras GTPase activity (p=1.69E-10). Related to this theme were ontologies including positive regulation of cellular biosynthetic process (p=1.34E-11) and regulation of nucleotide metabolic process (p=3.41E-11). Of the downregulated entities, the most strongly downregulated genes of the 2'-FL signature response were: Fgf15 (FC=−64.6), Irs2 (FC=−43.6), Ttc28 (FC=−24.2), P2ry4 (FC=−22.2), and Rnf150 (FC=−20.4).

To determine all non-redundant, functionally grouped gene ontology and pathway annotation networks based on the gene set of the upregulated 2'-FL signature response, Cytoscape's ClueGO application was used (FIG. 33, Panel C). The ClueGO networks discovered underscored the importance of energy processing with ontologies and pathways related to the electron transport chain, oxidative phosphorylation, and protein targeting to the mitochondrion. Further, sterol biosynthesis was discovered. As expected, ontologies involved in the mucosal immune response were also upregulated. When ClueGO was used to generate networks based on the downregulated 2'-FL signature response, ontologies and pathways relating to the IL-7 signaling pathway, positive regulation of Rho GTPase activity, and cell adhesion were discovered (data not shown).

Discussion

2'-Fucosyllactose, the dominant human milk oligosaccharide produced by women who are FUT2 secretors, augments the sustained adaptive response to extensive intestinal resection in mice. Here, it was surprisingly discovered that operated animals supplemented with 2'-FL gained more weight than control animals, a robust marker of intestinal function. Further, a prolonged but characteristic morphometric adaptive response among supplemented animals was observed though differences were found only after the point of weight divergence, indicating additional sources of improved growth. 2'-FL buffered microbial changes previously observed after resection, which may have been the stimulus for transcriptional activity most heavily supporting increased energy utilization among supplemented and resected animals. It was discovered that supplementation with 2'-FL, an indigestible and non-caloric prebiotic, increases weight gain following ileocecal resection by increasing energy availability through microbial community modulation and directly or indirectly stimulating characteristic histologic changes ultimately resulting in improved adaptation. This difference among secretor animals capable of decorating their intestinal epithelium with the 2'-FL analogue, H-antigen was also observed, highlighting the impact of supplementation.

The impact of 2'-FL on weight gain only occurred after ICR, supporting the findings of augmented adaptation following intestinal resection over an independent effect on weight. This observation has been supported both when comparing control and 2'-FL supplemented healthy human infants who did not demonstrate differential weight gain as well as in mechanistic studies demonstrating improved growth following physiologic stress among secretor mice. Marriage et al. (2015) *J Pediatr Gastroenterol Nutr* 61: 649-658; and Pickard et al. (2014) *Nature* 514: 638-641, 2014. Thus, 2'-FL seemed to buffer against the stress of intestinal loss while exhibiting little to no effect on weight without insult.

Supplementation with 2'-FL augmented the adaptive increase in absorptive surface area through sustained increases characteristic morphometric markers of gut adaptation. Independently, crypt depth was significantly greater among supplemented animals on postoperative day 56. Further, should the trend observed in villus height represent a true difference, even this modest difference would translate to a significant increase in absorptive surface area in 3 dimensions. Control and supplemented animals taken to postoperative day 21, the point of weight divergence between both subgroups, were anticipated to experience a greater difference in these measures. This was not so, suggestive of a separate process responsible for the early weight divergence.

Studies of intestinal loss and associated physiologic stress reveal a marked decline in alpha diversity, which has been associated with poor adaptation as measured by delayed weaning from parenteral nutrition. Engstrand et al. (2015) *Microbiome* 3: 18; and Lapthorne et al. (2013) *Gut Microbes* 4: 212-221. The model of adaptation to massive intestinal loss also induces dysbiosis. Devine et al. (2013) *PloS one* 8: e73140. Solutions for buffering or reversing this dysbiosis may improve adaptation and are highly sought in the treatment of short bowel syndrome. One potential solution is 2'-FL supplementation. Secretor status is a key driver of intestinal microbial community composition, where the ability to secrete H antigen or the availability of the H antigen analogue, 2'-FL, supports increased community diversity and bolsters microbiota during times of stress. Lewis et al. (2015) *Microbiome* 3: 13; Pickard et al. (2014) *Nature* 514: 638-641; Wacklin et al. (2014) *PloS one* 9: e94863; and Yu et al. (2013) *Glycobiology* 23: 169-177. It was discovered that 2'-FL supplementation after intestinal resection resulting in massive intestinal loss results in increased gut microbial diversity occurring with improved adaptation.

In this study, it was also found a bloom in microbes of the genus Parabacteroides (>4 fold increase among supplemented, resected animals compared to controls). Though the body of literature surrounding this genus is scant, their differential presence may impact both a mucosal inflammatory response to resection and the abundance of available energy to the host. These bacteria have not only been found in higher proportions comparing non-inflamed to inflamed enteric samples, but a lysate containing the membranous fraction has been observed to protect from DSS-induced murine colitis. Kverka et al. (2011) *Clinical and experimental immunology* 163: 250-259; Tyler et al. (2013) *PloS one* 8: e66934; and Zitomersky et al. (2013) *PloS one* 8: e63686. A robust and direct interaction between the organism and innate and adaptive immunomodulatory mechanisms occurs, indicating a rational mechanism of interaction of cellular processes involved in the adaptive response. Kverka et al. (2011) *Clinical and experimental immunology* 163: 250-259. Further, this genus readily ferments indigestible carbohydrates, converting them to beneficial and available organic acids, providing a possible explanation for the growth advantage observed among supplemented animals supporting a bloom in this organism. Blatchford et al. (2015) *Benef Microbes* 1-12.

The transcriptional analysis of the late adaptive response is characterized by a release of developmental progression pathways and engagement of ontologies involved in diverse metabolic processes. Transcription of the 2'-FL signature response engages many cellular components responsive to energy presence and processing demands, in support of the presumed increase in energy availability among operated animals supplemented with 2'-FL. Further, ontologies relating to energy derivation by oxidation of organic compounds were discovered—the processes by which short-chain fatty acids are converted to energy after undergoing largely passive intracellular diffusion. Fleming S E et al. (1991) *The Journal of nutrition* 121: 1787-1797. These findings indicate improved energy availability with 2'-FL supplementation among resected animals, likely through short chain fatty acid production. Indeed, a clear increase in short-chain fatty acid and lactate production, sources of mucosal energy, is observed when 2'-FL is added to in vitro infant fecal samples. Yu et al. (2013) *Glycobiology* 23: 169-177.

Owing to the model complexity, animal numbers were limited which restricted power in statistical analysis and modeling. Further, animal fragility during the acute postoperative recovery period prevented animal separation and mixing, resulting in subtle differences in resected microbial community composition and an inability to perform feeding efficiency measures. Finally, C57BL/6 animals are all FUT2 positive, hence all animals studied produce H antigen on gut mucosal surfaces. 2'-FL is an analogue of the H antigen, thus differences observed first overcame the effect of physiologic H antigen presence among all resected animals. It is contemplated that individuals lacking H antigen on gut mucosal surfaces may benefit more greatly from 2'-FL supplementation. It is also contemplated that the effect observed is not specific to 2'-FL but may be seen with other indigestible prebiotic carbohydrates. Notably, carbohydrates historically used as controls, such as inulin, maltodextrin, and galactooligosaccharides exhibit a prebiotic effect or contribute to overall energy balance. Dewulf et al. (2013) *Gut* 62: 1112-1121; Holscher et al. (2015) *The Journal of nutrition* 145: 2025-2032; Nickerson et al. (2014) *PloS one* 9: e101789; Salazar et al. (2015) *Clinical nutrition* 34: 501-507; and Vulevic et al. (2015) *The British journal of nutrition* 1-10. Thus, no control carbohydrate was provided in order to reduce the chance of type 1 or type 2 error.

Enhancing the adaptive response is vitally important to improving health and cost outcomes following extensive intestinal resection. It is shown herein augmentation of adaptation with a naturally occurring prebiotic safe for human consumption. Supplementation with 2' FL provides a shift in gut microbiota to increased Parabacteroides, increased somatic growth, leading to evidence of increased cell growth from IEC transcriptome, and improved histology (villus/crypt development). Further studies in this model evaluating 2'-FL supplementation and withdrawal, the dose-effect relationship, and outcomes among secretor and non-secretor animals can be explored. Additionally, studies of 2'-FL safety and effectiveness after intestinal resection in humans are needed to support a clinical role. Determining the impact of secretor status on human adaptation may identify a substantial subgroup to benefit most from 2'-FL supplementation. Finally, efforts to understand and modulate gut microbial community changes following intestinal resection promise novel treatment paradigms that may help improve the lives of children suffering from short bowel syndrome.

Example 4. Additional Studies of Effects of HMO or FUT2 on Infant Growth

Figure 35:
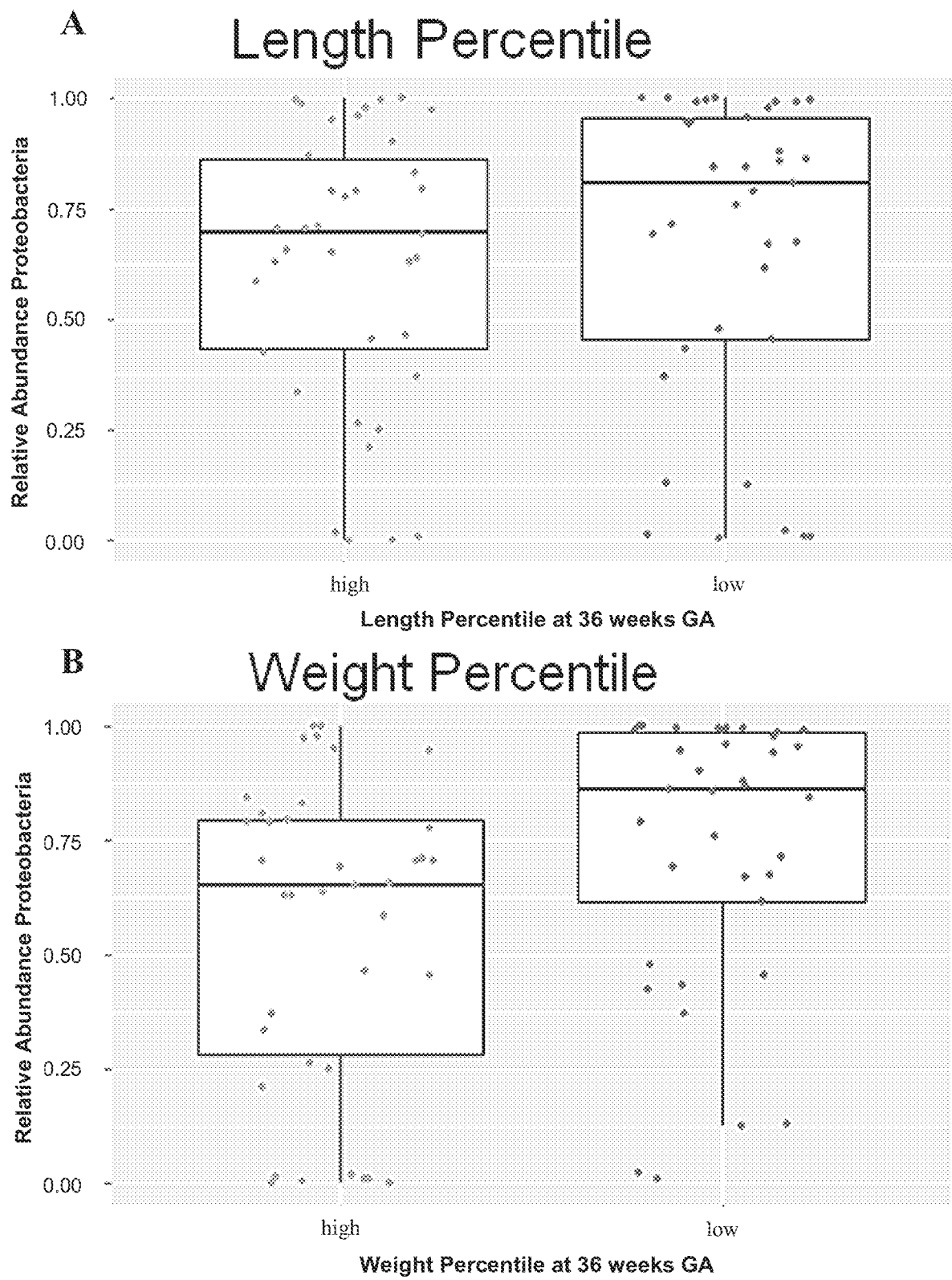
FIG. 35 is a series of graphs showing relationship of relative abundance Proteobacteria with length percentile (Panel A), weight percentile (Panel B), and head circumference percentile (Panel C) of pre-term infants. Taken together, pre-term infants had slower growth with higher Proteobacteria.
Figure 35:
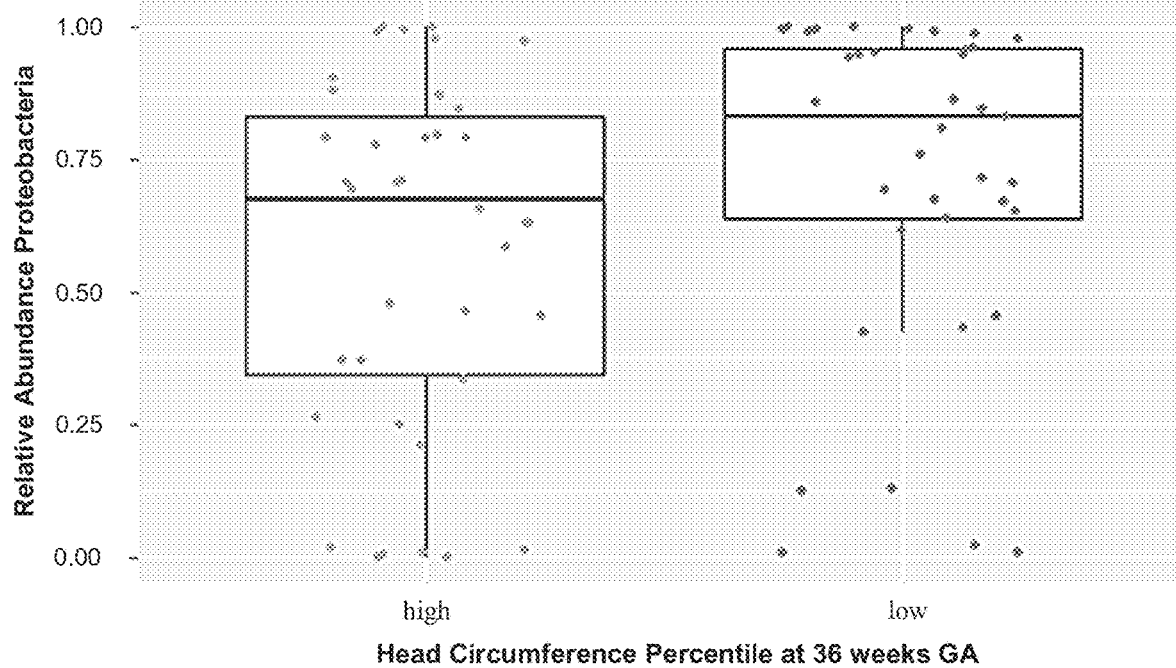

A study of the microbiome of preterm infants<29 weeks GA in relation to their growth at discharge from hospital was conducted. The correlation of relative abundance Proteobacteria to length percentiles (Panel A), weight percentiles (Panel B), and head circumference percentiles (Panel C) of pre-term infants at 36 weeks GA were determined (FIG. 35). Proteobacteria, gram-negative bacteria, generally do not harvest energy from human milk oligosaccharides (HMOS), and can cause inflammation via host TLR4 signaling. As shown in FIG. 35, higher abundance of proteobacteria correlates to slower growth.

Figure 36:
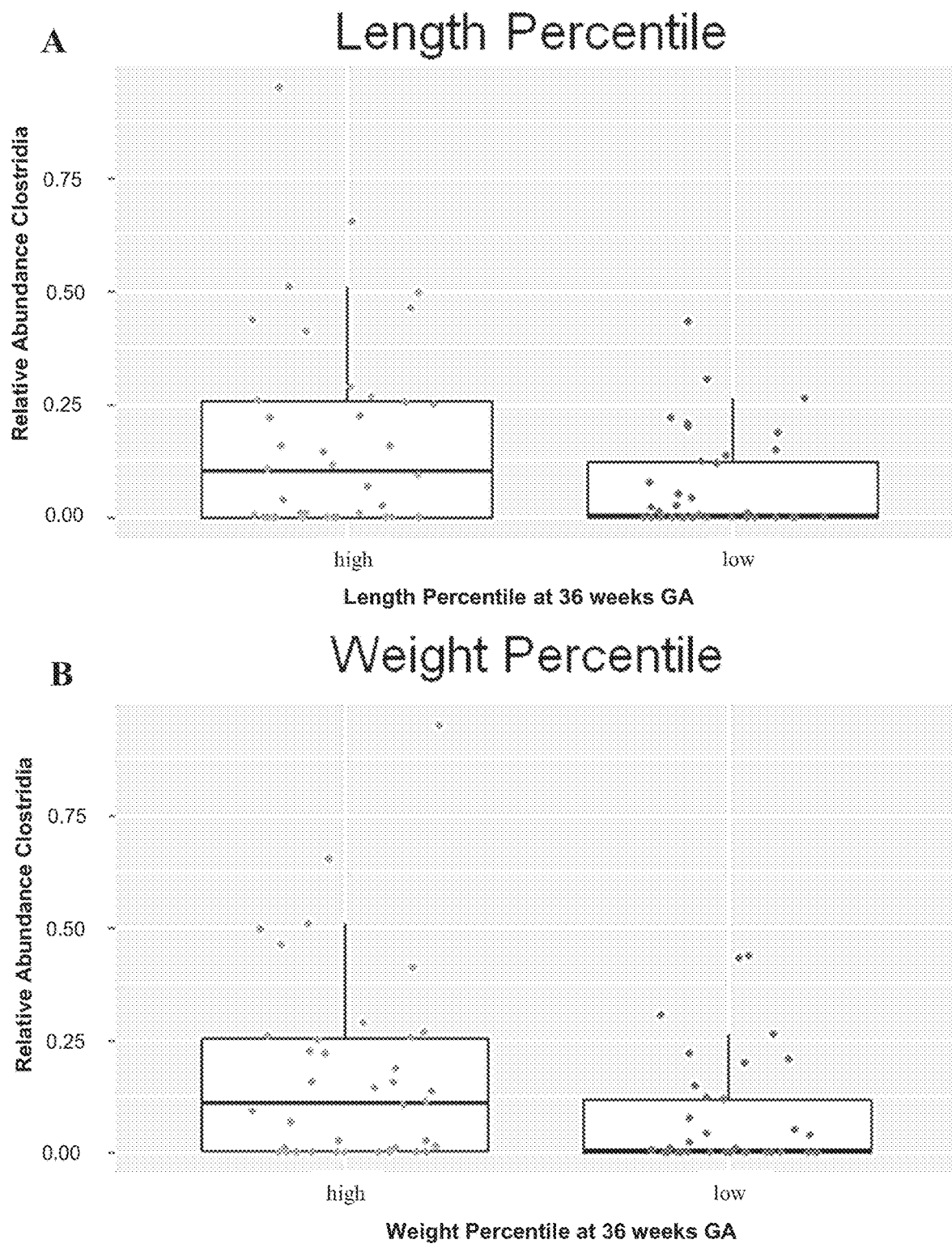
FIG. 36 is a series of graphs showing relationship of relative abundance Clostridia with length percentile (Panel A), weight percentile (Panel B), and head circumference percentile (Panel C) of pre-term infants. Taken together, pre-term infants had greater growth with higher Clostridia.
Figure 36:
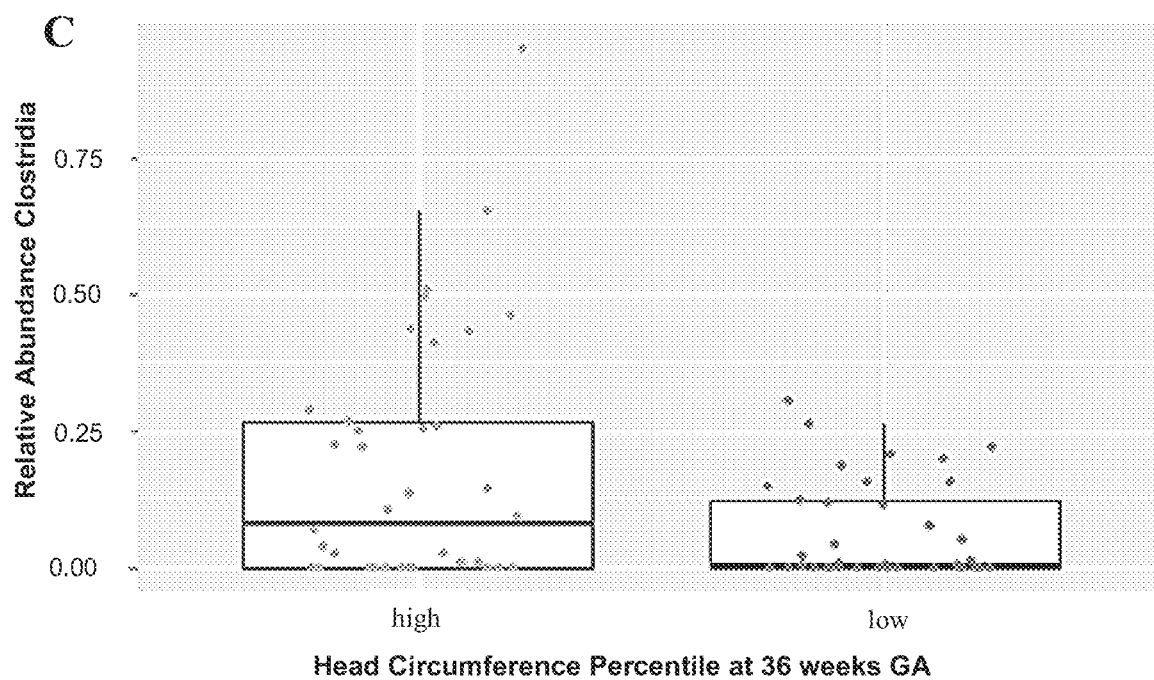

Similarly, the correlation of relative abundance Clostridia to length percentiles (Panel A), weight percentiles (Panel B), and head circumference percentiles (Panel C) of pre-term infants at 36 weeks GA were determined (FIG. 36). Clostridia, gram-positive bacteria, generally utilize HMOS to produce short chain fatty acids (SCFA), and can cause inflammation. As shown in FIG. 36, higher abundance of Clostridia correlates to greater growth.

Figure 37:
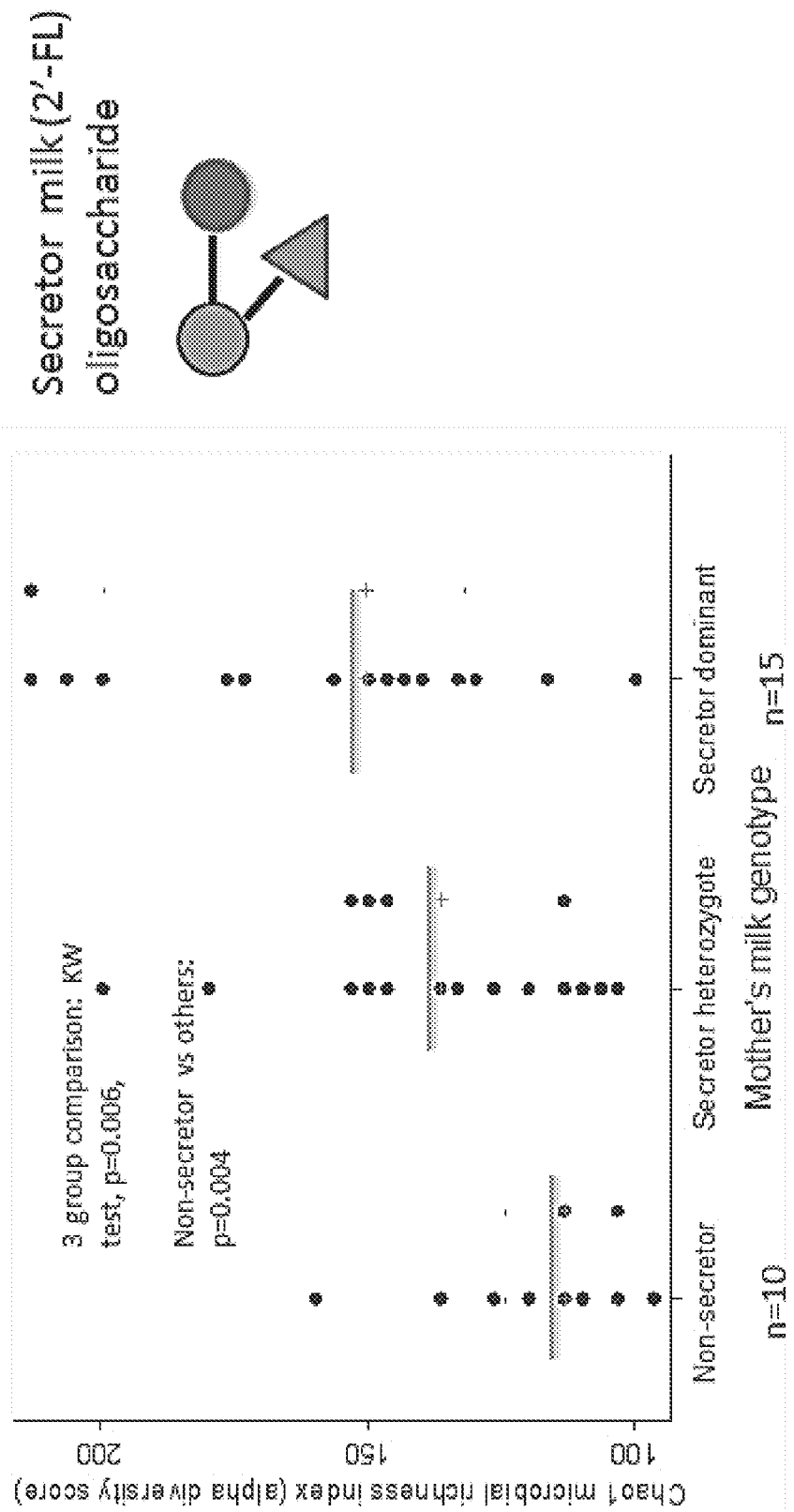
FIG. 37 is a graph showing microbial diversity in breast-fed preterm infants <29 weeks GA by maternal "secretor" milk status.
Figure 39:
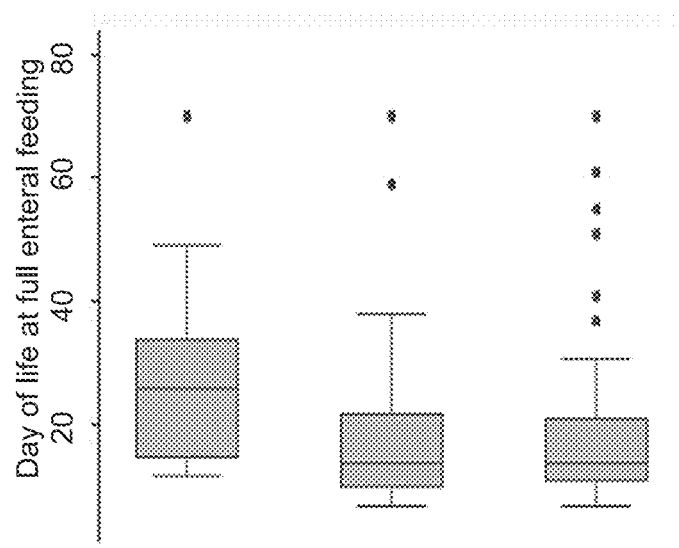
FIG. 39 is a series of graphs showing effects of FUT2 status of preterm breast-fed infants and their mothers on catch-up growth and the length of time to full enteral feeding. The status influences time to full enteral feeding (day of life at full enteral feeding, Y-axis, Panel A) and influences catch-up growth (length and weight Z-scores at 36 weeks corrected GA, Y-axis, Panel B). The X-axis for both panels is the mother-infant FUT2 genotype. Non-secretors-(left) indicated both are non-secretors. Mixed pair (middle) indicates FUT2 discordance. The non-secretor pairs are significantly (p<0.05) disadvantaged in days of life to full enteral feeding (Panel A) and length Z-score (Panel B).
Figure 39:
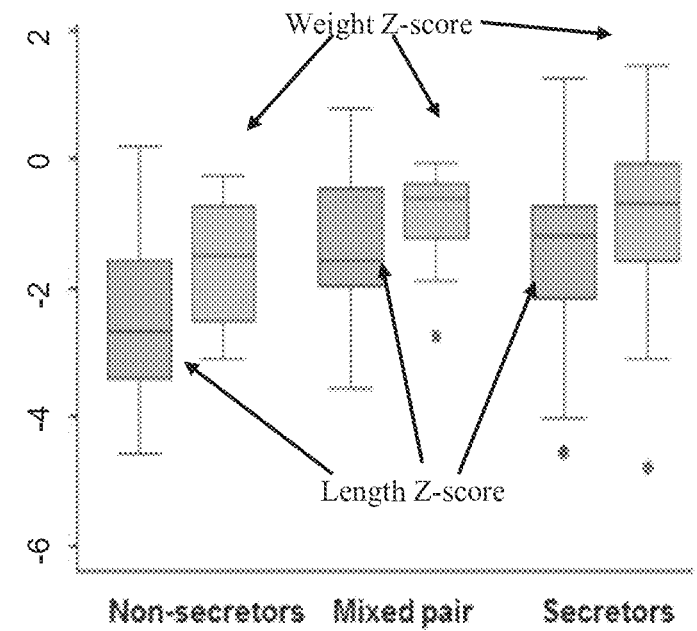

Next, it was sought to determine whether HMOS can help infant growth. To this end, effects of FUT2 on microbial diversity, length of time to full enteral feeding, and growth of pre-term infants were studied. FIG. 37 shows that microbial diversity in breastfed preterm infants <29 weeks GA by maternal "secretor" milk status. To identify expression profile of bacterial gene pathways between FUT2− and FUT2+ subjects, RNA-sequencing was used. FIG. 38 shows that FUT2 oligosaccharide (of mother and infant) associated with greater energy production in infant. FIG. 39 shows that the non-secretor pairs are significantly (p<0.05) disadvantaged in days of life to full enteral feeding (Panel A) and catch-up growth as characterized by length Z-score (Panel B).

Figure 40:
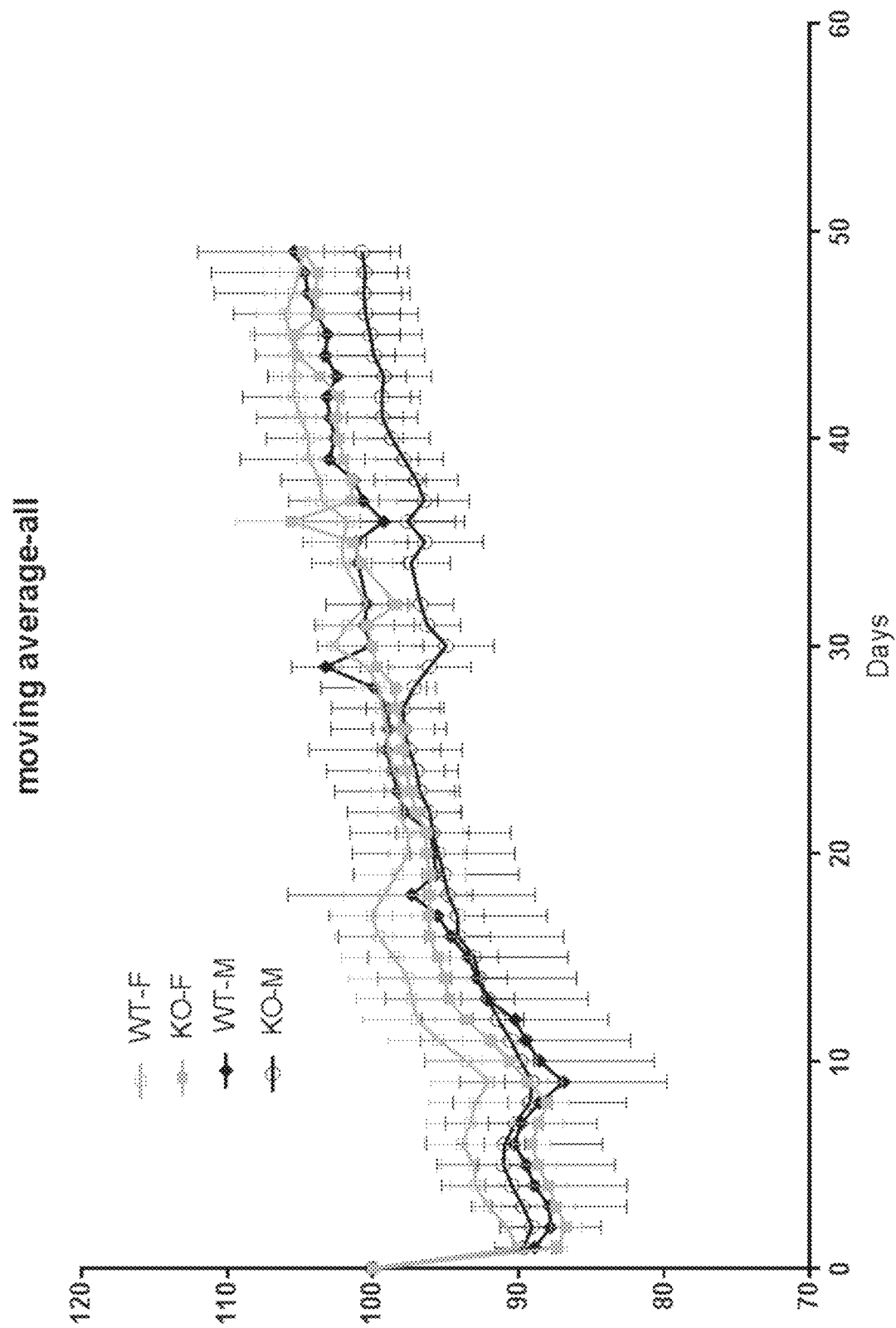
FIG. 40 is a graph showing that WT mice recover weight more quickly than FUT2 knock-outs.

In another study, FUT2 gene was knocked out in mices and then weight of the FUT2 knock-out and wild-type (WT) mice were measured over a period of 50 days. It was determined that WT mice recover weight more quickly than FUT2 knock-outs (FIG. 40).

Figure 41:
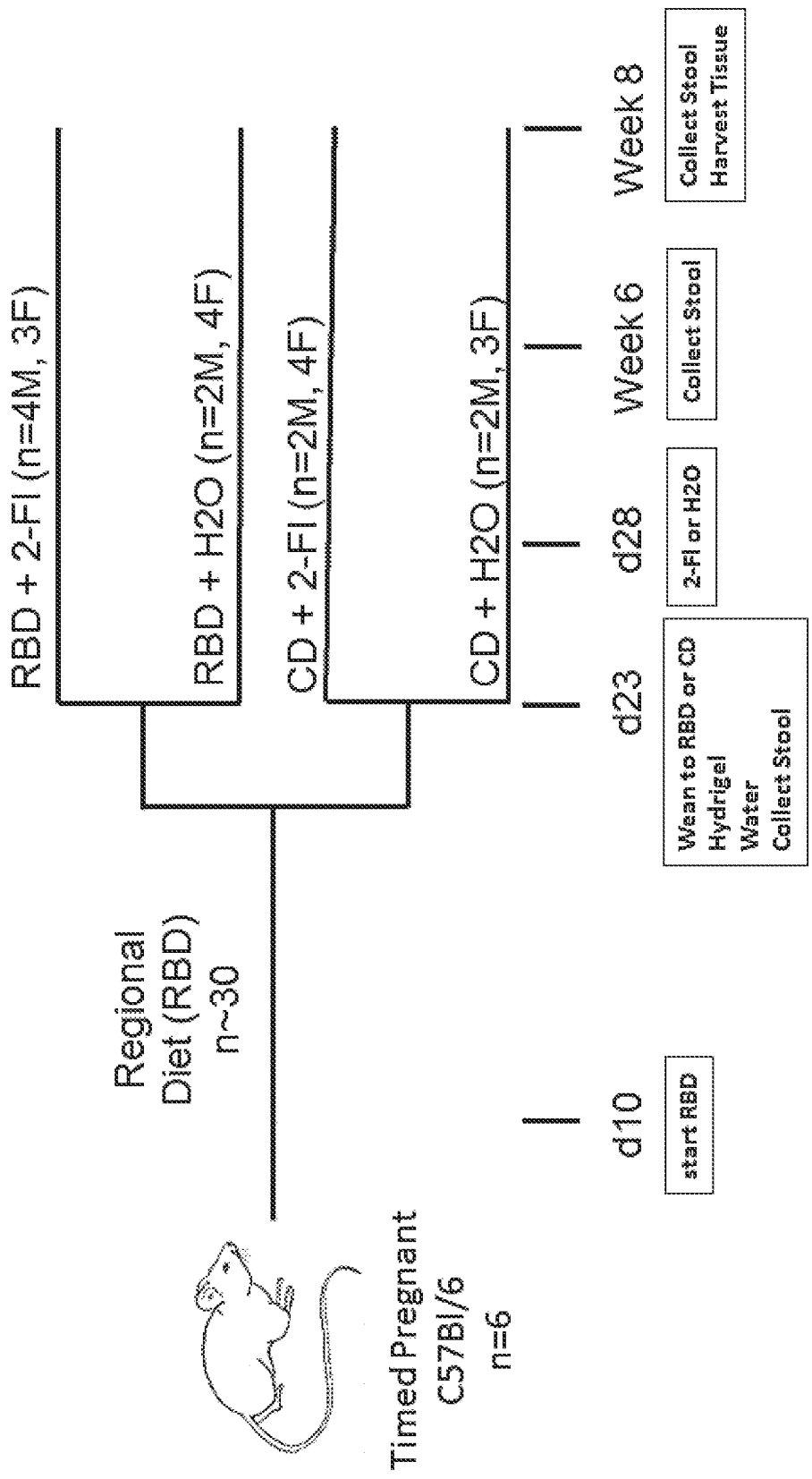
FIG. 41 is a scheme showing a 2'-FL experiment: Environmental Enteropathy. All dams were placed on Regional-based Diet when their pups were 10 days old. At weaning (3 weeks of age), pups were placed on either control diet (CD) or continued on regional-based diet (RBD), which is a malnutrition diet lacking nutrients. At 4 weeks of age, the pups were given either plain drinking water or 2-FL (2.5 g/L) in sipper sacs. Sipper sacs were changed and weighed every other day. Mice and food were weighed twice a week. Stool was collected at weaning, 6 weeks of age, and 8 weeks of age. Mice were sacrificed at 8 weeks of age.
Figure 42:
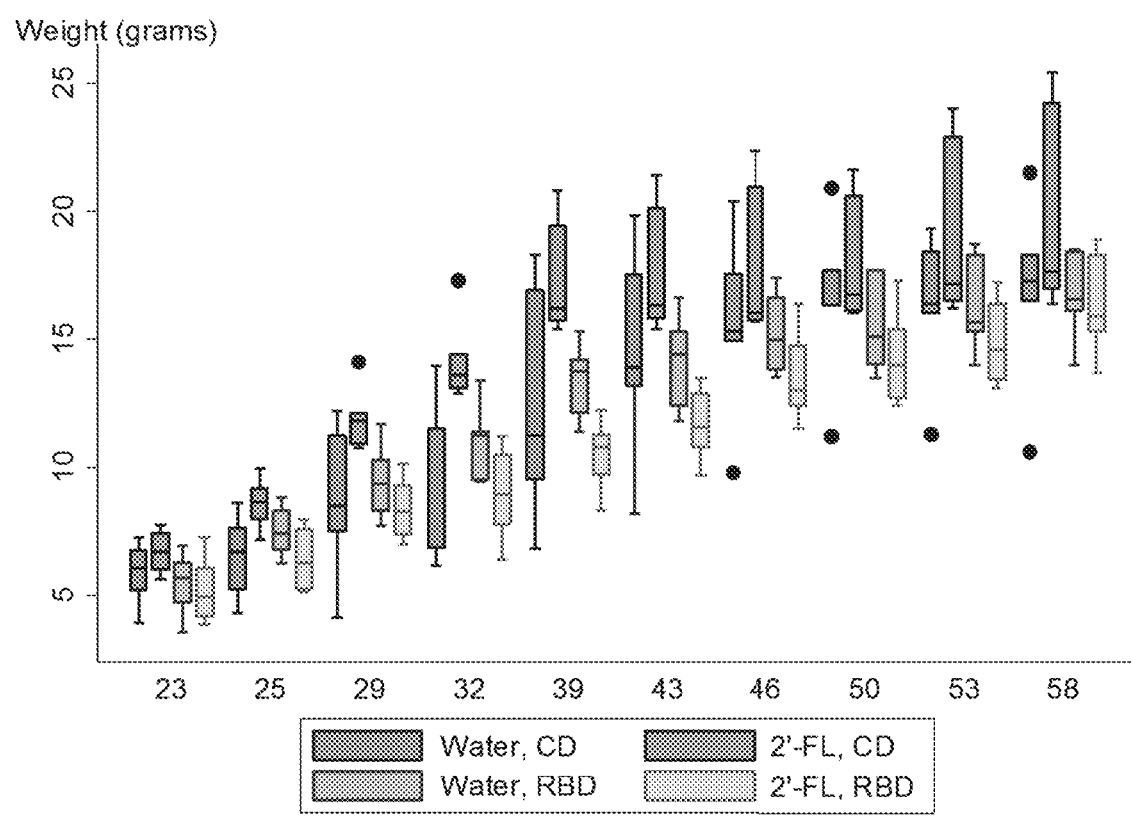
FIG. 42 is a graph showing weight change over time in an environmental enteropathy growth model described in FIG. 41. In the control diet, 2'-FL increased growth (p=0.034). In the regional based diet (a malnutrition diet still lacking nutrients), 2'-FL did not increase growth.

To further support the findings of the beneficial effect of 2' FL supplementation on infant growth, another experiment as outlined in FIG. 41 was performed. All dams were placed on Regional-based Diet when their pups were 10 days old. At weaning (3 wks of age), pups were placed on either control diet (CD) or continued on regional-based diet (RBD), which is a malnutrition diet lacking nutrients. At 4 wks of age, the pups were given either plain drinking water or 2-FL (2.5 g/L) in sipper sacs. Sipper sacs were changed and weighed every other day. Mice and food were weighed twice a week. Stool was collected at weaning, 6 weeks of age, and 8 weeks of age. Mice were sacrificed at 8 weeks of age. FIG. 42 shows that in the control diet, 2'-FL increased growth, while in the regional based diet (a malnutrition diet still lacking nutrients), 2'-FL did not increase growth.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of increasing weight gain in a subject, the method comprising:
    administering to a subject in need thereof an effective amount of a synthetic composition comprising an oligosaccharide and/or a glycoconjugate containing the oligosaccharide, wherein the oligosaccharide is an α1,2 fucosylated oligosaccharide, and wherein the subject is an infant with short bowel syndrome.

2. The method of claim 1, wherein the synthetic composition comprises the α1,2 fucosylated oligosaccharide and/or the glycoconjugate containing the α1,2 fucosylated oligosaccharide as its sole source of fucosylated oligosaccharides.

3. The method of claim 1, wherein the subject having intestinal failure is selected from the group consisting of a premature human infant, a human subject who has undergone a surgery, and a human subject who is suffering from undernutrition.

4. The method of claim 3, wherein the subject is a premature human infant having a gestational age of less than 34 weeks.

5. The method of claim 3, wherein the premature human infant has a weight-for-age Z-score of less than −2.0.

6. The method of claim 3, wherein the infant has undergone a surgery, which is an intestinal surgery or a bone marrow transplantation.

7. The method of claim 1, wherein the synthetic composition is administered to the subject for a period of at least 1 month.

8. The method of claim 1, wherein the α1,2 fucosylated oligosaccharide is selected from the group consisting of:
    (a) 2'-fucosyllactose (2'FL);
    (b) lacto-N-fucopentaose I (LNF-I);
    (c) lacto-N-difucohexaose I (LDFH-I);
    (d) lactodifucotetraose (LDFT), and
    (e) a variant of (a)-(d), which is identical to (a)-(d) except that the reducing end is N-acetylglucosamine instead of glucose.

9. The method of claim 1, wherein in the glycoconjugate, the oligosaccharide is conjugated with a carbohydrate, a lipid, a nucleic acid, a protein or a peptide.

10. The method of claim 1, wherein the oligosaccharide is synthesized chemically, purified from milk, or produced in a microorganism.

11. The method of claim 1, wherein the synthetic composition is an infant formula.

12. The method of claim 1, wherein the subject is FUT2 negative.

13. The method of claim 1, wherein the synthetic composition is free of a prebiotic and a probiotic.

14. The method of claim 13, wherein the subject is a premature human infant.

15. The method of claim 14, wherein the subject having intestinal failure is a premature human infant having a gestational age of less than 34 weeks.

16. The method of claim 14, wherein the infant has undergone a surgery, which is an intestinal surgery or a bone marrow transplantation.

17. The method of claim 13, wherein the α1,2 fucosylated oligosaccharide is selected from the group consisting of:
    (a) 2'-fucosyllactose (2'FL);
    (b) lacto-N-fucopentaose I (LNF-I);
    (c) lacto-N-difucohexaose I (LDFH-I);
    (d) lactodifucotetraose (LDFT), and
    (e) a variant of (a)-(d), which is identical to (a)-(d) except that the reducing end is N-acetylglucosamine instead of glucose.

18. The method of claim 13, wherein the oligosaccharide is synthesized chemically, purified from milk, or produced in a microorganism.

* * * * *

UNITED STATES PATENT AND TRADEMARK OFFICE
CERTIFICATE OF CORRECTION

PATENT NO. : 10,857,167 B2
APPLICATION NO. : 15/569993
DATED : December 8, 2020
INVENTOR(S) : Ardythe L. Morrow et al.

It is certified that error appears in the above-identified patent and that said Letters Patent is hereby corrected as shown below:

In the Claims

In Column 57, Lines 27-28, In Claim 3, delete "subject having intestinal failure" and replace with --infant with short bowel syndrome--

In Column 57, Line 29, In Claim 3, delete "subject" and replace with --infant--

In Column 57, Line 30, In Claim 3, delete "subject" and replace with --infant--

Signed and Sealed this
First Day of June, 2021

Drew Hirshfeld
*Performing the Functions and Duties of the*
*Under Secretary of Commerce for Intellectual Property and*
*Director of the United States Patent and Trademark Office*